(12) United States Patent
Cheung et al.

(10) Patent No.: US 11,597,764 B2
(45) Date of Patent: Mar. 7, 2023

(54) ANTI-L1-CAM ANTIBODIES AND USES THEREOF

(71) Applicant: MEMORIAL SLOAN KETTERING CANCER CENTER, New York, NY (US)

(72) Inventors: Nai-Kong V. Cheung, New York, NY (US); Hong Xu, New York, NY (US); Maya Suzuki-Nishijima, New York, NY (US); Brandon Nemieboka, New York, NY (US); Jason Lewis, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 162 days.

(21) Appl. No.: 16/622,274

(22) PCT Filed: Jun. 14, 2018

(86) PCT No.: PCT/US2018/037645
§ 371 (c)(1),
(2) Date: Dec. 12, 2019

(87) PCT Pub. No.: WO2018/232188
PCT Pub. Date: Dec. 20, 2018

(65) Prior Publication Data
US 2020/0199224 A1    Jun. 25, 2020

Related U.S. Application Data

(60) Provisional application No. 62/520,382, filed on Jun. 15, 2017.

(51) Int. Cl.
| | | |
|---|---|---|
| *C07K 16/28* | (2006.01) | |
| *C07K 16/30* | (2006.01) | |
| *G01N 33/534* | (2006.01) | |
| *A61K 39/395* | (2006.01) | |
| *A61P 35/00* | (2006.01) | |
| *A61K 45/06* | (2006.01) | |
| *A61K 39/00* | (2006.01) | |

(52) U.S. Cl.
CPC .......... *C07K 16/2803* (2013.01); *A61P 35/00* (2018.01); *C07K 16/30* (2013.01); *G01N 33/534* (2013.01); *A61K 45/06* (2013.01); *A61K 2039/505* (2013.01); *C07K 2317/24* (2013.01); *C07K 2317/31* (2013.01); *C07K 2317/41* (2013.01); *C07K 2317/54* (2013.01); *C07K 2317/55* (2013.01); *C07K 2317/622* (2013.01); *C07K 2317/732* (2013.01); *C07K 2317/76* (2013.01)

(58) Field of Classification Search
CPC ............... C07K 16/2803; C07K 16/30; C07K 2317/21; C07K 2317/24; C07K 2317/31; C07K 2317/54; C07K 2317/55; C07K 2317/622; C07K 2317/732; C07K 2317/76; C07K 2317/90; A61K 2039/505
See application file for complete search history.

(56) References Cited

U.S. PATENT DOCUMENTS

| | | |
|---|---|---|
| 6,972,323 B1 | 12/2005 | Serizawa et al. |
| 2008/0038257 A1 | 2/2008 | Han et al. |
| 2012/0282251 A1 | 11/2012 | Tremblay et al. |
| 2013/0189287 A1 | 7/2013 | Bregeon et al. |
| 2013/0236467 A1 | 9/2013 | Griggs et al. |
| 2015/0099707 A1 | 4/2015 | Pastan et al. |
| 2015/0344571 A1 | 12/2015 | Hong et al. |
| 2017/0137530 A1 | 5/2017 | Baehner et al. |

FOREIGN PATENT DOCUMENTS

| | | |
|---|---|---|
| KR | 20100064985 A | 6/2010 |
| WO | WO-2008/023946 A1 | 2/2008 |
| WO | WO-2009/127414 A2 | 10/2009 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al. Journal of Immunological Methods, 2018, vol. 463, p. 127-133.*
Fotinou et al., "Structure of an Fab Fragment Against a C-Terminal Peptide of hCG at 2.0: A Resolution," Journal of Biological Chemistry, vol. 273, No. 35, pp. 22515-22518 (Aug. 28, 1998).
International Search Report and Written Opinion, PCT/US2018/037645, Memorial Sloan Kettering Cancer Center, 10 pages (dated Sep. 28, 2018).

(Continued)

*Primary Examiner* — Hong Sang
(74) *Attorney, Agent, or Firm* — Foley & Lardner LLP

(57) ABSTRACT

The present disclosure relates generally to immunoglobulin-related compositions (e.g., antibodies or antigen binding fragments thereof) that can bind to and neutralize the activity of L1-CAM protein. The antibodies of the present technology are useful in methods for detecting and treating a L1-CAM-positive cancer in a subject in need thereof.

19 Claims, 67 Drawing Sheets

Specification includes a Sequence Listing.

(56) References Cited

OTHER PUBLICATIONS

Amstutz et al., "Production and characterization of a mouse/human chimeric antibody directed against human neuroblastoma". Int. J. Cancer:53, 147-152 (1993).
Hoefnagel et al., "A comparison of targetting of neuroblastoma with mIBG and anti LI-CAM antibody mAB chCE7: therapeutic efficacy in a neuroblastoma xenograft model and imaging of neuroblastoma patients". European Journal of Nuclear Medicine vol. 28, No. 3, Mar. 2001.

* cited by examiner

Figure 4

| Tumor Type | n | negative | weak | strong | total %(+) |
|---|---|---|---|---|---|
| Adrenal gland adenoma | 15 | 93 | 7 | 0 | 7 |
| Astrocytoma | 49 | 94 | 4 | 2 | 6 |
| Benigne nevus | 48 | 96 | 4 | 0 | 4 |
| Cervix carcinoma (squamous) | 44 | 98 | 2 | 0 | 2 |
| Chondrosarcoma | 11 | 82 | 0 | 18 | 18 |
| Colorectal cancer TMA | 375 | 85 | 2 | 13 | 15 |
| Endometrial carcinoma (serous) | 22 | 95 | 0 | 5 | 5 |
| Ependymoma | 12 | 92 | 0 | 8 | 8 |
| Epitheloid sarcoma | 2 | 50 | 50 | 0 | 50 |
| Esophageal carcinoma (adeno) TMA | 116 | 84 | 0 | 16 | 16 |
| Esophageal carcinoma (squamous) TMA | 141 | 98 | 0 | 2 | 2 |
| Esthesioneuroblastoma | 2 | 50 | 0 | 50 | 50 |
| Gastrointestinal stromal tumor | 103 | 44 | 10 | 46 | 56 |
| Granular cell tumor | 28 | 7 | 0 | 93 | 93 |
| Kapillary hemangioma | 26 | 61 | 12 | 27 | 39 |
| Kaposi sarcoma | 30 | 67 | 23 | 10 | 33 |
| Leiomyosarcoma | 129 | 93 | 4 | 3 | 7 |
| Liposarcoma | 104 | 93 | 7 | 0 | 7 |
| Malignant melanoma | 50 | 76 | 18 | 6 | 24 |
| Malignant mesothelioma | 28 | 96 | 4 | 0 | 4 |
| Malignant schwannoma | 54 | 80 | 6 | 14 | 20 |
| Medulloblastoma | 5 | 60 | 40 | 0 | 40 |
| Meningeoma | 49 | 98 | 2 | 0 | 2 |
| Mucosa associated lymphoid tissue | 49 | 98 | 2 | 0 | 2 |
| Neuroblastoma (pediatric) TMA | 72 | 4 | 7 | 89 | 96 |
| Neurofibroma | 43 | 98 | 0 | 2 | 2 |
| Oligodendroglioma | 30 | 90 | 10 | 0 | 10 |
| Pancreatic adenocarcinoma | 111 | 98 | 0 | 2 | 2 |
| Pancreatic neuroendocrine carcinoma | 63 | 92 | 0 | 8 | 8 |
| Paraganglioma | 10 | 60 | 0 | 40 | 40 |
| Pheochromocytoma | 29 | 24 | 17 | 59 | 76 |
| Primitive neuroectodermal tumors | 24 | 46 | 14 | 40 | 54 |
| Prostate cancer TMA | 3088 | 99.9 | 0.03 | 0 | 0.03 |
| Schwannoma | 44 | 14 | 54 | 32 | 86 |
| Small lung cancer | 49 | 92 | 8 | 0 | 8 |

Figure 6

*E71-Heavy Chain* (SEQ ID NO: 1)
QVQLQQPGDELVKPGASVKLSCKAS<u>GYTFT</u><u>SYWMQ</u>WVKQRPGQGLEWIG<u>EINPSNGRT</u>
<u>NYNEMFKS</u>KATLTVDKSSSTAYMQLSSLTSEDSAVYYCA<u>LYDGYYAMDY</u>WGQGTSVTVSS

*IGHV7-4-1 (most homolgous human sequence)* (SEQ ID NO: 2)
QVQLVQSGSELKKPGASVKVSCKAS<u>GYTFT</u><u>SYAMN</u>WVRQAPGQGLEWMG<u>WINTNTGN</u>
<u>PTYAQGFTG</u>RFVFSLDTSVSTAYLQICSLKAEDTAVYYCAR

*E71-Light Chain* (SEQ ID NO: 3)
DIVMSQSPSSLAVSVGEKVTMSC<u>KSSQSLLYSSNQKNYLA</u>WYQQKPGQSPKLLIY<u>WASTR</u>
<u>ES</u>GVPDRFTGSGSGTDFTLTISSVKAEDLALYYC<u>QQYHSYPFT</u>FGSGTKLEIKR

*IGKV-58 (most homologous human sequence)* (SEQ ID NO: 4)
DIVMTQSPDSLAVSLGERATINCK<u>SSQSVLYSSNNKNYLA</u>WYQQKPGQPPKLLIY<u>WASTRE</u>
<u>S</u>GVPDRFSGSGSGTDFTLTISSLQAEDVAVYYC<u>QQYYSTPLYT</u>FGQGTKLEI--

Figure 7

*E72-Heavy Chain* (SEQ ID NO: 5)
QVQLQQPGAELVKPGASVKLSCKASGYTFT<u>GYWMH</u>WVKQRPGHGLEWIG<u>EINPSN</u>
<u>GRTNYNEKFKS</u>KATLTVDKSSTTAFMQLSGLTSEDSAVYFCAR<u>DYYGTSYNFDY</u>WGQG
TTLTVSS

*IGHV1-2\*02/66.3/IGHJ4\*01/85.7 (most homolgous human sequence)* (SEQ ID NO: 6)
QVQLVQSGAEVKKPGASVKVSCKASGYTFT<u>GYYMH</u>WVRQAPGQGLEWMG<u>WINPN</u>
<u>SGGTNYAQKFQG</u>RVTMTRDTSISTAYMELSRLRSDDTAVYYCAR<u>YFDY</u>WGQGTLVTV
SS

*E72-Light Chain* (SEQ ID NO: 7)
DIQMTQSSSSFSVSLGDRVTITC<u>KANEDINNRLA</u>WYQQTPGNSPRLLIS<u>GATNLVT</u>GV
PSRFSGSGSGKDYTLTITSLQAEDFATYYC<u>QQYWSTPFT</u>FGSGTELEIKR

*IGKV1-NL1\*01/73.7/IGKJ2\*02/81.8 (most homologous human sequence)* (SEQ ID NO: 8)
DIQMTQSPSSLSASVGDRVTITC<u>RASQGISNSLA</u>WYQQKPGKAPKLLLY<u>AASRLES</u>GVP
SRFSGSGSGTDYTLTISSLQPEDFATYYC<u>QQYYSTPCT</u>FGQGTKLEIKR

Figure 8 huE71-H1 (SEQ ID NO: 9)
QVQLVQPGDELVKPGASVKLSCKASGYTFTSYWMQWVKQRPGQGLEWIGEINPSNGR
TNYNEMFKSKAVLSVDKSVSTAYMQLSSLTAEDTAVYYCALYDGYYAMDYWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK huE71-H2 (SEQ ID NO: 10)
QVQLVQSGSELKKPGASVKLSCKASGYTFTSYWMQWVRQAPGQGLEWIGEINPSNGR
TNYNEMFKSRAVLSVDTSVSTAYMQLCSLKAEDTAVYYCALYDGYYAMDYWGQGTLVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

Figure 9 huE71-H1 (SEQ ID NO: 11)
CAGGTGCAGCTGGTGCAGCCCGGCGACGAGCTGGTGAAGCCCGGCGCCTCCGTGAAGCTGTCCTGCAAGGCCTCCGGCTACACCTTCACCTCCTACTGGA
TGCAGTGGGTGAAGCAGCGGCCCGGCCAGGGCCTGGAGTGGATCGGCGAGATCAACCCCTCCAACGGCCGGACCAACTACAACGAGATGTTCAAGTCC
AAGGCCGTGCTGCTGTCCGTGGACAAGTCCGTGTCCACCGCCTACATGCAGCTGTCCTCCCTGACCGCCGAGGACACCGCCGTGTACTACTGCGCCCTGTACGA
CGGCTACTACGCCATGGACTACTGGGGCCAGGGCACCCTGGTGACCGTGTCCTCCGCCTCCACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCCGTCCTACAGTCCTCAGGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAGAGTTGAGCCCAAATCTTGTGACAAAACTCACACATGCCCACCGTGCCCAGCACCT
GAACTCCTGGGGGGACCGTCAGTCTTCCTCTTCCCCCCAAAACCCAAGGACACCCTCATGATCTCCCGGACCCCTGAGGTCACATGCGTGGTGGTGGACGT
GAGCCACGAAGACCCTGAGGTCAAGTTCAACTGGTACGTGGACGGCGTGGAGGTGCATAATGCCAAGACAAAGCCGCGGGAGGAGCAGTACAACAGCA
CGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGTGTACACCCTGCCCCCATCCCGGGATGAGCTGACCAAGAACCAGGTCAGCCT
GACCTGCCTGGTCAAAGGCTTCTATCCCAGCGACATCGCCGTGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAATGA huE71-H2 (SEQ ID NO: 12)
CAGGTGCAGCTGGTGCAGTCCGGCTCCGAGCTGAAGAAGCCCGGCGCCTCCGTGAAGCTGTCCTGCAAGGCCTCCGGCTACACCTTCACCTCCTACTGGA
TGCAGTGGGTGCGGCAGGCCCCGGCCAGGGCCTGGAGTGGATCGGCGAGATCAACCCCTCCAACGGCCGGACCAACTACAACGAGATGTTCAAGTCC
GGGCCGTGCTGTCCGTGGACACCTCCGTGTCCACCGCCTACATGCAGCTGTCCTCCCTGAAGGCCGAGGACACCGCCGTGTACTACTGCGCCCTGTACGAC
GGCTACTACGCCATGGACTACTGGGGCCAGGGCACCCTGGTGACCGTGTCCTCCGCCTCCACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGTGACGGTGTCGTGGAACTCAGGCGCCCTGACCAGCG
GCGTGCACACCTTCCCGGCCGTCCTACAGTCCTCAGGACTCTACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCTTGTGACAAAACTCACACATGCCCACCGTGCCCAGCACCTG
AACTCCTGGGGGGACCGTCAGTCTTCCTCTTCCCCCCAAAACCCAAGGACACCCTCATGATCTCCCGGACCCCTGAGGTCACATGCGTGGTGGTGGACGTG
AGCCACGAAGACCCTGAGGTCAAGTTCAACTGGTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCCCCATCCCGGGATGAGCTGACCAAGAACCAGGTCAGCCTG
ACCTGCCTGGTCAAAGGCTTCTATCCCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTTCTCATGCTCCGTGATGCATGAGGCTC
TGCACAACCACTACACGCAGAAGAGCCTCTCCCTGTCTCCGGGTAAATGA

Figure 10 huE71-L1 (SEQ ID NO: 13)
DIVMTQSPSSLAVSVGERVTMSCKSSQSLLYSSNQKNYLAWYQQKPGQSPKLLIYWAST
RESGVPDRFSGSGSGTDFTLTISSVKAEDVALYYCQQYHSYPFTFGQGTKLEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC huE71-L2 (SEQ ID NO: 14)
DIVMTQSPDSLAVSLGERVTMNCKSSQSLLYSSNQKNYLAWYQQKPGQPPKLLIYWAST
RESGVPDRFSGSGSGTDFTLTISSLQAEDVALYYCQQYHSYPFTFGQGTKLEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Figure 11 huE71-L1  (SEQ ID NO: 15)
GACATCGTGATGACCCAGTCCCCCTCCTCCCTGGCCGTGTCCGTGGGCGAGCGGGTGACCATGTCCTGCAAG
TCCTCCCAGTCCCTGCTGTACTCCTCCAACCAGAAGAACTACCTGGCCTGGTACCAGCAGAAGCCCGGCCAGT
CCCCCAAGCTGCTGATCTACTGGGCCTCCACCCGGGAGTCCGGCGTGCCCGACCGGTTCTCCGGCTCCGGCT
CCGGCACCGACTTCACCCTGACCATCTCCTCCGTGAAGGCCGAGGACGTGGCCCTGTACTACTGCCAGCAGT
ACCACTCCTACCCCTTCACCTTCGGCCAGGGCACCAAGCTGGAGATCAAGCGGACCGTGGCCGCCCCCTCCG
TGTTCATCTTCCCCCCCTCCGACGAGCAGCTGAAGTCCGGCACCGCCTCCGTGGTGTGCCTGCTGAACAACTT
CTACCCCGGGAGGCCAAGGTGCAGTGGAAGGTGGACAACGCCCTGCAGTCCGGCAACTCCCAGGAGTCC
GTGACCGAGCAGGACTCCAAGGACTCCACCTACTCCCTGTCCTCCACCCTGACCCTGTCCAAGGCCGACTACG
AGAAGCACAAGGTGTACGCCTGCGAGGTGACCCACCAGGGCCTGTCCTCCCCCGTGACCAAGTCCTTCAACC
GGGGCGAGTGCTAG huE71-L2  (SEQ ID NO: 16)
GACATCGTGATGACCCAGTCCCCCGACTCCCTGGCCGTGTCCCTGGGCGAGCGGGTGACCATGAACTGCAAG
TCCTCCCAGTCCCTGCTGTACTCCTCCAACCAGAAGAACTACCTGGCCTGGTACCAGCAGAAGCCCGGCCAG
CCCCCCAAGCTGCTGATCTACTGGGCCTCCACCCGGGAGTCCGGCGTGCCCGACCGGTTCTCCGGCTCCGGC
TCCGGCACCGACTTCACCCTGACCATCTCCTCCCTGCAGGCCGAGGACGTGGCCCTGTACTACTGCCAGCAGT
ACCACTCCTACCCCTTCACCTTCGGCCAGGGCACCAAGCTGGAGATCAAGCGGACCGTGGCCGCCCCCTCCG
TGTTCATCTTCCCCCCCTCCGACGAGCAGCTGAAGTCCGGCACCGCCTCCGTGGTGTGCCTGCTGAACAACTT
CTACCCCGGGAGGCCAAGGTGCAGTGGAAGGTGGACAACGCCCTGCAGTCCGGCAACTCCCAGGAGTCC
GTGACCGAGCAGGACTCCAAGGACTCCACCTACTCCCTGTCCTCCACCCTGACCCTGTCCAAGGCCGACTACG
AGAAGCACAAGGTGTACGCCTGCGAGGTGACCCACCAGGGCCTGTCCTCCCCCGTGACCAAGTCCTTCAACC
GGGGCGAGTGCTAG

Figure 12 huE72-H1  (SEQ ID NO: 17)

QVQLVQPGAEVVKPGASVKLSCKASGYTFTGYWMHWVKQAPGQGLEWIGEINPSNGR
TNYNERFKSKATLTVDKSITTAFMELSRLRSDDTAVYFCARDYYGTSYNFDYWGQGTLLTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK huE72-H2  (SEQ ID NO: 18)

QVQLVQPGAEVKKPGASVKLSCKASGYTFTGYWMHWVRQAPGQGLEWIGEINPSNGR
TNYNERFKSRATLTVDKSISTAYMELSRLRSDDTAVYFCARDYYGTSYNFDYWGQGTLLTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK

Figure 13 huE72-H1 (SEQ ID NO: 19)

[sequence illegible]

huE72-H2 (SEQ ID NO: 20)

[sequence illegible]

Figure 14 huE72-L1 (SEQ ID NO: 21)

DIQMTQSSSSFSVSVGDRVTITCKANEDINNRLAWYQQKPGKSPRLLISGATNLVTGVPSR
FSGSGSGTDYTLTISSLQAEDFATYYCQQYWSTPFTFGQGTELEIKRTVAAPSVFIFPPSDEQ
LKSGTASVVCLLNNFYPREAKVQWKVDNALQSGNSQESVTEQDSKDSTYSLSSTLTLSKA
DYEKHKVYACEVTHQGLSSPVTKSFNRGEC huE72-L2 (SEQ ID NO: 22)

DIQMTQSPSSLSVSVGDRVTITCKANEDINNRLAWYQQKPGKAPKLLISGATNLVTGVPSR
FSGSGSGTDYTLTISSLQPEDFATYYCQQYWSTPFTFGQGTELEIKRTVAAPSVFIFPPSDEQ
LKSGTASVVCLLNNFYPREAKVQWKVDNALQSGNSQESVTEQDSKDSTYSLSSTLTLSKA
DYEKHKVYACEVTHQGLSSPVTKSFNRGEC

Figure 15 huE72-L1 (SEQ ID NO: 23)
[sequence illegible]

huE72-L2 (SEQ ID NO: 24)
[sequence illegible]

Figure 16 chE71-IgG1

*Light chain* (SEQ ID NO: 25)
DIVMSQSPSSLAVSVGEKVTMSCKSSQSLLYSSNQKNYLAWYQQKPGQSPKLLIYWASTRE
SGVPDRFTGSGSGTDFTLTISSVKAEDLALYYCQQYHSYPFTFGSGTKLEIKRTVAAPSVFIFP
PSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

*Heavy chain* (SEQ ID NO: 26)
QVQLQQPGDELVKPGASVKLSCKASGYTFTSYWMQWVKQRPGQGLEWIGEINPSNGRT
NYNEMFKSKATLTVDKSSSTAYMQLSSLTSEDSAVYYCALYDGYYAMDYWGQGTSVTVSS
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSC
SVMHEALHNHYTQKSLSLSPGK

Figure 17 chE71-IgG1
Light chain (SEQ ID NO: 27)
GACATTGTGATGTCACAGTCTCCATCCTCCCTAGCTGTGTCAGTTGGAGAGAAGGTTACTATGAGCTGCAAGTCCAGTC
AGAGCCTTTTATATAGTAGCAATCAAAAGAACTACTTGGCCTGGTACCAGCAGAAACCAGGGCAGTCTCCTAAACTGCT
GATTTACTGGGCATCCACTAGGGAATCTGGGGTCCCTGATCGCTTCACAGGCAGTGGATCTGGGACAGATTTCACTCTC
ACCATTAGCAGTGTGAAGGCTGAAGACCTGGCACTTTATTACTGTCAGCAATATCATAGCTATCCATTCACGTTCGGCTC
GGGGACAAAGCTGGAAATAAAGCGGACCGTGGCCGCCCCCTCCGTGTTCATCTTCCCGCCCTCCGACGAGCAGCTGA
AGTCCGGCACCGCCTCCGTGGTGTGCCTGCTGAACAACTTCTACCCCCGGGAGGCCAAGGTGCAGTGGAAGGTGGAC
AACGCCCTGCAGTCCGGCAACTCCCAGGAGTCCGTGACCGAGCAGGACTCCAAGGACTCCACCTACTCCCTGTCCTCC
ACCCTGACCCTGTCCAAGGCCGACTACGAGAAGCACAAGGTGTACGCCTGCGAGGTGACCCACCAGGGCCTGTCCTC
CCCCGTGACCAAGTCCTTCAACCGGGGCGAGTGCTAG Heavy chain (SEQ ID NO: 28)
CAGGTCCAACTGCAGCAGCCTGGGGATGAACTGGTGAAGCCTGGGGCTTCAGTGAAGCTGTCCTGCAAGGCTTCTGG
CTACACCTTCACCAGCTACTGGATGCAGTGGGTGAAGCAGAGGCCTGGACAAGGCCTTGAGTGGATTGGAGAGATTAA
TCCTAGCAACGGTCGTACTAATTATAATGAGATGTTCAAGAGCAAGGCCACACTGACTGTAGACAAATCCTCCAGCACA
GCCTACATGCAACTCAGCAGCCTGACATCTGAGGACTCTGCGGTCTATTACTGTGCCCTCTATGATGGTTACTACGCTAT
GGACTACTGGGGTCAAGGAACCTCAGTCACCGTCTCCTCAGCCTCCACCAAGGGCCCATCGGTCTTCCCCCTGGCACC
CTCCTCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCCGTCCTACAGTCCTCAGGACTCTACTCCC
TCAGCAGCGTGGTGACCGTGCCCTCCAGCAGCTTGGGCACCCAGACCTACATCTGCAACGTGAATCACAAGCCCAGCA
ACACCAAGGTGGACAAGAGAGTTGAGCCCAAATCTTGTGACAAAACTCACACATGCCCACCGTGCCCAGCACCTGAAC
TCCTGGGGGGACCGTCAGTCTTCCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTACGTGGACGGCGTGGAGGTGCAT
AATGCCAAGACAAAGCCGCGGGAGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCAGCCCCCATCGAGAAAACCATCTC
CAAAGCCAAAGGGCAGCCCCGAGAACCACAGGTGTACACCCTGCCCCCATCCCGGGATGAGCTGACCAAGAACCAGG
TCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAACCACTACACGCAGAAGAG
CCTCTCCCTGTCTCCGGGTAAATGA

Figure 18 chE72-Light Chain (SEQ ID NO: 29)

DIQMTQSSSSFSVSLGDRVTITCKANEDINNRLAWYQQTPGNSPRLLISGATNLVTGVP
SRFSGSGSGKDYTLTITSLQAEDFATYYCQQYWSTPFTFGSGTELEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC chE72-Heavy Chain-IgG1 (SEQ ID NO: 30)

QVQLQQPGDELVKPGASVKLSCKASGYTFTSYWMQWVKQRPGQGLEWIGEINPSN
GRTNYNEMFKSKATLTVDKSSSTAYMQLSSLTSEDSAVYYCALYDGYYAMDYWGQGTS
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

Figure 19 chE72-Light Chain (SEQ ID NO: 31)

GACATCCAGATGACCCAGTCCTCCTCCAGCTTCTCCGTGTCCCTGGGCGACAGAGTGACCATCACATGCAAGGCCAACGAG
GACATCAACAACCGGCTGGCCTGGTATCAGCAGACCCCCGGCAACTCCCCCAGACTGCTGATCTCTGGCGCCACCAACCTC
GTGACCGGCGTGCCCAGTAGATTCTCCGGCTCTGGCTCCGGCAAGGACTACACCCTGACAATCACATCCCTGCAGGCCGAG
GACTGGCCAACCTACTACTGCCAGCAGTACTGGTCCACCCCCTTCACCTTTGGCAGCGGCACCAAGCTGGAAATCAAGCGG
ACAGTGGCCGCTCCCTCCGTGTTCATCTTCCCACCTTCCGACGAGCAGCTGAAGTCCGGCACCGCTTCTGTCGTGTGCCTGC
TGAACAACTTCTACCCCCGCGAGGCCAAGGTGCAGTGGAAGGTGGACAACGCCCTGCAGTCCGGCAACAGCCAGGAATCC
GTGACCGAGCAGGACTCCAAGGACAGCACCTACTCCCTGTCCTCCACCCTGACCCTGTCCAAGGCCGACTACGAGAAGCAC
AAGGTGTACGCCTGCGAAGTGACCCACCAGGGCCTGTCTAGCCCCGTGACCAAGTCTTTCAACCGGGGCGAGTGCTAG chE72-Heavy Chain-IgG1 (SEQ ID NO: 32)

CAGGTCCAACTGCAGCAGCCTGGGGATGAACTGGTGAAGCCTGGGGCTTCAGTGAAGCTGTCCTGCAAGGCTTCTGGCTA
CACCTTCACCAGCTACTGGATGCAGTGGGTGAAGCAGAGGCCTGGACAAGGCCTTGAGTGGATTGGAGAGATTAATCCTA
GCAACGGTCGTACTAATTATAATGAGATGTTCAAGAGCAAGGCCACACTGACTGTAGACAAATCCTCCAGCACAGCCTACAT
GCAACTCAGCAGCCTGACATCTGAGGACTCTGCGGTCTATTACTGTGCCCTCTATGATGGTTACTACGCTATGGACTACTGGG
GTCAAGGAACCTCAGTCACCGTCTCCTCAGCCTCCACCAAGGGCCCATCGGTCTTCCCCCTGGCACCCTCCTCCAAGAGCAC
CTCTGGGGGCACAGCGGCCCTGGGCTGCCTGGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGACTCTACTCCCTCAGCAGCGTGGTGACCGTGCC
CTCCAGCAGCTTGGGCACCCAGACCTACATCTGCAACGTGAATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTTCCTCTT
CCCCCCAAAACCCAAGGACACCCTCATGATCTCCCGGACCCCTGAGGTCACATGCGTGGTGGTGGACGTGAGCCACGAAGA
CCCTGAGGTCAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACAAGTGCAAGGT
CTCCAACAAAGCCCTCCCAGCCCCCATCGAGAAAACCATCTCCAAAGCCAAAGGGCAGCCCCGAGAACCACAGGTGTACAC
CCTGCCCCCATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCTTCTCATGCTCCGTGATGCATGAGGC
TCTGCACAACCACTACACGCAGAAGAGCCTCTCCCTGTCTCCGGGTAAATGA

Figure 20 huE71-H1L1-IgG1 Heavy Chain Sequences

*Amino acid:* (SEQ ID NO: 33)
QVQLVQPGDELVKPGASVKLSCKASGYTFTSYWMQWVKQRPGQGLEWIGEINPSNGRTNYNEMFKSKAVLSVDKSVSTAY
MQLSSLTAEDTAVYYCALYDGYYAMDYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK*

*cDNA:* (SEQ ID NO: 34)
CAGGTGCAGCTGGTGCAGCCCGGCGACGAGCTGGTGAAGCCCGGCGCCTCCGTGAAGCTGTCCTGCAAGGCCTCCGG
CTACACCTTCACCTCCTACTGGATGCAGTGGGTGAAGCAGCGGCCCGGCCAGGGCCTGGAGTGGATCGGCGAGATCAAC
CCCTCCAACGGCCGGACCAACTACAACGAGATGTTCAAGTCCAAGGCCGTGCTGTCCGTGGACAAGTCCGTGTCCACCG
CCTACATGCAGCTGTCCTCCCTGACCGCCGAGGACACCGCCGTGTACTACTGCGCCCTGTACGACGGCTACTACGCCATG
GACTACTGGGGCCAGGGCACCCTGGTGACCGTGTCCTCCGCCTCCACCAAGGGCCCATCGGTCTTCCCCCTGGCACCCT
CCTCCAAGAGCACCTCTGGGGGCACAGCGGCCCTGGGCTGCCTGGTCAAGGACTACTTCCCCGAACCGGTGACGGTGT
CGTGGAACTCAGGCGCCCTGACCAGCGGCGTGCACACCTTCCCGGCCGTCCTACAGTCCTCAGGACTCTACTCCCTCAG
CAGCGTGGTGACCGTGCCCTCCAGCAGCTTGGGCACCCAGACCTACATCTGCAACGTGAATCACAAGCCCAGCAACACC
AAGGTGGACAAGAGAGTTGAGCCCAAATCTTGTGACAAAACTCACACATGCCCACCGTGCCCAGCACCTGAACTCCTGG
GGGGACCGTCAGTCTTCCTCTTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCATCGAGAAAACCATCTCCAAAGCCAAAG
GGCAGCCCCGAGAACCACAGGTGTACACCCTGCCCCCATCCCGGGATGAGCTGACCAAGAACCAGGTCAGCCTGACCT
GCCTGGTCAAAGGCTTCTATCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTCTCCCTGTCTCCGG
GTAAATGA

Figure 21 huE71-H1L1- light chain sequences

*Amino acid:* (SEQ ID NO: 35)
DIVMTQSPSSLAVSVGERVTMSCKSSQSLLYSSNQKNYLAWYQQKPGQSPKLLIYWASTRESGVPDRFSGSGSGT
DFTLTISSVKAEDVALYYCQQYHSYPFTFGQGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSFNRGEC*

*cDNA:* (SEQ ID NO: 36)
GACATCGTGATGACCCAGTCCCCCCTCCTCCCTGGCCGTGTCCGTGGGCGAGCGGGTGACCATGTCCTGCAAGT
CCTCCCAGTCCCTGCTGTACTCCTCCAACCAGAAGAACTACCTGGCCTGGTACCAGCAGAAGCCCGGCCAGTC
CCCCAAGCTGCTGATCTACTGGGCCTCCACCCGGGAGTCCGGCGTGCCCGACCGGTTCTCCGGCTCCGGCTCC
GGCACCGACTTCACCCTGACCATCTCCTCCGTGAAGGCCGAGGACGTGGCCCTGTACTACTGCCAGCAGTACC
ACTCCTACCCCTTCACCTTCGGCCAGGGCACCAAGCTGGAGATCAAGCGGACCGTGGCCGCCCCCTCCGTGTT
CATCTTCCCCCCCTCCGACGAGCAGCTGAAGTCCGGCACCGCCTCCGTGGTGTGCCTGCTGAACAACTTCTACC
CCCGGGAGGCCAAGGTGCAGTGGAAGGTGGACAACGCCCTGCAGTCCGGCAACTCCCAGGAGTCCGTGACC
GAGCAGGACTCCAAGGACTCCACCTACTCCCTGTCCTCCACCCTGACCCTGTCCAAGGCCGACTACGAGAAGC
ACAAGGTGTACGCCTGCGAGGTGACCCACCAGGGCCTGTCCTCCCCCGTGACCAAGTCCTTCAACCGGGGCG
AGTGCTAG

Figure 22 huE72-(HIL2)-IgG1-Heavy chain
Amino acid: (SEQ ID NO: 37)
QVQLVQPGAEVVKPGASVKLSCKASGYTFTGYWMHWVKQAPGQGLEWIGEINPSNGRTNYNEKFKSKATLTVDKSITTAFM
ELSRLRSDDTAVYFCARDYYGTSYNFDYWGQGTLLTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGK cDNA: (SEQ ID NO: 38)
CAGGTGCAGCTGGTGCAGCCTGGGGCTGAAGTGGTGAAGCCAGGGGCCTCGGTGAAGCTGTCCTGCAAGGCTTCCGGCT
ACACCTTCACCGGCTACTGGATGCACTGGGTCAAGCAGGCCCCTGGACAGGGCCTGGAATGGATCGGCGAGATCAACCCT
TCCAACGGCCGGACCAACTACAACGAGAAGTTCAAGTCCAAGGCCACCCTGACCGTGGACAAGTCCATCACCACCGCCTT
CATGGAACTGTCCCGGCTGAGATCCGACGATACCGCCGTGTACTTCTGCGCCAGAGACTACTACGGCACCTCCTACAACTTC
GACTACTGGGGCCAGGGCACCCTGCTGACCGTGTCCTCTGCTTCTACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCAACACCAAGGT
GGACAAGAGAGTTGAGCCCAAATCTTGTGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGGAGGTGCATAATGCCAAGACAAAGCC
GCGGGAGGAGCAGTACAACAGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAGGTCAGCCTGACCTGCCTGGTCAAAG
GCTTCTATCCCAGCGACATCGCCGTGGAGTGGGAGAGCAATGGGCAGCCGGAGAACAACTACAAGACCACGCCTCCCGT
GCTGGACTCCGACGGCTCCTTCTTCCTCTACAGCAAGCTCACCGTGGACAAGAGCAGGTGGCAGCAGGGGAACGTCTTCT
CATGCTCCGTGATGCATGAGGCTCTGCACAACCACTACACGCAGAAGAGCCTCTCCCTGTCTCCGGGTAAA

Figure 23 huE72-(H1L2)-IgG1-Light chain

*Amino acid:* (SEQ ID NO: 39)
DIQMTQSPSSLSVSVGDRVTITCKANEDINNRLAWYQQKPGKAPKLLISGATNLVTGVPSRFSGSG
SGTDYTLTISSLQPEDFATYYCQQYWSTPFTFGQGTELEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQ
GLSSPVTKSFNRGEC

*cDNA:* (SEQ ID NO: 40)
GACATCCAGATGACCCAGTCCCCCTCCTCCCTGTCCGTGTCTGTGGGCGACAGAGTGACCATC
ACATGCAAGGCCAACGAGGACATCAACAACCGGCTGGCCTGGTATCAGCAGAAGCCCGGCAA
GGCCCCCAAGCTGCTGATCTCTGGCGCCACCAATCTCGTGACCGGCGTGCCCTCCAGATTCTC
CGGCTCTGGCTCTGGCACCGACTATACCCTGACCATCTCCAGCCTGCAGCCGAGGACTTCGC
CACCTACTACTGCCAGCAGTACTGGTCCACCCCTTCACCTTTGGCCAGGGCACCGAGCTGGA
AATCAAGCGGACAGTGGCCGCTCCCTCCGTGTTCATCTTCCCACCTTCCGACGAGCAGCTGAA
GTCCGGCACCGCTTCTGTCGTGTGCCTGCTGAACAACTTCTACCCCCGCGAGGCCAAGGTGCA
GTGGAAGGTGGACAACGCCCTGCAGTCCGGCAACTCCCAGGAATCCGTGACCGAGCAGGAC
TCCAAGGACAGCACCTACAGCCTGTCCTCCACCCTGACCCTGTCCAAGGCCGACTACGAGAAG
CACAAGGTGTACGCCTGCGAAGTGACCCACCAGGGCCTGTCTAGCCCCGTGACCAAGTCTTTC
AACCGGGGCGAGTGCTAG

Figure 24 chE71-IgG4

*Light chain* (SEQ ID NO: 41)
DIVMSQSPSSLAVSVGEKVTMSCKSSQSLLYSSNQKNYLAWYQQKPGQSPKLLIYWASTRE
SGVPDRFTGSGSGTDFTLTISSVKAEDLALYYCQQYHSYPFTFGSGTKLEIKRTVAAPSVFIFP
PSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

*Heavy chain* (SEQ ID NO: 42)
QVQLQQPGDELVKPGASVKLSCKASGYTFTSYWMQWVKQRPGQGLEWIGEINPSNGRT
NYNEMFKSKATLTVDKSSSTAYMQLSSLTSEDSAVYYCALYDGYYAMDYWGQGTSVTVSS
ASTKGPSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPSCPAPEFLGGPSVFLFPPK
PKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSRWQEGNVFSCSV
MHEALHNHYTQKSLSLSLGK

Figure 25 chE71-IgG4 Light Chain (SEQ ID NO: 43)
TACATTGTGATGTCACAGTCTCCATCCTCCCTAGCTGTGTCAGTTGGAGAGAAGGTTACTATGAGCTGCAAGTCCAGTCAG
AGCCTTTTATATAGTAGCAATCAAAAGAACTACTTGGCCTGGTACCAGCAGAAACCAGGGCAGTCTCCTAAACTGCTGATT
TACTGGGCATCCACTAGGGAATCTGGGGTCCCTGATCGCTTCACAGGCAGTGGATCTGGGACAGATTTCACTCTCACCATT
AGCAGTGTGAAGGCTGAAGACCTGGCACTTTATTACTGTCAGCAATATCATAGCTATCCATTCACGTTCGGCTCGGGGACA
AAGCTGGAAATAAAGCGGACCGTGGCCGCCCCTCCGTGTTCATCTTCCCCCCTCCGACGAGCAGCTGAAGTCCGGCA
CCGCCTCCGTGGTGTGCCTGCTGAACAACTTCTACCCCGGGAGGCCAAGGTGCAGTGGAAGGTGGACAACGCCCTGC
AGTCCGGCAACTCCCAGGAGTCCGTGACCGAGCAGGACTCCAAGGACTCCACCTACTCCCTGTCCTCCACCCTGACCCT
GTCCAAGGCCGACTACGAGAAGCACAAGGTGTACGCCTGCGAGGTGACCCACCAGGGCCTGTCCTCCCCCGTGACCAA
GTCCTTCAACCGGGGCGAGTGCTAG chE71-IgG4 Heavy Chain (SEQ ID NO: 44)
CAGGTCCAACTGCAGCAGCCTGGGGATGAACTGGTGAAGCCTGGGGCTTCAGTGAAGCTGTCCTGCAAGGCTTCTGGCT
ACACCTTCACCAGCTACTGGATGCAGTGGGTGAAGCAGAGGCCTGGACAAGGCCTTGAGTGGATTGGAGAGATTAATCCT
AGCAACGGTCGTACTAATTATAATGAGATGTTCAAGAGCAAGGCCACACTGACTGTAGACAAATCCTCCAGCACAGCCTAC
ATGCAACTCAGCAGCCTGACATCTGAGGACTCTGCGGTCTATTACTGTGCCCTCTATGATGGTTACTACGCTATGGACTACT
GGGGTCAAGGAACCTCAGTCACCGTCTCCTCAGCCTCCACCAAGGGCCCCTCCGTGTTCCCCCTGGCCCCTGCTCCCG
GTCCACCTCCGAGTCCACCGCCGCCCTGGGCTGCCTGGTGAAGGACTACTTCCCCGAGCCCGTGACCGTGTCCTGGAAC
TCCGGCGCCCTGACCTCCGGCGTGCACACCTTCCCCGCCGTGCTGCAGTCCTCCGGCCTGTACTCCCTGTCCTCCGTGG
TGACCGTGCCCTCCTCCTCCCTGGGCACCAAGACCTACACCTGCAACGTGGACCACAAGCCCTCCAACACCAAGGTGGA
CAAGCGGGTGGAGTCCAAGTACGGCCCCCCCTGCCCCTCCTGCCCCGCCCCCGAGTTCCTGGGCGGCCCCTCCGTGTTC
CTGTTCCCCCCCAAGCCCAAGGACACCCTGATGATCTCCCGGACCCCCGAGGTGACCTGCGTGGTGGTGGACGTGTCCC
AGGAGGACCCCGAGGTGCAGTTCAACTGGTACGTGGACGGCGTGGAGGTGCACAACGCCAAGACCAAGCCCCGGGAG
GAGCAGTTCAACTCCACCTACCGGGTGGTGTCCGTGCTGACCGTGCTGCACCAGGACTGGCTGAACGGCAAGGAGTACA
AGTGCAAGGTGTCCAACAAGGGCCTGCCCTCCTCCATCGAGAAGACCATCTCCAAGGCCAAGGGCCAGCCCCGGGAGC
CCCAGGTGTACACCCTGCCCCCCTCCCAGGAGGAGATGACCAAGAACCAGGTGTCCCTGACCTGCCTGGTGAAGGGCTT
CTACCCCTCCGACATCGCCGTGGAGTGGGAGTCCAACGGCCAGCCCGAGAACAACTACAAGACCACCCCCCCCGTGCTG
GACTCCGACGGCTCCTTCTTCCTGTACTCCCGGCTGACCGTGGACAAGTCCCGGTGGCAGGAGGGCAACGTGTTCTCCT
GCTCCGTGATGCACGAGGCCCTGCACAACCACTACACCCAGAAGTCCCTGTCCCTGTCCCTGGGCAAGTGA

Figure 26 huE71-IgG4

*Light chain* (SEQ ID NO: 45)

DIVMTQSPSSLAVSVGERVTMSCKSSQSLLYSSNQKNYLAWYQQKPGQSPKLLIYWASTR
ESGVPDRFSGSGSGTDFTLTISSVKAEDVALYYCQQYHSYPFTFGQGTKLEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC*

*Heavy chain* (SEQ ID NO: 46)

QVQLVQPGDELVKPGASVKLSCKASGYTFTSYWMQWVKQRPGQGLEWIGEINPSNGRT
NYNEMFKSKAVLSVDKSVSTAYMQLSSLTAEDTAVYYCALYDGYYAMDYWGQGTLVTVSS
ASTKGPSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPSCPAPEFLGGPSVFLFPPK
PKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSRWQEGNVFSCSV
MHEALHNHYTQKSLSLSLGK

Figure 27 huE71-IgG4 Light Chain  (SEQ ID NO: 47)
GACATCGTGATGACCCAGTCCCCCTCCTCCCTGGCCGTGTCCGTGGGCGAGCGGGTGACCATGTCCTGCAAGTCCTCCCAGTCCCT
GCTGTACTCCTCCAACCAGAAGAACTACCTGGCCTGGTACCAGCAGAAGCCCGGCCAGTCCCCCAAGCTGCTGATCTACTGGGCC
TCCACCCGGGAGTCCGGCGTGCCCGACCGGTTCTCCGGCTCCGGCTCCGGCACCGACTTCACCCTGACCATCTCCTCCGTGAAGG
CCGAGGACGTGGCCCTGTACTACTGCCAGCAGTACCACTCCTACCCCTTCACCTTCGGCCAGGGCACCAAGCTGGAGATCAAGCG
GACCGTGGCCGCCCCCTCCGTGTTCATCTTCCCCCCCTCCGACGAGCAGCTGAAGTCCGGCACCGCCTCCGTGGTGTGCCTGCTG
AACAACTTCTACCCCGGGAGGCCAAGGTGCAGTGGAAGGTGGACAACGCCCTGCAGTCCGGCAACTCCCAGGAGTCCGTGAC
CGAGCAGGACTCCAAGGACTCCACCTACTCCCTGTCCTCCACCCTGACCCTGTCCAAGGCCGACTACGAGAAGCACAAGGTGTAC
GCCTGCGAGGTGACCCACCAGGGCCTGTCCTCCCCGTGACCAAGTCCTTCAACCGGGGCGAGTGCTAG huE71-IgG4 Heavy Chain  (SEQ ID NO: 48)
CAGGTGCAGCTGGTGCAGCCCGGCGACGAGCTGGTGAAGCCCGGCGCCTCCGTGAAGCTGTCCTGCAAGGCCTCCGGCTACAC
CTTCACCTCCTACTGGATGCAGTGGGTGAAGCAGCGGCCCGGCCAGGGCCTGGAGTGGATCGGCGAGATCAACCCCTCCAACGG
CCCGGACCAACTACAACGAGATGTTCAAGTCCAAGGCCGTGCTGTCCGTGGACAAGTCCGTGTCCACCGCCTACATGCAGCTGTCC
TCCCTGACCGCCGAGGACACCGCCGTGTACTACTGCGCCCTGTACGACGGCTACTACGCCATGGACTACTGGGGCCAGGGCACCC
TGGTGACCGTGTCCTCCGCCTCCACCAAGGGCCCCTCCGTGTTCCCCCTGGCCCCCTGCTCCCGGTCCACCTCCGAGTCCACCGCC
GCCCTGGGCTGCCTGGTGAAGGACTACTTCCCCGAGCCCGTGACCGTGTCCTGGAACTCCGGCGCCCTGACCTCCGGCGTGCAC
ACCTTCCCCGCCGTGCTGCAGTCCTCCGGCCTGTACTCCCTGTCCTCCGTGGTGACCGTGCCCTCCTCCTCCCTGGGCACCAAGAC
CTACACCTGCAACGTGGACCACAAGCCCTCCAACACCAAGGTGGACAAGCGGGTGGAGTCCAAGTACGGCCCCCCCTGCCCCTC
CTGCCCCGCCCCCGAGTTCCTGGGCGGCCCCTCCGTGTTCCTGTTCCCCCCCAAGCCCAAGGACACCCTGATGATCTCCCGGACCC
CCGAGGTGACCTGCGTGGTGGTGGACGTGTCCCAGGAGGACCCCGAGGTGCAGTTCAACTGGTACGTGGACGGCGTGGAGGTG
CACAACGCCAAGACCAAGCCCCGGGAGGAGCAGTTCAACTCCACCTACCGGGTGGTGTCCGTGCTGACCGTGCTGCACCAGGAC
TGGCTGAACGGCAAGGAGTACAAGTGCAAGGTGTCCAACAAGGGCCTGCCCTCCTCCATCGAGAAGACCATCTCCAAGGCCAAG
GGCCAGCCCCGGGAGCCCCAGGTGTACACCCTGCCCCCCTCCCAGGAGGAGATGACCAAGAACCAGGTGTCCCTGACCTGCCTG
GTGAAGGGCTTCTACCCCTCCGACATCGCCGTGGAGTGGGAGTCCAACGGCCAGCCCGAGAACAACTACAAGACCACCCCCCCC
GTGCTGGACTCCGACGGCTCCTTCTTCCTGTACTCCCGGCTGACCGTGGACAAGTCCCGGTGGCAGGAGGGCAACGTGTTCTCCT
GCTCCGTGATGCACGAGGCCCTGCACAACCACTACACCCAGAAGTCCCTGTCCCTGTCCCTGGGCAAGTGA

Figure 29

| Antibody | kon | koff | Kd |
| --- | --- | --- | --- |
| E71 | 2.67E+05 | 1.17E-03 | 7.36E-09 |
| chCE7 | 2.55E+05 | 1.57E-04 | 6.18E-10 |
| UJ127 | 6.77E+04 | 1.05E-05 | 1.55E-10 |
| 5G3 | 5.80E+04 | 1.50E-03 | 2.45E-08 |
| MAB777 | 1.68E+04 | 2.75E-04 | 1.64E-08 |
| 0.N.378 | 4.19E+04 | 6.29E-06 | 1.50E-10 |
| chE71-IgG1 | 2.27E+05 | 3.38E-03 | 1.49E-08 |
| chE71-IgG4 | 9.25E+04 | 1.41E-03 | 1.52E-08 |
| huE71-H1L1 | 2.21E+05 | 5.78E-04 | 2.57E-09 |
| huE71-H1L2 | 2.07E+05 | 1.07E-04 | 5.17E-10 |
| huE71-H2L1 | 1.98E+05 | 8.43E-04 | 4.26E-09 |
| huE71-H2L2 | 3.54E+05 | 9.63E-04 | 2.72E-09 |
| huE71-IgG1 | 2.27E+05 | 3.38E-03 | 1.49E-08 |
| huE71-IgG1n | 7.58E+04 | 2.94E-03 | 3.88E-08 |
| huE71-IgG4 | 9.25E+04 | 1.41E-03 | 1.52E-08 |

Figure 30

| Antibody | kon | koff | Kd |
|---|---|---|---|
| E71 | 2.44E+05 | 7.67E-05 | 3.14E-10 |
| E72-H1L1 | 2.06E+05 | 1.84E-05 | 8.93E-11 |
| E72-H1L2 | 1.17E+05 | 2.95E-05 | 2.52E-10 |
| E72-H2L1 | 2.40E+05 | 8.46E-05 | 3.53E-10 |
| E72-H2L2 | 2.11E+05 | 1.13E-04 | 5.36E-10 |
| chE72 | 1.65E+05 | 1.38E-04 | 8.36E-10 |
| chCE7 | 1.19E+05 | 1.69E-04 | 1.42E-09 |

Figure 31

| Antibody | kon | koff | Kd |
|---|---|---|---|
| E72-H1L1 | 3.15E+05 | 3.60E-05 | 1.14E-10 |
| E72-H1L2 | 1.79E+05 | 4.84E-05 | 2.70E-10 |
| E72-H2L1 | 3.07E+05 | 1.09E-04 | 3.55E-10 |
| E72-H2L2 | 2.10E+05 | 1.40E-04 | 6.67E-10 |
| chE72 | 3.26E+05 | 1.57E-04 | 4.82E-10 |
| chCE7 | 1.46E+05 | 1.90E-04 | 1.30E-09 |

Figure 32

| Mesothelioma | MOPC 21 | E71 |
|---|---|---|
| JMN | 5 | 29 |
| MESO 9 | 5 | 48 |
| MESO 10 | 5 | 40 |
| MESO 11 | 5 | 160 |
| MESO 34 | 5 | 565 |
| MESO 47 | 5 | 233 |
| MSTO | 5 | 28 |
| MSTO-21H | 5 | 5 |
| NCI-H2052 | 5 | 21 |
| VAMT | 5 | 103 |

Figure 33

| Tumor Type | Cell line name | Rituxan | huE71-IgG1n |
|---|---|---|---|
| ALL | 8402 | 4 | 4 |
| ALL | HPB-T | 5 | 4 |
| AML | THP-1 | 5 | 3 |
| AML | ACC 104 M-07e | 5 | 4 |
| breast CA | AU565 | 5 | 13 |
| breast CA | HTB24 | 6 | 71 |
| breast CA | HTB25 | 5 | 48 |
| breast CA | HCC1954 | 5 | 37 |
| breast CA | MCF7 | 5 | 79 |
| CRC | SW480 | 5 | 66 |
| EWS | CHP-100 | 5 | 19 |
| EWS | TC32 | 5 | 5 |
| EWS | SKERT | 5 | 272 |
| EWS | SKELP | 5 | 10 |
| EWS | 5838 | 5 | 18 |
| EWS | A4573 | 5 | 91 |
| EWS | SKES-1 | 5 | 87 |
| EWS | SKEAW | 5 | 5 |
| EWS | SKEPR | 3 | 1 |
| EWS | TC71 | 5 | 14 |
| EWS | SKEFM | 5 | 3 |
| EWS | SKNMC | 5 | 79 |

Figure 34

| Tumor Type | Cell line name | Rituxan | huE71-IgG1n |
|---|---|---|---|
| HNSCC | UM SCC 22B | 5 | 9 |
| melanoma | M14 | 5 | 13 |
| melanoma | SKMEL28 | 5 | 726 |
| melanoma | HTB67 | 5 | 6 |
| NB | SKNCM | 5 | 112 |
| NB | IMR32 LUC | 4 | 72 |
| NB | LAN-1 | 6 | 97 |
| NB | SKNMM LUC | 4 | 457 |
| osteosarcoma | RG143B | 5 | 20 |
| osteosarcoma | U2OS | 5 | 171 |
| osteosarcoma | CRL1427 | 5 | 6 |
| rhabdomyosarcoma | RH30 | 5 | 439 |
| rhabdomyosarcoma | RH41 | 5 | 127 |
| rhabdomyosarcoma | RH48 | 5 | 172 |
| rhabdomyosarcoma | HTB82 | 5 | 5 |
| rhabdomyosarcoma | RH28 | 5 | 199 |
| rhabdomyosarcoma | RH36 | 5 | 84 |
| SCLC | NCI-H82 | 5 | 15 |
| SCLC | NCI-H69 | 4 | 5 |
| SCLC | NCI-H345 | 3 | 6 |
| SCLC | NCI-H524 | 3 | 22 |
| submaxillary salivary gland | HTB-41 A253 | 5 | 31 |

Figure 36

| |
|---|
| Amino acid sequence of huE71-BsAb Heavy Chain (SEQ ID NO: 49)<br>QVQLVQPGDELVKPGASVKLSCKASGYTFTSYWMQWVKQRPGQGLEWIGEINPSNGRTN<br>YNEMFKSKAVLSVDKSVSTAYMQLSSLTAEDTAVYYCALYDGYYAMDYWGQGTLVTVS<br>SASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKRVEPKSCDKTHTCPPCPAPELLGGPSV<br>FLFPPKPKDTLMISRTPEVTCVVVDVSHEDPEVKFNWYVDGVEVHNAKTKPREEQYASTY<br>RVVSVLTVLHQDWLNGKEYKCAVSNKALPAPIEKTISKAKGQPREPQVYTLPPSRDELTKN<br>QVSLTCLVKGFYPSDIAVEWESNGQPENNYKTTPPVLDSDGSFFLYSKLTVDKSRWQQGN<br>VFSCSVMHEALHNHYTQKSLSLSPGK |
| Amino acid sequence of huE71-BsAb Light Chain - huOKT3scFv (SEQ ID NO: 50)<br>DIVMTQSPSSLAVSVGERVTMSCKSSQSLLYSSNQKNYLAWYQQKPGQSPKLLIYWASTR<br>ESGVPDRFSGSGSGTDFTLTISSVKAEDVALYYCQQYHSYPFTFGQGTKLEIKRTVAAPSVF<br>IFPPSDEQLKSGTASVVCLLNNFYPREAKVQWKVDNALQSGNSQESVTEQDSKDSTYSLSS<br>TLTLSKADYEKHKVYACEVTHQGLSSPVTKSFNRGECTS<u>GGGGSGGGGSGGGGS</u>QVQLV<br>QSGGGVVQPGRSLRLSCKASGYTFTRYTMHWVRQAPGKCLEWIGYINPSRGYTNYNQKF<br>KDRFTISRDNSKNTAFLQMDSLRPEDTGVYFCARYYDDHYSLDYWGQGTPVTVSS<u>GGGGS<br>GGGGSGGGGSGGGGSGGGGS</u>DIQMTQSPSSLSASVGDRVTITCSASSSVSYMNWY<br>QQTPGKAPKRWIYDTSKLASGVPSRFSGSGSGTDYTFTISSLQPEDIATYYCQQWSSNPFTF<br>GCGTKLQITR |
| Amino acid sequence of huE72-BsAb Heavy Chain (SEQ ID NO: 51)<br>QVQLVQPGAEVVKPGASVKLSCKASGYTFTGYWMHWVKQAPGQGLEWIGEINPSNGRTN<br>YNERFKSKATLTVDKSITTAFMELSRLRSDDTAVYFCARDYYGTSYNFDYWGQGTLLTVS<br>SASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKRVEPKSCDKTHTCPPCPAPELLGGPSV<br>FLFPPKPKDTLMISRTPEVTCVVVDVSHEDPEVKFNWYVDGVEVHNAKTKPREEQYASTY<br>RVVSVLTVLHQDWLNGKEYKCAVSNKALPAPIEKTISKAKGQPREPQVYTLPPSRDELTKN<br>QVSLTCLVKGFYPSDIAVEWESNGQPENNYKTTPPVLDSDGSFFLYSKLTVDKSRWQQGN<br>VFSCSVMHEALHNHYTQKSLSLSPGK |
| Amino acid sequence of huE72-BsAb Light Chain - huOKT3scFv (SEQ ID NO: 52)<br>DIQMTQSPSSLSVSVGDRVTITCKANEDINNRLAWYQQKPGKAPKLLISGATNLVTGVPSR<br>FSGSGSGTDYTLTISSLQPEDFATYYCQQYWSTPFTFGQGTELEIKRTVAAPSVFIFPPSDEQ<br>LKSGTASVVCLLNNFYPREAKVQWKVDNALQSGNSQESVTEQDSKDSTYSLSSTLTLSKA<br>DYEKHKVYACEVTHQGLSSPVTKSFNRGECTS<u>GGGGSGGGGSGGGGS</u>QVQLVQSGGGVV<br>QPGRSLRLSCKASGYTFTRYTMHWVRQAPGKCLEWIGYINPSRGYTNYNQKFKDRFTISR<br>DNSKNTAFLQMDSLRPEDTGVYFCARYYDDHYSLDYWGQGTPVTVSS<u>GGGGSGGGGSGG<br>GGSGGGGSGGGGS</u>DIQMTQSPSSLSASVGDRVTITCSASSSVSYMNWYQQTPGKA<br>PKRWIYDTSKLASGVPSRFSGSGSGTDYTFTISSLQPEDIATYYCQQWSSNPFTFGCGTKLQI<br>TR |

Figure 37

|  | $k_{on}$ (1/Ms) | $k_{off}$ (1/s) | $K_D = k_{off}/k_{on}$ (M) |
|---|---|---|---|
| mouse E71-IgG1 | 8.93E+04 | 1.99E-04 | 2.23E-09 |
| huE71-IgG1 | 7.03E+04 | 3.25E-04 | 4.62E-09 |
| huE71-BsAb | 6.58E+04 | 3.39E-04 | 5.15E-09 |
| chimeric E72-IgG1 | 1.97E+05 | 1.24E-04 | 6.29E-10 |
| huE72-IgG1 | 7.40E+04 | 1.39E-04 | 1.88E-09 |
| huE72-BsAb | 3.58E+04 | 1.89E-04 | 5.28E-09 |

Figure 41

| Tumor type | Cell line | L1CAM expression (MFI) | huE71-BsAb EC50 (pM) | huE72-BsAb EC50 (pM) |
|---|---|---|---|---|
| neuroblastoma | NB1691 | 742 | 31 | 31 |
| neuroblastoma | BE(1)N | 614 | 16 | 14 |
| neuroblastoma | BE(2)C | 608 | 50 | 50 |
| neuroblastoma | SKNMM LUC | 598 | 94 | 71 |
| neuroblastoma | IMR32 LUC | 285 | 62 | 50 |
| neuroblastoma | NMB7 | 224 | 56 | 46 |
| neuroblastoma | BE(2)S | 166 | 251 | 251 |
| neuroblastoma | SKNSH | 23 | 158 | 158 |
| melanoma | SKMEL5 | 269 | 20 | 27 |
| melanoma | SKMEL28 | 184 | 150 | 140 |
| breast CA | HTB24 | 431 | 56 | 27 |
| breast CA | HTB26 | 33 | 56 | 56 |
| breast CA | MCF7 | 54 | 158 | 100 |

Figure 47

| Antibody | HuE71-1 MAGE | HuE71-1 | HuE71-1 Aglyco | HuE71-4 | HuE71-4M | Ctrl-4 |
|---|---|---|---|---|---|---|
| Target | L1CAM | L1CAM | L1CAM | L1CAM | L1CAM | GD2 (non-specific) |
| Subclass | IgG1 | IgG1 | IgG1 | IgG4 | IgG4 | IgG4 |
| Modification | Defucosylated Fc region | Wildtype | Aglycosylated Fc region | Wildtype | Hinge region mutation | Wildtype |
| FcγR Binding | ++ | + | - | - | - | - |
| Fab Arm Exchange | - | - | - | + | - | + |

Figure 55

| | HuE71-1 MAGE | | HuE71-1 MAGE Blocked | | HuE71-1 WT | | HuE71-1 WT Blocked | | HuE71-1 Aglyco | | HuE71-1 Aglyco Blocked | |
|---|---|---|---|---|---|---|---|---|---|---|---|---|
| | %ID/g | SEM | %ID/g | SEM | %ID/g | SEM | %ID/g | SEM | %ID/g | SEM | %ID/g | SEM |
| Blood | 4.67 | 0.85 | 9.84 | 0.84 | 5.52 | 0.99 | 9.64 | 1.39 | 7.94 | 1.19 | 9.51 | 0.39 |
| Tumor | 16.15 | 0.85 | 5.87 | 0.76 | 19.68 | 1.00 | 6.82 | 0.81 | 32.03 | 2.99 | 10.59 | 1.52 |
| Heart | 4.60 | 0.77 | 9.55 | 0.53 | 4.56 | 0.44 | 7.80 | 1.57 | 3.76 | 0.59 | 6.25 | 1.33 |
| Lungs | 4.81 | 1.16 | 7.95 | 1.00 | 5.63 | 0.97 | 6.67 | 1.20 | 4.86 | 1.13 | 5.10 | 1.08 |
| Liver | 7.09 | 0.69 | 9.24 | 0.64 | 11.06 | 1.00 | 13.65 | 1.16 | 6.22 | 1.22 | 9.76 | 0.37 |
| Spleen | 7.13 | 1.12 | 9.08 | 0.84 | 8.15 | 1.93 | 7.52 | 1.32 | 4.37 | 0.56 | 4.49 | 0.24 |
| Stomach | 2.52 | 0.51 | 3.68 | 0.77 | 3.66 | 0.29 | 3.96 | 0.88 | 3.56 | 0.51 | 3.78 | 0.40 |
| Large Bowel | 2.20 | 0.21 | 2.37 | 0.51 | 2.06 | 0.14 | 2.77 | 0.93 | 2.56 | 0.31 | 3.31 | 0.30 |
| Small Bowel | 3.05 | 0.85 | 4.02 | 1.30 | 3.40 | 0.56 | 2.09 | 0.95 | 3.63 | 0.31 | 4.23 | 1.45 |
| Pancreas | 4.63 | 0.84 | 4.47 | 0.33 | 3.92 | 0.77 | 4.09 | 1.21 | 4.28 | 0.69 | 4.73 | 1.81 |
| Ovary | 3.36 | 0.50 | 5.72 | 2.14 | 4.78 | 0.61 | 5.07 | 1.71 | 3.49 | 0.90 | 5.97 | 2.30 |
| Kidney | 6.17 | 1.00 | 9.97 | 0.49 | 5.92 | 0.80 | 7.23 | 1.55 | 4.62 | 0.70 | 6.12 | 0.79 |
| Bone | 2.85 | 0.99 | 3.69 | 0.50 | 2.87 | 0.17 | 3.06 | 0.63 | 2.79 | 0.85 | 3.64 | 1.42 |
| Muscle | 3.78 | 0.60 | 4.26 | 0.97 | 4.14 | 0.48 | 4.97 | 0.75 | 4.87 | 0.85 | 6.31 | 0.98 |
| Lymph | 17.16 | 0.41 | 18.63 | 0.95 | 16.86 | 1.39 | 19.21 | 0.66 | 5.60 | 0.49 | 5.71 | 1.65 |
| Skin | 1.49 | 0.38 | 3.77 | 1.52 | 1.79 | 0.57 | 4.14 | 0.62 | 2.66 | 0.78 | 3.87 | 0.45 |
| Tail | 1.57 | 0.42 | 5.20 | 0.50 | 2.54 | 1.09 | 4.22 | 0.82 | 2.39 | 0.75 | 4.21 | 1.08 |

Figure 57

| | HuE71-4 WT | | HuE71-4 WT Blocked | | HuE71-4 Mutant | | HuE71-4 Mutant Blocked | | HuCtrl-4 WT | |
|---|---|---|---|---|---|---|---|---|---|---|
| | %ID/g | SEM | %ID/g | SEM | %ID/g | SEM | %ID/g | SEM | %ID/g | SEM |
| Blood | 3.53 | 0.63 | 5.88 | 1.24 | 5.86 | 0.18 | 7.35 | 0.15 | 7.32 | 0.49 |
| Tumor | 27.30 | 1.55 | 10.65 | 0.47 | 16.90 | 1.22 | 9.04 | 1.42 | 6.03 | 0.87 |
| Heart | 2.76 | 0.25 | 3.37 | 1.03 | 5.34 | 0.79 | 7.90 | 0.72 | 7.05 | 0.93 |
| Lungs | 3.65 | 0.93 | 4.76 | 0.66 | 5.39 | 0.46 | 6.37 | 0.92 | 5.86 | 0.45 |
| Liver | 3.85 | 0.52 | 5.25 | 0.50 | 13.20 | 0.70 | 13.97 | 1.04 | 11.05 | 0.50 |
| Spleen | 5.44 | 1.28 | 5.76 | 0.96 | 9.23 | 1.27 | 9.58 | 0.48 | 9.63 | 1.54 |
| Stomach | 4.58 | 0.28 | 5.01 | 1.07 | 3.81 | 1.49 | 4.35 | 0.49 | 5.01 | 0.54 |
| Large Bowel | 2.39 | 0.62 | 2.64 | 0.36 | 3.95 | 1.05 | 3.84 | 0.49 | 3.52 | 0.28 |
| Small Bowel | 2.26 | 0.44 | 2.75 | 0.46 | 3.64 | 0.67 | 3.46 | 1.45 | 3.10 | 0.65 |
| Pancreas | 3.11 | 0.56 | 3.46 | 0.36 | 5.73 | 0.22 | 5.42 | 0.71 | 3.26 | 0.50 |
| Ovary | 3.31 | 0.86 | 3.80 | 0.31 | 3.95 | 0.78 | 3.30 | 0.62 | 2.99 | 1.18 |
| Kidney | 12.06 | 1.24 | 14.96 | 0.94 | 5.83 | 0.54 | 6.04 | 0.27 | 17.91 | 2.46 |
| Bone | 1.48 | 0.30 | 1.80 | 0.53 | 2.72 | 0.56 | 3.84 | 1.34 | 3.71 | 1.35 |
| Muscle | 3.53 | 0.24 | 4.15 | 0.62 | 2.67 | 1.21 | 3.67 | 1.23 | 4.03 | 0.67 |
| Lymph | 3.99 | 0.97 | 3.15 | 1.03 | 2.95 | 0.44 | 4.23 | 0.56 | 4.90 | 0.41 |
| Skin | 2.98 | 0.87 | 2.80 | 0.31 | 3.70 | 0.98 | 3.22 | 1.11 | 3.44 | 0.79 |
| Tail | 1.50 | 0.15 | 1.88 | 0.18 | 3.30 | 0.82 | 4.57 | 1.08 | 2.89 | 0.79 |

ADCC assay
Target cells: LAN-1 cells

ANTI-L1-CAM ANTIBODIES AND USES THEREOF

CROSS-REFERENCE TO RELATED APPLICATIONS

This application is a National Stage Application of PCT/US2018/037645, filed Jun. 14, 2018, which claims the benefit of and priority to U.S. Provisional Appl. No. 62/520,382, filed Jun. 15, 2017, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 14, 2018, is named 115872-0375_SL.txt and is 147,283 bytes in size.

TECHNICAL FIELD

The present technology relates generally to the preparation of immunoglobulin-related compositions (e.g., antibodies or antigen binding fragments thereof) that specifically bind L1-CAM protein and uses of the same. In particular, the present technology relates to the preparation of L1-CAM neutralizing antibodies and their use in detecting and treating L1-CAM associated cancers.

BACKGROUND

The following description of the background of the present technology is provided simply as an aid in understanding the present technology and is not admitted to describe or constitute prior art to the present technology.

The advent of chimeric antigen receptor (CAR) technology (Sadelain M et al., *Cancer Discov* 3:388-98 (2013)) is rapidly expanding the therapeutic investigations of anti-L1-CAM redirected gene-modified T cells, with several clinical trials using L1-CAM-CAR modified T cells: NCT00889954 (all L1-CAM(+) cancers), NCT01935843 (L1-CAM(+) solid tumors). See Hong H et al., *J Immunother* 37:93-104 (2014). While T cells can effectively target tumors having low levels of L1-CAM, there are concerns regarding potential bystander toxicity in normal tissues that have low levels of L1-CAM expression.

Apart from toxicity, cell harvesting, processing, storage, transport and product release regulations for lymphocyte therapy can be challenging, especially when the cells have to be genetically modified. T cell exhaustion, survival and homing are suboptimal despite the infusion of billions of these cells. Further, CAR-modified T cells are no exception to the immunosuppressive tumor microenvironment, where Tregs, tumor associated macrophages and myeloid suppressor cells work in concert to circumvent the anti-tumor properties of CAR modified T-cells. Furthermore, CAR modified T-cells are subject to the same immunosuppressive constraints confronted by classic T-cells, including anergy following engagement of CTLA4 by B7 or PD-1 by PD-L1 (B7-H1) on tumor cells. Clinically effective alternatives to CAR modified T-cell therapy for the treatment of cancer are thus warranted.

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of GYTFTSYWMQ (SEQ ID NO: 53), a $V_H$—CDR2 sequence of EINPSNGRTNYNEMFKS (SEQ ID NO: 54), and a $V_H$-CDR3 sequence of YDGYYAMDY (SEQ ID NO: 55); and/or; (b) the $V_L$ comprises a $V_L$-CDR1 sequence of KSSQSLLYSSNQKNYLA (SEQ ID NO: 56), a $V_L$—CDR2 sequence of WASTRES (SEQ ID NO: 57), and a $V_L$-CDR3 sequence of QQYHSYPFT (SEQ ID NO: 58). In some embodiments of the antibody or antigen binding fragment, the $V_H$ comprises the amino acid sequence of SEQ ID NO: 1 and the $V_L$ comprises amino acid sequence of SEQ ID NO: 3. Additionally or alternatively, the antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, F(ab')$_2$, Fab', scF$_v$, and F$_v$. In some embodiments, the antibody is a monoclonal antibody, chimeric antibody, humanized antibody, or a bispecific antibody. In certain embodiments, the antibody or antigen binding fragment binds to an epitope of L1-CAM protein comprising at least five to eight consecutive amino acid residues of the 2nd Ig-like domain of L1-CAM (SEQ ID NO: 74). In some embodiments, the epitope is a conformational epitope.

In another aspect, the present disclosure provides an antibody comprising a heavy chain (HC) amino acid sequence of SEQ ID NO: 9, SEQ ID NO: 10, SEQ ID NO: 17, SEQ ID NO: 18, SEQ ID NO: 26, SEQ ID NO: 30, SEQ ID NO: 42, SEQ ID NO: 46, SEQ ID NO: 49, SEQ ID NO: 51, or a variant thereof having one or more conservative amino acid substitutions, and/or a light chain (LC) amino acid sequence of SEQ ID NO: 13, SEQ ID NO: 14, SEQ ID NO: 21, SEQ ID NO: 22, SEQ ID NO: 25, SEQ ID NO: 29, SEQ ID NO: 41, SEQ ID NO: 45, SEQ ID NO: 50, SEQ ID NO: 52, or a variant thereof having one or more conservative amino acid substitutions. In certain embodiments, the antibody comprises a HC amino acid sequence and a LC amino acid sequence selected from the group consisting of: SEQ ID NO: 9 and SEQ ID NO: 13 (huE71 H1/L1); SEQ ID NO: 9 and SEQ ID NO: 14 (huE71 H1/L2); SEQ ID NO: 10 and SEQ ID NO: 13 (huE71 H2/L1); SEQ ID NO: 10 and SEQ ID NO: 14 (huE71 H2/L2); SEQ ID NO: 17 and SEQ ID NO: 21 (huE72 H1/L1); SEQ ID NO: 17 and SEQ ID NO: 22 (huE72 H1/L2); SEQ ID NO: 18 and SEQ ID NO: 21 (huE72 H2/L1); SEQ ID NO: 18 and SEQ ID NO: 22 (huE72 H2/L2); SEQ ID NO: 26 and SEQ ID NO: 25 (chE71IgG1); SEQ ID NO: 30 and SEQ ID NO: 29 (chE72 IgG1); SEQ ID NO: 42 and SEQ ID NO: 41 (chE71IgG4); SEQ ID NO: 46 and SEQ ID NO: 45 (huE71IgG4); SEQ ID NO: 49 and SEQ ID NO: 50 (huE71 BsAb); and SEQ ID NO: 51 and SEQ ID NO: 52 (huE72 BsAb).

In one aspect, the present disclosure provides an antibody comprising (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 13, 14, 21, 22, 25, 29, 41, 45, 50 or 52; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 9, 10, 17, 18, 26, 30, 42, 46, 49, and 51.

In another aspect, the present disclosure provides an antibody comprising (a) a LC sequence that is at least 80%, at least 85%, at least 90%, at least 95%, or at least 99% identical to the LC sequence present in any one of SEQ ID NOs: 13, 14, 21, 22, 25, 29, 41, 45, 50 or 52; and/or (b) a HC sequence that is at least 80%, at least 85%, at least 90%, at least 95%, or at least 99% identical to the HC sequence present in any one of SEQ ID NOs: 9, 10, 17, 18, 26, 30, 42, 46, 49, and 51.

In any of the above embodiments, the antibody is a chimeric antibody, a humanized antibody, or a bispecific antibody. Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody binds to an epitope of L1-CAM protein comprising at least five to eight consecutive amino acid residues of the 2nd Ig-like domain of L1-CAM (SEQ ID NO: 74) or the 6th Ig-like domain of L1-CAM (SEQ ID NO: 75). In some embodiments, the epitope is a conformational epitope. Additionally or alternatively, in some embodiments, the antibody of the present technology lacks α-1,6-fucose modifications.

In one aspect, the present disclosure provides a recombinant nucleic acid sequence encoding any of the antibodies described herein. In some embodiments, the recombinant nucleic acid sequence selected from the group consisting of: SEQ ID NOs: 11, 12, 15, 16, 19, 20, 23, 24, 27, 28, 31, 32, 43, 44, 47 and 48.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In some embodiments of the bispecific antibody of the present technology, the bispecific antibody binds to T cells, B-cells, myeloid cells, plasma cells, or mast-cells. Additionally or alternatively, in some embodiments, the bispecific antibody binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys(HSG)-D-Tyr-Lys(HSG)-NH$_2$, Ac-Lys(HSG)D-Tyr-Lys(HSG)-Lys(Tscg-Cys)-NH$_2$, DOTA-D-Asp-D-Lys(HSG)-D-Asp-D-Lys(HSG)-NH$_2$; DOTA-D-Glu-D-Lys(HSG)-D-Glu-D-Lys(HSG)-NH$_2$, DOTA-D-Tyr-D-Lys(HSG)-D-Glu-D-Lys(HSG)-NH$_2$, DOTA-D-Ala-D-Lys(HSG)-D-Glu-D-Lys(HSG)-NH$_2$, DOTA-D-Phe-D-Lys(HSG)-D-Tyr-D-Lys(HSG)-NH$_2$, Ac-D-Phe-D-Lys(DOTA)-D-Tyr-D-Lys(DOTA)-NH$_2$, Ac-D-Phe-D-Lys(DTPA)-D-Tyr-D-Lys(DTPA)-NH$_2$, Ac-D-Phe-D-Lys(Bz-DTPA)-D-Tyr-D-Lys(Bz-DTPA)-NH$_2$, Ac-D-Lys(HSG)-D-Tyr-D-Lys(HSG)-D-Lys(Tscg-Cys)-NH$_2$, DOTA-D-Phe-D-Lys(HSG)-D-Tyr-D-Lys(HSG)-D-Lys(Tscg-Cys)-NH$_2$, (Tscg-Cys)-D-Phe-D-Lys(HSG)-D-Tyr-D-Lys(HSG)-D-Lys(DOTA)-NH$_2$, Tscg-D-Cys-D-Glu-D-Lys(HSG)-D-Glu-D-Lys(HSG)-NH$_2$, (Tscg-Cys)-D-Glu-D-Lys(HSG)-D-Glu-D-Lys(HSG)-NH$_2$, Ac-D-Cys-D-Lys(DOTA)-D-Tyr-D-Ala-D-Lys(DOTA)-D-Cys-NH$_2$, Ac-D-Cys-D-Lys(DTPA)-D-Tyr-D-Lys(DTPA)-NH$_2$, Ac-D-Lys(DTPA)-D-Tyr-D-Lys(DTPA)-D-Lys(Tscg-Cys)-NH$_2$, and Ac-D-Lys(DOTA)-D-Tyr-D-Lys(DOTA)-D-Lys(Tscg-Cys)-NH$_2$.

In another aspect, the present disclosure provides a method for treating a L1-CAM associated cancer in a subject in need thereof, comprising administering to the subject an effective amount of any one of the antibodies disclosed herein. In certain embodiments, the antibody comprises a HC amino acid sequence and a LC amino acid sequence selected from the group consisting of: (i) SEQ ID NO: 9 and SEQ ID NO: 13 (huE71 H1/L1); (ii) SEQ ID NO: 9 and SEQ ID NO: 14 (huE71 H1/L2); (iii) SEQ ID NO: 10 and SEQ ID NO: 13 (huE71 H2/L1); (iv) SEQ ID NO: 10 and SEQ ID NO: 14 (huE71 H2/L2); (v) SEQ ID NO: 17 and SEQ ID NO: 21 (huE72 H1/L1); (vi) SEQ ID NO: 17 and SEQ ID NO: 22 (huE72 H1/L2); (vii) SEQ ID NO: 18 and SEQ ID NO: 21 (huE72 H2/L1); (viii) SEQ ID NO: 18 and SEQ ID NO: 22 (huE72 H2/L2); (ix) SEQ ID NO: 26 and SEQ ID NO: 25 (chE71IgG1); (x) SEQ ID NO: 30 and SEQ ID NO: 29 (chE72 IgG1); (xi) SEQ ID NO: 42 and SEQ ID NO: 41 (chE71IgG4); (xii) SEQ ID NO: 46 and SEQ ID NO: 45 (huE71IgG4); (xiii) SEQ ID NO: 49 and SEQ ID NO: 50 (huE71 BsAb); and (xiv) SEQ ID NO: 51 and SEQ ID NO: 52 (huE72 BsAb), wherein the antibody specifically binds to and neutralizes L1-CAM activity.

In some embodiments, the L1-CAM associated cancer is leukemia, Ewing's sarcoma, neuroblastoma, osteosarcoma, glioblastoma multiforme, ovarian cancer, endometrial cancer, uterine cancer, triple negative breast cancer, melanoma, clear cell renal cell cancer, pheochromacytoma and paraganglioma, mesothelioma, small cell lung cancer (SCLC), non-small cell lung cancer, NSCLC, pancreatic ductal cancer, colon cancer, pancreatic cancer, hepatocellular carcinoma, gastric cancer, cholangiocarcinoma, carcinoid, neuroendocrine tumors, gastrointestinal stromal tumor (GIST), pheochromocytoma, glioma, pancreatic neuroectodermal cancer, pancreatic adenocarcinoma, colorectal cancer, renal cell carcinoma, tumor blood vessels, chondrosarcoma, esophageal adenocarcinoma, oligodendroglioma, astrocytoma, ependymoma, pancreatic neuroendocrine carcinoma, adrenal adenoma, leiomyosarcoma, liposarcoma, granular cell tumor of the ovary, schwannoma, primitive neuroectodermal tumor (PNET), epitheliod sarcoma, esthesioneuroblastoma, medulloblastoma, capillary hemangioma, Kaposi sarcoma, rhabdomyosarcoma, submaxillary salivary gland cancer, or head and neck squamous cell carcinoma.

Additionally or alternatively, in some embodiments of the method, the antibody is administered to the subject separately, sequentially or simultaneously with an additional therapeutic agent. Examples of additional therapeutic agents include one or more of alkylating agents, platinum agents, taxanes, *vinca* agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents.

In another aspect, the present disclosure provides a method for detecting a tumor in a subject in vivo comprising (a) administering to the subject an effective amount of an antibody of the present technology, wherein the antibody is configured to localize to a tumor expressing L1-CAM and is labeled with a radioisotope; and (b) detecting the presence of a tumor in the subject by detecting radioactive levels emitted by the antibody that are higher than a reference value. In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of L1-CAM associated cancers, comprising at least one immunoglobulin-related composition of the present technology (e.g., any antibody or antigen binding fragment described herein, or a functional variant (e.g., substitutional variant) thereof. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-L1-CAM immunoglobulin-related composition described herein. In some embodiments, the secondary antibody is coupled to at least one detectable label selected from the group consisting of a radioactive label, a fluorescent label, or a chromogenic label.

BRIEF DESCRIPTION OF THE DRAWINGS

FIG. 4 shows the expression of L1-CAM among human tumors (adapted from Rawnaq T et al., *J Surg Res* 173:314-9 (2012).
FIG. 6 shows the amino acid sequences of the heavy-chain variable domain ($V_H$) and light-chain variable domain ($V_L$) of the murine antibody E71 and their homologous human sequences (SEQ ID NOs: 1-4). The CDRs of the heavy and light chains of murine E71 and their homologous human sequences are underlined.
FIG. 7 shows the amino acid sequences of the $V_H$ and $V_L$ of the murine antibody E72 and their homologous human sequences (SEQ ID NOs: 5-8). The CDRs of the heavy and light chains of murine E72 and their homologous human sequences are underlined. The $V_H$ CDR1, $V_H$ CDR2, and $V_H$ CDR3 amino acid sequences of E72 are GYWMH (SEQ ID NO: 68), EINPSNGRTNYNERFKS (SEQ ID NO: 69) and DYYGTSYNFDY (SEQ ID NO: 70) respectively and the $V_L$ CDR1, $V_L$ CDR2, and $V_L$ CDR3 amino acid sequences of E72 are KANEDINNRLA (SEQ ID NO: 71), GATNLVT (SEQ ID NO: 72), and QQYWSTPFT (SEQ ID NO: 73) respectively.
FIG. 8 shows the amino acid sequences of the humanized heavy chains of E71 (SEQ ID NOs: 9-10).
FIG. 9 shows the cDNA sequences of the humanized heavy chains of E71 (SEQ ID NOs: 11-12).
FIG. 10 shows the amino acid sequences of the humanized light chains of E71 (SEQ ID NOs: 13-14).
FIG. 11 shows the cDNA sequences of the humanized light chains of E71 (SEQ ID NOs: 15-16).
FIG. 12 shows the amino acid sequences of the humanized heavy chains of E72 (SEQ ID NOs: 17-18).
FIG. 13 shows the cDNA sequences of the humanized heavy chains of E72 (SEQ ID NOs: 19-20).
FIG. 14 shows the amino acid sequences of the humanized light chains of E72 (SEQ ID NOs: 21-22).
FIG. 15 shows the cDNA sequences of the humanized light chains of E72 (SEQ ID NOs: 23-24).
FIG. 16 shows the amino acid sequences of the heavy chain and light chain of chimeric chE71 (SEQ ID NOs: 25-26).
FIG. 17 shows the cDNA sequences of the heavy chain and light chain of chimeric chE71 (SEQ ID NOs: 27-28).
FIG. 18 shows the amino acid sequences of the heavy chain and light chain of chimeric chE72 (SEQ ID NOs: 29-30).
FIG. 19 shows the cDNA sequences of the heavy chain and light chain of chimeric chE72 (SEQ ID NOs: 31-32).
FIG. 20 shows the amino acid and cDNA sequences of the heavy chain of huE71 (SEQ ID NOs: 33-34).
FIG. 21 shows the amino acid and cDNA sequences of the light chain of huE71 (SEQ ID NOs: 35-36).
FIG. 22 shows the amino acid and cDNA sequences of the heavy chain of huE72 (SEQ ID NOs: 37-38).
FIG. 23 shows the amino acid and cDNA sequences of the light chain of huE72 (SEQ ID NOs: 39-40).
FIG. 24 shows the amino acid sequences of the heavy chain and light chain of chimeric IgG4, chE71-IgG4 (SEQ ID NOs: 41-42).
FIG. 25 shows the cDNA sequences of the heavy chain and light chain of chimeric IgG4, chE71-IgG4 (SEQ ID NOs: 43-44).
FIG. 26 shows the amino acid sequences of the heavy chain and light chain of humanized IgG4, huE71-IgG4 (SEQ ID NOs: 45-46).
FIG. 27 shows the cDNA sequences of the heavy chain and light chain of humanized IgG4, huE71-IgG4 (SEQ ID NOs: 47-48).
FIG. 29 shows the binding kinetics of the humanized IgG variants of huE71 assayed on L1-CAM-Fc using SPR (Biacore T100).
FIG. 30 shows the binding kinetics of the humanized IgG variants of huE72 assayed on L1-CAM-Fc using SPR (Biacore T100).
FIG. 31 shows the binding kinetics of the humanized IgG variants of huE72 assayed on L1-CAM-His using SPR (Biacore T100).
FIG. 32 shows the cell surface staining of mesothelioma cell lines by flow cytometry using mouse E71 and MOPC21 as control.
FIG. 33 shows the cell surface staining of leukemia, breast cancer and Ewings sarcoma cell lines by flow cytometry using humanized huE71-IgGn and Rituxan as control.

FIG. 34 shows the cell surface staining of melanoma, neuroblastoma, osteosarcoma, rhabdomyosarcoma, small cell lung cancer (SCLC) and head and neck cancer by flow cytometry using humanized huE71-IgGn and Rituxan as control.

FIG. 36 shows the amino acid sequences ($V_H$ and $V_L$) of T-cell engaging bispecific antibodies (BsAb) huE71-BsAb and huE72-BsAb (SEQ ID NOs: 49-52).

FIG. 37 shows the binding kinetics of humanized huE71 or huE72 IgGs and their BsAbs on L1-CAM-Fc using SPR (Biacore T100).

FIG. 41 shows the cytotoxicity (EC50) of humanized E71-BsAb or humanized E72-BsAb, and L1-CAM expression of tumor cell lines (Mean Fluorescence Index or MFI).

FIG. 47 shows a summary table of the characteristics of the humanized anti-L1-CAM antibodies of the present technology.

FIG. 55 shows the ex vivo biodistribution values of IgG1 antibodies 96 hours post-injection.

FIG. 57 shows the ex vivo biodistribution values of IgG4 antibodies 96 hours post-injection.

FIG. 59(A): SPECT-CT image of athymic nude SKOV-3 tumor bearing mouse 168 hours post-injection of $^{177}$Lu-HuE71-1 Aglyco (858 µCi in 150 µL of PBS). FIG. 59(B): Cerenkov image of athymic nude SKOV-3 tumor bearing mouse 168 hours post-injection of $^{177}$Lu-HuE71-1 Aglyco (858 µCi in 150 µL of PBS). FIG. 59(C): Ex vivo biodistribution of athymic nude SKOV-3 tumor bearing mouse 168 hours post-injection of $^{177}$Lu-HuE71-1 Aglyco (18-26 µCi in 150 µL of PBS, n=4).

DETAILED DESCRIPTION

Figure 1:
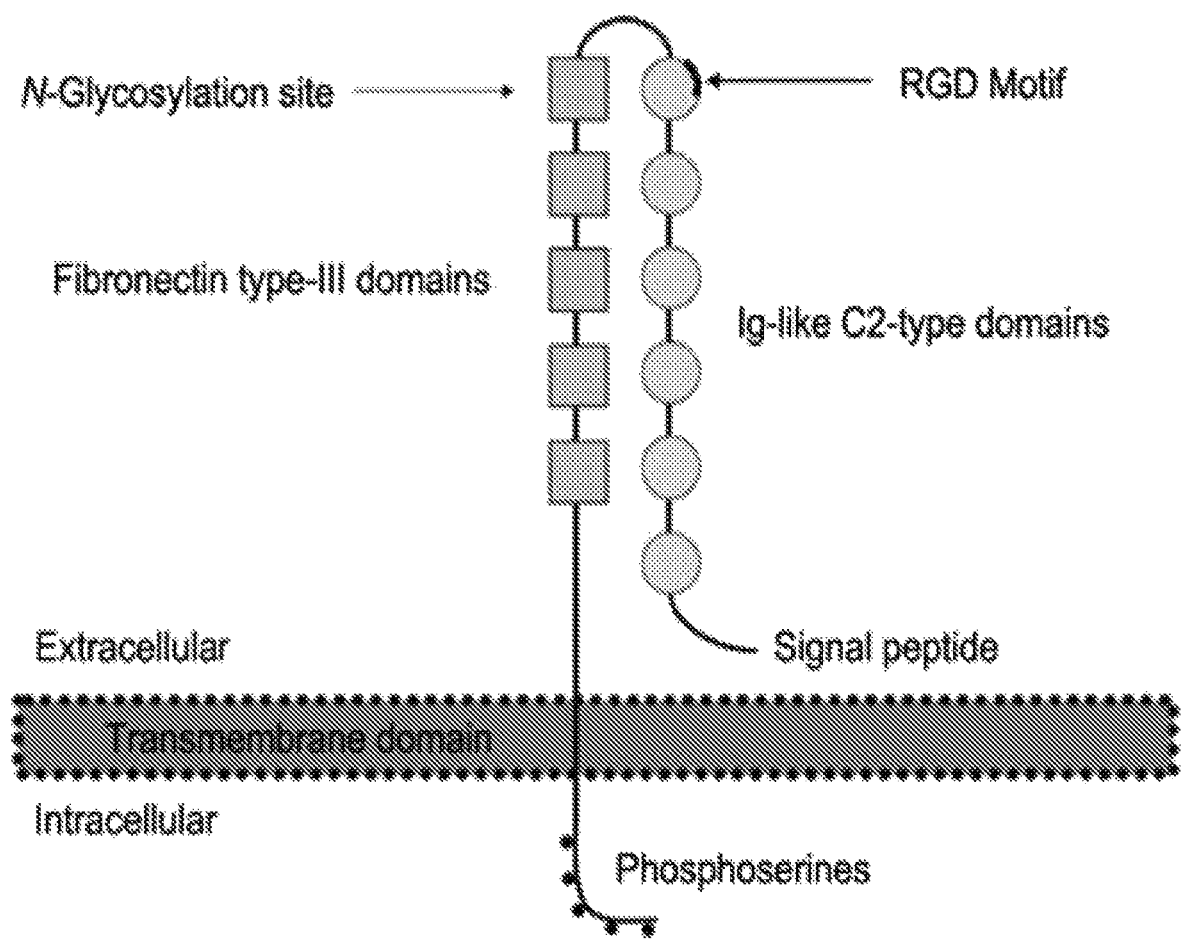
FIG. 1 shows the molecular structure of human L1-CAM.

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to and neutralize the biological activity of L1-CAM polypeptides. The immunoglobulin-related compositions of the present technology are useful in methods for detecting or treating L1-CAM associated cancers in a subject in need thereof. Accordingly, the various aspects of the present methods relate to the preparation, characterization, and manipulation of anti-L1-CAM antibodies. The immunoglobulin-related compositions of the present technology are useful alone or in combination with additional therapeutic agents for treating cancer. In some embodiments, the immunoglobulin-related composition is a humanized antibody, a chimeric antibody, or a bispecific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, 3$^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds L1-CAM protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof.

Examples of antibody fragments or antigen binding fragments include Fab, Fab', F(ab')$_2$, and Fv fragments; diabodies; linear antibodies; single-chain antibody molecules; and multispecific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., *Proc. Natl. Acad. Sci. USA*, 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scF$_v$)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a L1-CAM polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a breast, lung, colon, or prostate tissue sample obtained by needle biopsy.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl.*

*Acad. Sci. USA* 84: 214-218, 1987; Nishimura et al., *Cancer Res* 47: 999-1005, 1987; Wood et al., Nature 314: 446-449, 1885; and Shaw et al., *J. Natl. Cancer Inst.* 80: 1553-1559, 1988.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. In some embodiments, an "epitope" of the L1-CAM protein is a region of the protein to which the anti-L1-CAM antibodies of the present technology specifically bind. In some embodiments, the epitope is a conformational epitope. To screen for anti-L1-CAM antibodies which bind to an epitope, a routine cross-blocking assay such as that described in Antibodies, A Laboratory Manual, Cold Spring Harbor Laboratory, Ed Harlow and David Lane (1988), can be performed. This assay can be used to determine if an anti-L1-CAM antibody binds the same site or epitope as an anti-L1-CAM antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of L1-CAM protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., Nature 321: 522-525 (1986); Reichmann et al., Nature 332:323-329 (1988); and Presta, Curr. Op. Struct. Biol. 2:593-596 (1992). See e.g., Ahmed & Cheung, FEBS Letters 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region) as measured using a BLAST or BLAST 2.0 sequence comparison algorithms with default parameters described below, or by manual alignment and visual inspection, e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., Nature 256:495 (1975), or may be made by recombinant DNA methods (See, e.g., U.S. Pat. No. 4,816, 567). The "monoclonal antibodies" may also be isolated from phage antibody libraries using the techniques described in Clackson et al., Nature 352:624-628 (1991) and Marks et al., J. Mol. Biol. 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20th edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_d$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a L1-CAM polypeptide), or an epitope on a particular polypeptide, without substantially binding to any other polypeptide, or polypeptide epitope.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-L1-CAM antibodies described herein are contemplated. For example, it may be desirable to improve the binding affinity and/or other biological properties of the antibody. Amino acid sequence variants of an anti-L1-CAM antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

Amino Acid Substitutions

| Original Residue | Exemplary Substitutions | Conservative Substitutions |
|---|---|---|
| Ala (A) | val; leu; ile | val |
| Arg (R) | lys; gln; asn | lys |

TABLE 1-continued

Amino Acid Substitutions

| Original Residue | Exemplary Substitutions | Conservative Substitutions |
| --- | --- | --- |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

L1-CAM

Figure 2:
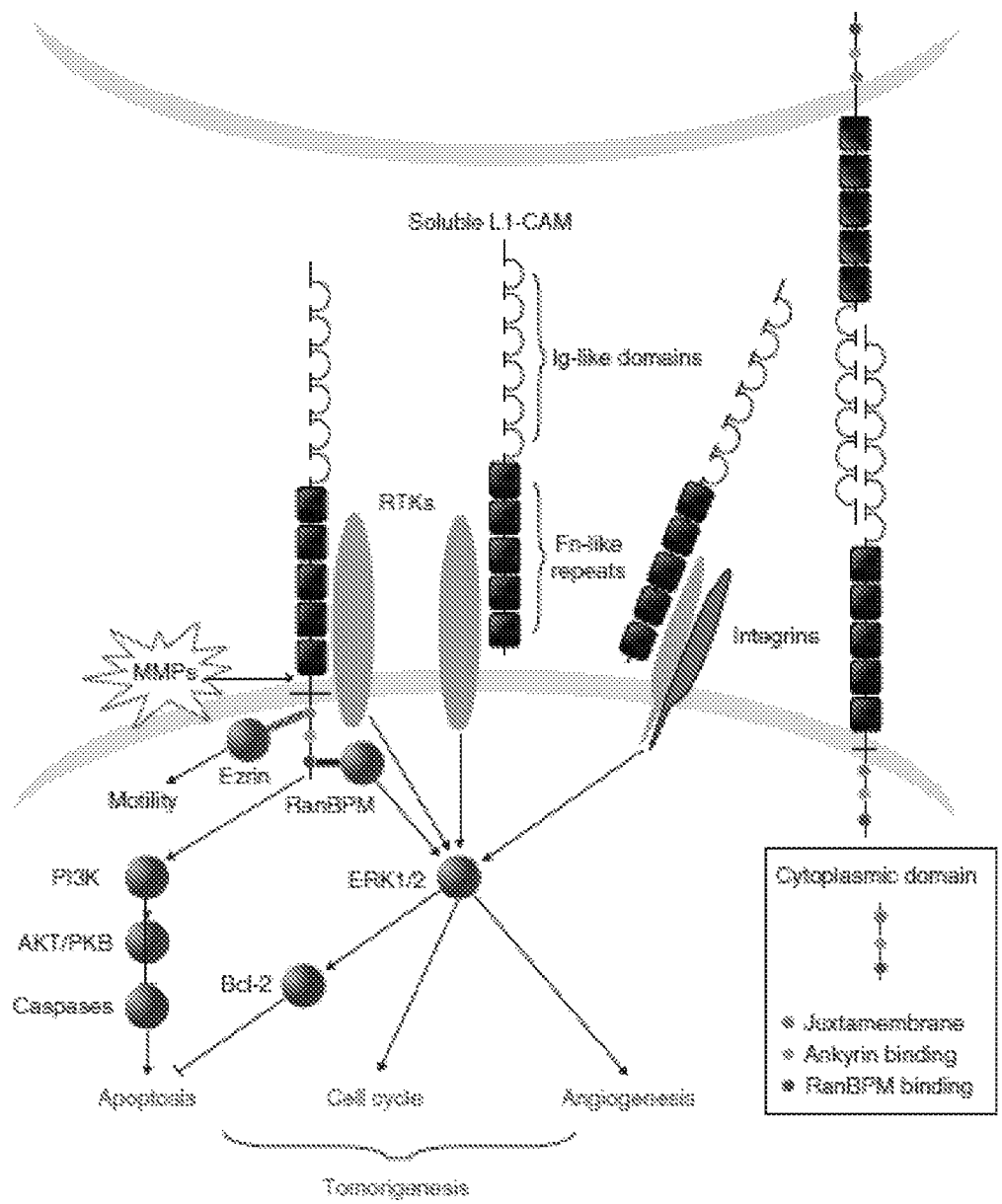
FIG. 2 shows L1-CAM interaction with integrins and cell signaling (adapted from Gavert et al., *Expert opinion Biol Therapy* 8: 1749, 2008).

L1-CAM is a member of the L1 family of adhesion molecules, a part of the immunoglobulin superfamily (IgSF CAMs) and is involved in axon guidance, neural cell migration and differentiation. The L1 family includes L1-CAM (CD171), close homolog of L1-CAM (CHL1), neurofascin and NgCAM-related cell adhesion molecule (NR-CAM). These proteins are expressed in neurons, especially on their axons and glial cells such as Schwann cells. L1-CAM is a neural cell adhesion molecule involved in the development of the central nervous system. L1-CAM is composed of 28 exons and 27 introns and the molecular weight of its gene product ranges between 200 and 220 kDa (Coutelle O et al., *Gene* 208:7-15 (1998)). The extracellular domain (ECM, exon 1 to exon 24) has six Ig-like domains (FIG. 1) and five fibronectin-like domains, with an N-glycosylation in the first fibronectin domain. An RGD motif is present in the $6^{th}$ Ig-like domain. The ECM participates in homophilic binding (FIG. 2), and shares a homology region with FGFR. The cytoplasmic domain contains five potential phospho-serine residues and can interact with the cytoskeleton, second messenger pathways and kinases. Two exons (2 and 27) are spliced alternatively (Coutelle O et al., *Gene* 208:7-15 (1998)).

L1-CAM mutations cause an X-linked neurological disorder called CRASH (Corpus callosum hypoplasia, Retardation, Adducted thumbs, Spastic paraplegia and Hydrocephalus). The clinical syndrome resulting from L1-CAM mutations is variable: more than 70 L1-CAM mutations have been described in all parts of the L1-CAM molecule in CRASH patients. L1-CAM knock-out mice show hyperplasia of the corticospinal tract and abnormalities of the ventricular system. L1-CAM mediates adhesion to different substrates in a context-dependent manner. By hemophilic binding, L1-CAM interacts with other adhesion molecules such as axonin-1/TAX-1, contactin, neurocan, neuropilin 1 and integrins such as αvβ, α5β1, αvβ1 and αvβ5. Cis (between molecules in the same cell membrane) and trans (between molecules on opposing membranes) interactions have been described. N-linked carbohydrates in the ECM account for 25% of the molecular weight of L1-CAM. The ECM has two proteolytic cleavage sites: distal site cleaved by the metalloprotease ADAM 10 resulting in fragments of 200 and 32 kDa. L1-CAM was shown be involved in multiple proliferation-, anti-apoptosis- and angiogenesis-related pathways.

L1-CAM is normally found in neural tissue (FIG. 3), whereas nonneural cells including cancer cells, predominantly express a variant lacking exons 2 and 27. Exon 2 (YEGHHV, coding for the N-terminal Ig1 domain) is important for homophilic L1-L1 binding in vitro and is required for optimal binding to heterophilic ligands. RSLE sequence containing L1-CAM encoded by exon 27 (cytoplasmic tail) is internalized 2-3 times faster than L1Δ(RSLE). RSLE-dependent endocytosis is a mechanism to regulate the surface density of L1-CAM, which in turn controls neurite branching and cell adhesion. Ovarian carcinoma cell lines predominantly express L1-CAMΔ in vitro. ERK activation by L1-CAM requires endocytosis of L1-CAM mediated by exon 27. These different splice variants may have different or even opposing functions in the biology of cancer.

L1-CAM Signaling in Human Cancers.

L1-CAM and its cleaving enzyme, ADAM10, when found at the invasive front, were associated with metastatic potential of colorectal cancer. β-catenin-Wnt, by signaling through L1-CAM is known to confer cell motility, invasion and tumorigenesis in fibroblasts and colon cancer cells. Whether by homophilic or heterophilic binding, L1-CAM promotes cell motility and maintains the invasive phenotype. In the presence of serum or platelet-derived growth factor, L1-CAM stimulates the extracellular signal-related kinase (ERK) pathway, leading to expression of motility- and invasion-related gene products such as β3 integrin subunit, small GTPases and cysteine proteases, cathepsin-L and cathepsin-B. L1-CAM together with IGF2R and SCL31A1 were identified as survival factors protecting tumor cells from apoptosis.

L1-CAM on ovarian carcinoma binds to neuropilin-1 on mesothelial cells which form the lining of the peritoneum, inducing tumor growth by reciprocal signaling between mesothelial cells and tumors. Expression of the non-neuronal isoform of L1-CAM was found in 16 out of 17 tumor cell lines originating from different tumor types (Shtutman M et al., *Cancer Res* 66:11370-80 (2006)). Knock-down of non-neuronal L1-CAM disrupts adherens junctions and increases β-catenin transcriptional activity in breast cancer cell line MCF-7. Full-length L1-CAM undergoes sequential cleavage by ADAM 10 and presenilin/γ-secretase, before the C-terminal fragment of L1-CAM is translocated to the nucleus for gene regulation. The RGD binding site located in the $6^{th}$ Ig domain of L1-CAM appears to be important for nuclear signaling.

Metalloproteinase mediated ectodomain shedding of L1-CAM to its soluble form (sL1-CAM) has physiological consequences. sL1-CAM mediates angiogenesis probably by ligating integrins through the RGD motif. sL1-CAM induces proliferation, matrigel invasion, tube formation of bovine aortic endothelial cells, and proangiogenic activity. sL1-CAM is a ligand for several integrins and can be deposited in the extracellular matrix. The cytoplasmic domain of L1-CAM regulates basal shedding and association with the cytoskeleton through the ankyrin binding site. Exosomes carrying constitutive cleavage products of L1-CAM from ovarian carcinoma cell lines can be found in the ascites fluid and serum of ovarian cancer patients. L1-CAM can also mediate vascular co-option and metastatic outgrowth in a brain metastasis model. Tissue plasmin destroys L1-CAM thereby stopping the metastatic process. Tumor-derived anti-plasminogen, neuroserpin, can prevent plasmin-mediated destruction of L1-CAM or release of membrane-bound astrocytic FasL, a paracrine death signal for cancer cells.

L1-CAM is also involved in chemoresistance. For example, ovarian carcinoma cells expressing L1-CAM are more resistant to apoptosis, partly through the antiapoptotic molecule Bcl-2. In L1-CAM(+) HEK-293 cells, L1-CAM mediates ERK, FAK and PAK phosphorylation. Cell lines selected for cisplatin resistance up-regulates L1-CAM expression, whose its knockdown restores sensitivity.

L1-CAM in Human Tissues and Tumors.

Figure 3:
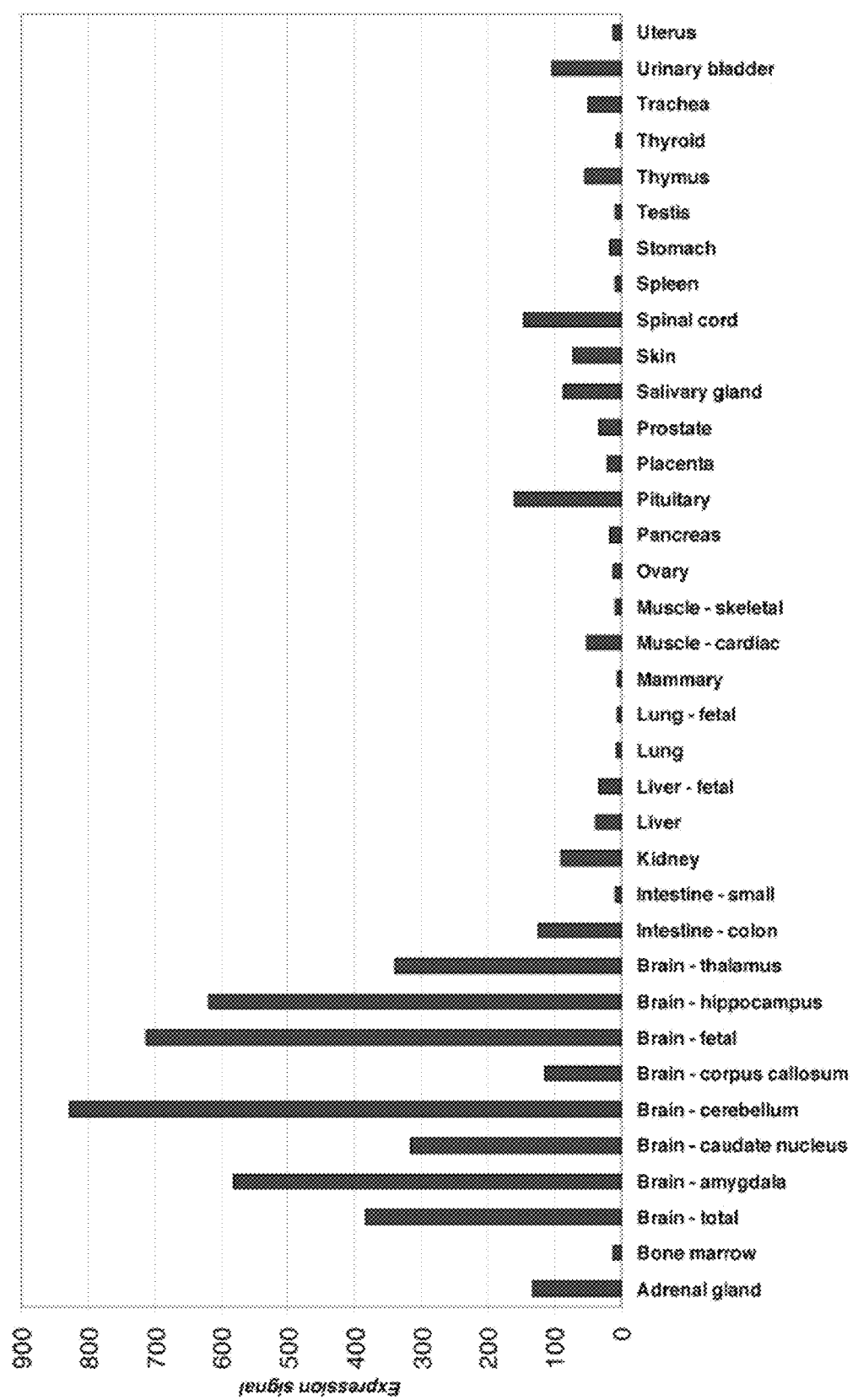
FIG. 3 shows the expression of L1-CAM in normal human tissues (adapted from Weidle et al., *Anticancer Research* 29: 4919-4932, 2009).

In normal human tissues, L1-CAM was detected in neural tissues and peripheral nerves, skin basal cells and small blood vessels, and most notably in the mature placenta (FIG. 3). Tumors that express L1-CAM include those of neuroectodermal and neural crest origin (including neuroblastoma, GIST, pheochromocytoma, paraganglioma, glioma, pancreatic neuroectodermal cancer, etc.), pancreatic adenocarcinoma, ovarian and uterine cancer, colorectal cancer, small cell lung cancer and non-small cell lung cancer, renal cell carcinoma, triple negative breast cancer, and tumor blood vessels (FIG. 4). IHC carried out on tissue micro-arrays of 128 different tumor types (approximately 5500 different samples) using a mouse monoclonal IgG antibody (UJ127) revealed L1-CAM expression in tumors of neural and neural crest origin, but not as well in those of epithelial origin (see FIG. 4; Negative (no detectable staining when evaluated compared to nonspecific background staining), weak (1+ staining or 2+ staining in <30% of tumor cells), or strong (3+ staining or 2+ staining in >30% of tumor cells)). More than 25% positivity (weak plus strong) was found among neuroblastoma, granular cell tumor of the ovary, schwannoma, pheochromocytoma, GIST, primitive neuroectodermal tumor (PNET), epitheliod sarcoma, esthesioneuroblastoma, medulloblastoma, paraganglioma, capillary hemangioma, Kaposi sarcoma. Between 10% to 25% was found for malignant melanoma, chondrosarcoma, esophageal adenocarcinoma, colorectal cancer, and oligodendroglioma. Between 5-10% was found for ependymoma, pancreatic neuroendocrine carcinoma, small cell lung cancer, adrenal adenoma, leiomyosarcoma, liposarcoma, astrocytoma and endometrial cancer. Less than 5% was found for benign nevus, malignant mesothelioma, cervical carcinoma, esophageal squamous carcinoma, meningioma, mucosa associated lymphoid tissue, neurofibroma and pancreatic adenocarcinoma and prostate cancer. In general, L1-CAM was associated with poorly differentiated advanced disease stage often with metastasis. Anti-L1-CAM antibodies such as CE7 (E72) fail to react with monocytes, which express L1-CAM transcripts. This suggests that L1-CAM may be subjected to different post-translational modifications in tumors versus normal tissues that allow preferential binding of anti-L1-CAM antibodies.

Figure 5:
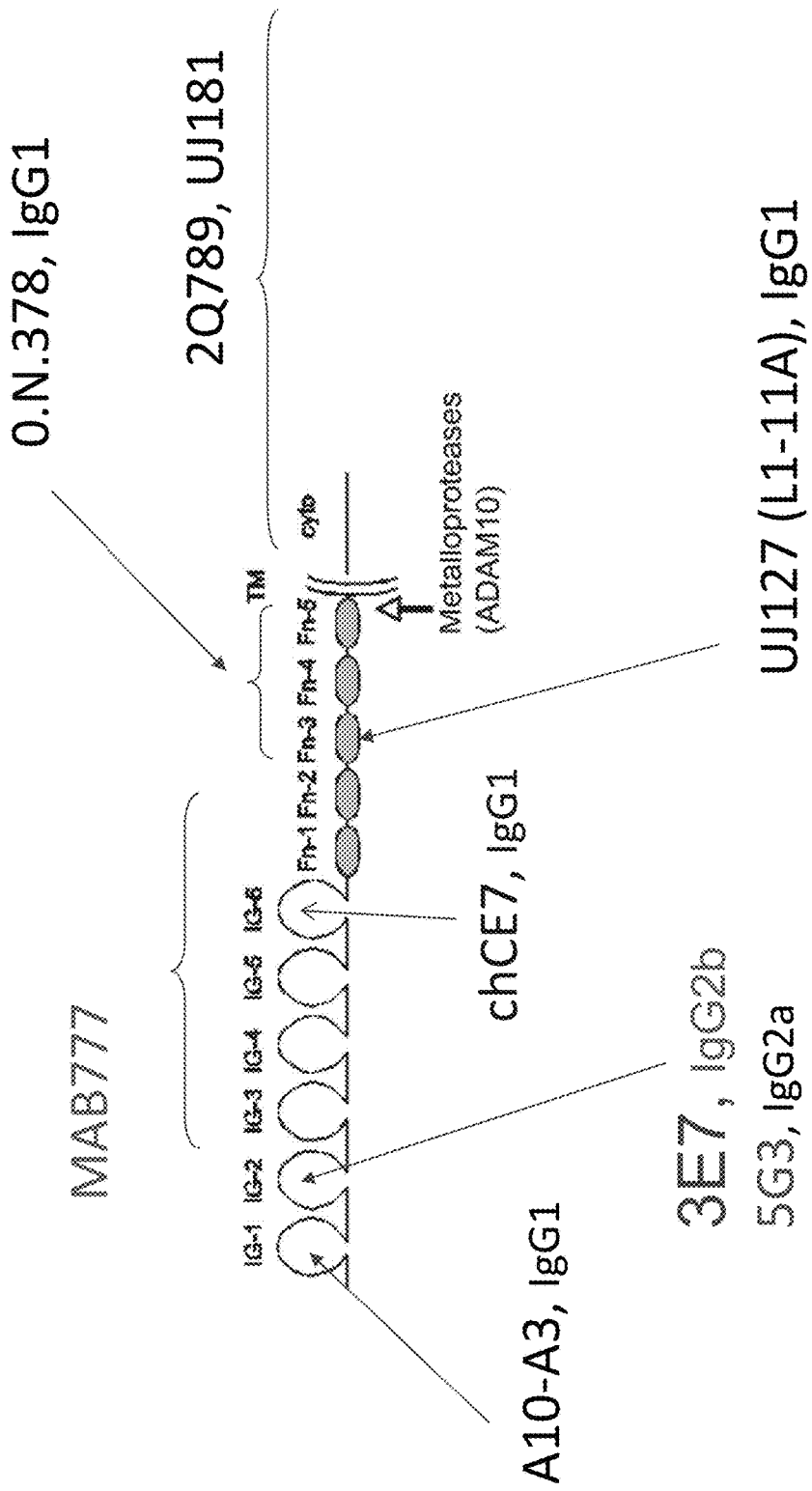
FIG. 5 shows the different murine and chimeric antibodies directed at L1-CAM.

Existing Antibodies Directed Against L1-CAM.

chCE7 binds to the 6th Ig-like domain (with RGD motif) of human L1-CAM (FIG. 1) on renal carcinoma cells and is internalized by human neuroblastoma cells (Meli M L et al., *Int J Cancer* 83:401-8 (1999); Novak-Hofer I et al., *Int J Cancer* 57:427-432 (1994)). Other monoclonal antibodies have also been described: 5G3, A10-A3, UJ127, L1-14.10, MAB777 (R&D systems Inc., Minneapolis, Minn.), and 0.N.378 (U.S Biological Life Sciences, Salem, Mass.), representing a diverse spectrum of epitopes and affinities (FIG. 5). However, a systematic evaluation of in vitro and in vivo properties of each of these L1-CAM antibodies directed against different epitopes has not been done, and their clinical impact remains uncertain. Many anti-L1-CAM antibodies (e.g., chCE7) are inefficient with respect to eliciting Antibody-Dependent Cell-mediated Cytotoxicity (ADCC). Some anti-L1-CAM antibodies may potentially induce unwanted immunogenic responses within a patient.

Immunoglobulin-Related Compositions of the Present Technology

The present technology describes methods and compositions for the generation and use of anti-L1-CAM immunoglobulin-related compositions (e.g., anti-L1-CAM antibodies or antigen binding fragments thereof). The anti-L1-CAM immunoglobulin-related compositions of the present disclosure may be useful in the diagnosis, or treatment of L1-CAM-positive cancers. Anti-L1-CAM immunoglobulin-related compositions within the scope of the present technology include, e.g., but are not limited to, monoclonal, chimeric, humanized, and diabodies that specifically bind the target polypeptide, a homolog, derivative or a fragment thereof. The present disclosure also provides antigen binding fragments of any of the anti-L1-CAM antibodies disclosed herein, wherein the antigen binding fragment is selected from the group consisting of Fab, F(ab)'2, Fab', $scF_v$, and $F_v$.

In one aspect, the present technology provides an antibody or an antigen binding fragment thereof, comprising a heavy chain immunoglobulin variable domain ($V_H$) and a light chain immunoglobulin variable domain ($V_L$), wherein (a) the $V_H$ comprises a $V_H$-CDR1 sequence of GYTFT-SYWMQ (SEQ ID NO: 53), a $V_H$—CDR2 sequence of EINPSNGRTNYNEMFKS (SEQ ID NO: 54), and a $V_H$-CDR3 sequence of YDGYYAMDY (SEQ ID NO: 55); and/or; (b) the $V_L$ comprises a $V_L$-CDR1 sequence of KSSQSLLYSSNQKNYLA (SEQ ID NO: 56), a $V_L$—CDR2 sequence of WASTRES (SEQ ID NO: 57), and a $V_L$-CDR3 sequence of QQYHSYPFT (SEQ ID NO: 58). In some embodiments of the antibody or antigen binding fragment, the $V_H$ comprises the amino acid sequence of SEQ ID NO: 1 and the $V_L$ comprises amino acid sequence of SEQ ID NO: 3. Additionally or alternatively, in some embodiments, the antibody further comprises a Fc domain of any isotype, e.g., but are not limited to, IgG (including IgG1, IgG2, IgG3, and IgG4), IgA (including $IgA_1$ and $IgA_2$), IgD, IgE, or IgM, and IgY. Non-limiting examples of constant region sequences include:

Human IgD constant region, Uniprot: P01880
(SEQ ID NO: 59)
APTKAPDVFPIISGCRHPKDNSPVVLACLITGYHPTSVTVTWYMGTQSQ
PQRTFPEIQRRDSYYMTSSQLSTPLQQWRQGEYKCVVQHTASKSKKEIF
RWPESPKAQASSVPTAQPQAEGSLAKATTAPATTRNTGRGGEEKKKEKE
KEEQEERETKTPECPSHTQPLGVYLLTPAVQDLWLRDKATFTCFVVGSD
LKDAHLTWEVAGKVPTGGVEEGLLERHSNGSQSQHSRLTLPRSLWNAGT
SVTCTLNHPSLPPQRLMALREPAAQAPVKLSLNLLASSDPPEAASWLLC
EVSGFSPPNILLMWLEDQREVNTSGFAPARPPPQPGSTTFWAWSVLRVP
APPSPQPATYTCVVSHEDSRTLLNASRSLEVSYVTDHGPMK Human IgG1 constant region, Uniprot: P01857
(SEQ ID NO: 60)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK Human IgG2 constant region, Uniprot: P01859
(SEQ ID NO: 61)
ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDISVEWESNGQPENNYKTTPPMLDSDGSFFLYSKLTVDKS
RWQQGNVFSCSVMHEALHNHYTQKSLSLSPGK Human IgG3 constant region, Uniprot: P01860
(SEQ ID NO: 62)
ASTKGPSVFPLAPCSRSTSGGTAALGCLVKDYFPEPVTVSWNSGALTSG
VHTFPAVLQSSGLYSLSSVVTVPSSSLGTQTYTCNVNHKPSNTKVDKRV
ELKTPLGDTTHTCPRCPEPKSCDTPPPCPRCPEPKSCDTPPPCPRCPEP
KSCDTPPPCPRCPAPELLGGPSVFLFPPKPKDTLMISRTPEVTCVVVDV
SHEDPEVQFKWYVDGVEVHNAKTKPREEQYNSTFRVVSVLTVLHQDWLN
GKEYKCKVSNKALPAPIEKTISKTKGQPREPQVYTLPPSREEMTKNQVS
LTCLVKGFYPSDIAVEWESSGQPENNYNTTPPMLDSDGSFFLYSKLTVD
KSRWQQGNIFSCSVMHEALHNRFTQKSLSLSPGK Human IgM constant region, Uniprot: P01871
(SEQ ID NO: 63)
GSASAPTLFPLVSCENSPSDTSSVAVGCLAQDFLPDSITLSWKYKNNSD
ISSTRGFPSVLRGGKYAATSQVLLPSKDVMQGTDEHVVCKVQHPNGNKE
KNVPLPVIAELPPKVSVFVPPRDGFFGNPRKSKLICQATGFSPRQIQVS
WLREGKQVGSGVTTDQVQAEAKESGPTTYKVTSTLTIKESDWLGQSMFT
CRVDHRGLTFQQNASSMCVPDQDTAIRVFAIPPSFASIFLTKSTKLTCL
VTDLTTYDSVTISWTRQNGEAVKTHTNISESHPNATFSAVGEASICEDD
WNSGERFTCTVTHTDLPSPLKQTISRPKGVALHRPDVYLLPPAREQLNL
RESATITCLVTGFSPADVFVQWMQRGQPLSPEKYVTSAPMPEPQAPGRY
FAHSILTVSEEEWNTGETYTCVAHEALPNRVTERTVDKSTGKPTLYNVS
LVMSDTAGTCY Human IgG4 constant region, Uniprot: P01861
(SEQ ID NO: 64)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPPCPSCPAPEFLGGPSVFLFPPKPKDTLMISRTPEVTCVVVDVS
QEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDK
SRWQEGNVFSCSVMHEALHNHYTQKSLSLSLGK Human IgA1 constant region, Uniprot: P01876
(SEQ ID NO: 65)
ASPTSPKVFPLSLCSTQPDGNVVIACLVQGFFPQEPLSVTWSESGQGVT
ARNFPPSQDASGDLYTTSSQLTLPATQCLAGKSVTCHVKHYTNPSQDVT
VPCPVPSTPPTPSPSTPPTPSPSCCHPRLSLHRPALEDLLLGSEANLTC
TLTGLRDASGVTFTWTPSSGKSAVQGPPERDLCGCYSVSSVLPGCAEPW
NHGKTFTCTAAYPESKTPLTATLSKSGNTFRPEVHLLPPPSEELALNEL
VTLTCLARGFSPKDVLVRWLQGSQELPREKYLTWASRQEPSQGTTTFAV
TSILRVAAEDWKKGDTFSCMVGHEALPLAFTQKTIDRLAGKPTHVNVSV
VMAEVDGTCY Human IgA2 constant region, Uniprot: P01877
(SEQ ID NO: 66)
ASPTSPKVFPLSLDSTPQDGNVVVACLVQGFFPQEPLSVTWSESGQNVT
ARNFPPSQDASGDLYTTSSQLTLPATQCPDGKSVTCHVKHYTNPSQDVT
VPCPVPPPPCCHPRLSLHRPALEDLLLGSEANLTCTLTGLRDASGATF
TWTPSSGKSAVQGPPERDLCGCYSVSSVLPGCAQPWNHGETFTCTAAHP
ELKTPLTANITKSGNTFRPEVHLLPPPSEELALNELVTLTCLARGFSPK
DVLVRWLQGSQELPREKYLTWASRQEPSQGTTTFAVTSILRVAAEDWKK
GDTFSCMVGHEALPLAFTQKTIDRMAGKPTHVNVSVVMAEVDGTCY Human Ig kappa constant region, Uniprot: P01834
(SEQ ID NO: 67)
TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVT
KSFNRGEC In some embodiments, the immunoglobulin-related compositions of the present technology comprise a heavy chain constant region that is at least 80%, at least 85%, at least 90%, at least 95%, at least 99%, or is 100% identical to SEQ ID NOS: 59-66. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 67. In some embodiments, the immunoglobulin-related compositions of the present technology bind to an epitope of a L1-CAM polypeptide comprising at least five to eight consecutive amino acid residues of the 2nd Ig-like domain of L1-CAM (SEQ ID NO: 74). In some embodiments, the epitope is a conformational epitope.

In another aspect, the present disclosure provides an isolated immunoglobulin-related composition (e.g., an antibody or antigen binding fragment thereof) comprising a heavy chain (HC) amino acid sequence of:

(SEQ ID NO: 9)
QVQLVQPGDELVKPGASVKLSCKASGYTFTSYWMQWVKQRPGQGLEWIG
EINPSNGRTNYNEMEKSKAVLSVDKSVSTAYMQLSSLTAEDTAVYYCAL
YDGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKS
LSLSPGK (huE71-H1);

(SEQ ID NO: 10)
QVQLVQSGSELKKPGASVKLSCKASGYTFTSYWMQWVRQAPGQGLEWIG
EINPSNGRTNYNEMFKSRAVLSVDTSVSTAYMQLCSLKAEDTAVYYCAL
YDGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKS
LSLSPGK (huE71-H2);

(SEQ ID NO: 17)
QVQLVQPGAEVVKPGASVKLSCKASGYTFTGYWMHWVKQAPGQGLEWIG
EINPSNGRTNYNERFKSKATLTVDKSITTAFMELSRLRSDDTAVYFCAR
DYYGTSYNFDYWGQGTLLTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK (huE72-H1);

(SEQ ID NO: 18)
QVQLVQPGAEVKKPGASVKLSCKASGYTFTGYWMHWVRQAPGQGLEWIG
EINPSNGRTNYNERFKSRATLTVDKSISTAYMELSRLRSDDTAVYFCAR
DYYGTSYNFDYWGQGTLLTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK (huE72-H2);

(SEQ ID NO: 26)
QVQLQQPGDELVKPGASVKLSCKASGYTFTSYWMQWVKQRPGQGLEWIG
EINPSNGRTNYNEMFKSKATLTVDKSSSTAYMQLSSLTSEDSAVYYCAL
YDGYYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKS
LSLSPGK (chE71-IgG1);

(SEQ ID NO: 30)
QVQLQQPGDELVKPGASVKLSCKASGYTFTSYWMQWVKQRPGQGLEWIG
EINPSNGRTNYNEMFKSKATLTVDKSSSTAYMQLSSLTSEDSAVYYCAL
YDGYYAMDYWGQGTSVTVSSASTKGPSVFPLAPSSKSTSGGTAALGCLV
KDYFPEPVTVSWNSGALTSGVHTFPAVLQSSGLYSLSSVVTVPSSSLGT
TQYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKS
LSLSPGK (chE72-IgG1);

(SEQ ID NO: 42)
QVQLQQPGDELVKPGASVKLSCKASGYTFTSYWMQWVKQRPGQGLEWIG
EINPSNGRTNYNEMFKSKATLTVDKSSSTAYMQLSSLTSEDSAVYYCAL
YDGYYAMDYWGQGTSVTVSSASTKGPSVFPLAPCSRSTSESTAALGCLV
KDYFPEPVTVSWNSGALTSGVHTFPAVLQSSGLYSLSSVVTVPSSSLGT
KTYTCNVDHKPSNTKVDKRVESKYGPPCPSCPAPEFLGGPSVFLFPPKP
KDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSL
SLGK (chE71-IgG4);

(SEQ ID NO: 46)
QVQLVQPGDELVKPGASVKLSCKASGYTFTSYWMQWVKQRPGQGLEWIG
EINPSNGRTNYNEMFKSKAVLSVDKSVSTAYMQLSSLTAEDTAVYYCAL

```
YDGYYAMDYWGQGTLVTVSSASTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPSCPAPEFLGGPSVFLPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGK (huE71-IgG4);

(SEQ ID NO: 49)
QVQLVQPGDELVKPGASVKLSCKASGYTFTSYWMQWVKQRPGQGLEWIG

EINPSNGRTNYNEMFKSKAVLSVDKSVSTAYMQLSSLTAEDTAVYYCAL

YDGYYAMDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCAVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK (huE71-BsAb);

(SEQ ID NO: 51)
QVQLVQPGAEVVKPGASVKLSCKASGYTFTGYWMHWVKQAPGQGLEWIG

EINPSNGRTNYNERFKSKATLTVDKSITTAFMELSRLRSDDTAVYFCAR

DYYGTSYNFDYWGQGTLLTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYASTYRVVSVLTVLHQDWLNGKEYKCAVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK (huE72-BsAb)
``` or a variant thereof having one or more conservative amino acid substitutions.

Additionally or alternatively, in some embodiments, the immunoglobulin-related compositions of the present technology comprise a light chain (LC) amino acid sequence of:

```
                                        (SEQ ID NO: 13)
DIVMTQSPSSLAVSVGERVTMSCKSSQSLLYSSNQKNYLAWYQQKPGQ

SPKLLIYWASTRESGVPDRFSGSGSGTDFTLTISSVKAEDVALYYCQQY

HSYPFTFGQGTKLEIKRTVAAPSVFIFPPSDEQLKSGTASVVCLLNNFY

PREAKVQWKVDNALQSGNSQESVTEQDSKDSTYSLSSTLTLSKADYEKH

KVYACEVTHQGLSSPVTKSFNRGEC (huE71-L1), (SEQ ID NO: 14)
DIVMTQSPDSLAVSLGERVTMNCKSSQSLLYSSNQKNYLAWYQQKPGQP

PKLLIYWASTRESGVPDRFSGSGSGTDFTLTISSLQAEDVALYYCQQYH

SYPFTFGQGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC (huE71-L2), (SEQ ID NO: 21)
DIQMTQSSSSFSVSVGDRVTITCKANEDINNRLAWYQQKPGKSPRLLIS

GATNLVTGVPSRFSGSGSGTDYTLTISSLQAEDFATYYCQQYWSTPFTF

GQGTELEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (huE72-L1), (SEQ ID NO: 22)
DIQMTQSPSSLSVSVGDRVTITCKANEDINNRLAWYQQKPGKAPKLLIS

GATNLVTGVPSRFSGSGSGTDYTLTISSLQPEDFATYYCQQYWSTPFTF

GQGTELEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (huE72-L2), (SEQ ID NO: 25)
DIVMSQSPSSLAVSVGEKVTMSCKSSQSLLYSSNQKNYLAWYQQKPGQS

PKLLIYWASTRESGVPDRFTGSGSGTDFTLTISSVKAEDLALYYCQQYH

SYPFTFGSGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC (chE71-IgG1 Light chain), (SEQ ID NO: 29)
DIQMTQSSSSFSVSLGDRVTITCKANEDINNRLAWYQQTPGNSPRLLIS

GATNLVTGVPSRFSGSGSGKDYTLTITSLQAEDFATYYCQQYWSTPFTF

GSGTELEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (chE72 IgG1-Light Chain), (SEQ ID NO: 41)
DIVMSQSPSSLAVSVGEKVTMSCKSSQSLLYSSNQKNYLAWYQQKPGQS

PKLLIYWASTRESGVPDRFTGSGSGTDFTLTISSVKAEDLALYYCQQYH

SYPFTFGSGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC (chE71-IgG4 Light Chain), (SEQ ID NO: 45)
DIVMTQSPSSLAVSVGERVTMSCKSSQSLLYSSNQKNYLAWYQQKPGQS

PKLLIYWASTRESGVPDRFSGSGSGTDFTLTISSVKAEDLALYYCQQYH

SYPFTFGQGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC (huE71-IgG4 Light Chain),
```

-continued (SEQ ID NO: 50)
DIVMTQSPSSLAVSVGERVTMSCKSSQSLLYSSNQKNYLAWYQQKPGQS

PKLLIYWASTRESGVPDRFSGSGSGTDFTLTISSVKAEDVALYYCQQYH

SYPFTFGQGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGECTSGGGGSGGGGSGGGGSQVQLVQSG

GGVVQPGRSLRLSCKASGYTFTRYTMHWVRQAPGKCLEWIGYINPSRGY

TNYNQKFKDRFTISRDNSKNTAFLQMDSLRPEDTGVYFCARYYDDHYSL

DYWGQGTPVTVSSGGGGSGGGGSGGGGSGGGGSGGGGSGGGGSDIQMTQ

SPSSLSASVGDRVTITCSASSSVSYMNWYQQTPGKAPKRWIYDTSKLAS

GVPSRFSGSGSGTDYTFTISSLQPEDIATYYCQQWSSNPFTFGCGTKLQ

ITR (huE71-BsAb Light Chain-huOKT3scFv), (SEQ ID NO: 52)
DIQMTQSPSSLSVSVGDRVTITCKANEDINNRLAWYQQKPGKAPKLLIS

GATNLVTGVPSRFSGSGSGTDYTLTISSLQPEDFATYYCQQYWSTPFTF

GQGTELEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGECTSGGGGSGGGGSGGGGSQVQLVQSGGGVVQP

GRSLRLSCKASGYTFTRYTMHWVRQAPGKCLEWIGYINPSRGYTNYNQK

FKDRFTISRDNSKNTAFLQMDSLRPEDTGVYFCARYYDDHYSLDYWGQG

TPVTVSSGGGGSGGGGSGGGGSGGGGSGGGGSGGGGSDIQMTQSPSSLS

ASVGDRVTITCSASSSVSYMNWYQQTPGKAPKRWIYDTSKLASGVPSRF

SGSGSGTDYTFTISSLQPEDIATYYCQQWSSNPFTFGCGTKLQITR (huE72-BsAb Light Chain-huOKT3scFv), or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 9 and SEQ ID NO: 13 (huE71 H1/L1); SEQ ID NO: 9 and SEQ ID NO: 14 (huE71 H1/L2); SEQ ID NO: 10 and SEQ ID NO: 13 (huE71 H2/L1); SEQ ID NO: 10 and SEQ ID NO: 14 (huE71 H2/L2); SEQ ID NO: 17 and SEQ ID NO: 21 (huE72 H1/L1); SEQ ID NO: 17 and SEQ ID NO: 22 (huE72 H1/L2); SEQ ID NO: 18 and SEQ ID NO: 21 (huE72 H2/L1); SEQ ID NO: 18 and SEQ ID NO: 22 (huE72 H2/L2); SEQ ID NO: 26 and SEQ ID NO: 25 (chE71IgG1); SEQ ID NO: 30 and SEQ ID NO: 29 (chE72 IgG1); SEQ ID NO: 42 and SEQ ID NO: 41 (chE71IgG4); SEQ ID NO: 46 and SEQ ID NO: 45 (huE71IgG4); SEQ ID NO: 49 and SEQ ID NO: 50 (huE71 BsAb); and SEQ ID NO: 51 and SEQ ID NO: 52 (huE72 BsAb), respectively.

In any of the above embodiments of the immunoglobulin-related compositions, the HC and LC immunoglobulin variable domain sequences form an antigen binding site that binds to an epitope of a L1-CAM polypeptide comprising at least five to eight consecutive amino acid residues of the 2nd Ig-like domain of L1-CAM (SEQ ID NO: 74) or the 6th Ig-like domain of L1-CAM (SEQ ID NO: 75). In some embodiments, the epitope is a conformational epitope.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one L1-CAM polypeptide. In some embodiments, the immunoglobulin-related compositions of the present technology bind at least one L1-CAM polypeptide with a dissociation constant ($K_d$) of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In certain embodiments, the immunoglobulin-related composition includes one or more of the following characteristics: (a) the light chain immunoglobulin variable domain sequence is at least 80%, at least 85%, at least 90%, at least 95%, or at least 99% identical to the light chain immunoglobulin variable domain sequence present in any one of SEQ ID NOs: 13, 14, 21, 22, 25, 29, 41, 45, 50 or 52; and/or (b) the heavy chain immunoglobulin variable domain sequence is at least 80%, at least 85%, at least 90%, at least 95%, or at least 99% identical to the heavy chain immunoglobulin variable domain sequence present in any one of SEQ ID NOs: 9, 10, 17, 18, 26, 30, 42, 46, 49, and 51. In another aspect, one or more amino acid residues in the immunoglobulin-related compositions provided herein are substituted with another amino acid. The substitution may be a "conservative substitution" as defined herein.

In some embodiments, the immunoglobulin-related composition comprises (a) a LC sequence that is at least 80%, at least 85%, at least 90%, at least 95%, or at least 99% identical to the LC sequence present in any one of SEQ ID NOs: 13, 14, 21, 22, 25, 29, 41, 45, 50 or 52; and/or (b) a HC sequence that is at least 80%, at least 85%, at least 90%, at least 95%, or at least 99% identical to the HC sequence present in any one of SEQ ID NOs: 9, 10, 17, 18, 26, 30, 42, 46, 49, and 51.

In certain embodiments, the immunoglobulin-related compositions contain an IgG1 constant region comprising one or more amino acid substitutions selected from the group consisting of N297A and K322A. Additionally or alternatively, in some embodiments, the immunoglobulin-related compositions contain an IgG4 constant region comprising a S228P mutation.

In some aspects, the anti-L1-CAM immunoglobulin-related compositions described herein contain structural modifications to facilitate rapid binding and cell uptake and/or slow release. In some aspects, the anti-L1-CAM immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a F(ab)'$_2$ fragment is used to facilitate rapid binding and cell uptake and/or slow release.

In one aspect, the present technology provides a nucleic acid sequence encoding a heavy chain or a light chain of an immunoglobulin-related composition described herein. Also disclosed herein are recombinant nucleic acid sequences encoding any of the antibodies described herein. In some embodiments, the nucleic acid sequence is selected from the group consisting of SEQ ID NOs: 11, 12, 15, 16, 19, 20, 23, 24, 27, 28, 31, 32, 43, 44, 47 and 48. In another aspect, the present technology provides a host cell expressing any nucleic acid sequence encoding a heavy chain or a light chain of an immunoglobulin-related composition described herein.

The immunoglobulin-related compositions of the present technology (e.g., an anti-L1-CAM antibody) can be monospecific, bispecific, trispecific or of greater multispecificity. Multispecific antibodies can be specific for different epitopes of one or more L1-CAM polypeptides or can be specific for both the L1-CAM polypeptide(s) as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985, 566; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-L1-CAM Antibodies of the Present Technology

General Overview.

Initially, a target polypeptide is chosen to which an antibody of the present technology can be raised. For example, an antibody may be raised against the full-length L1-CAM protein, or to a portion of the extracellular domain of the L1-CAM protein comprising the six Ig-like domains and five fibronectin-like domains (see FIG. 1). Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from L1-CAM protein containing the extracellular domain which is capable of eliciting an immune response. The preparation of antibodies specific for L1-CAM protein is illustrated in Examples 1, 2 and 5.

It should be understood that recombinantly engineered antibodies and antibody fragments, e.g., antibody-related polypeptides, which are directed to L1-CAM protein and fragments thereof are suitable for use in accordance with the present disclosure.

Anti-L1-CAM antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli*.

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes L1-CAM proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens.

Methods of generating antibodies or antibody fragments of the present technology typically include immunizing a subject (generally a non-human subject such as a mouse or rabbit) with a purified L1-CAM protein or fragment thereof or with a cell expressing the L1-CAM protein or fragment thereof. An appropriate immunogenic preparation can contain, e.g., a recombinantly-expressed L1-CAM protein or a chemically-synthesized L1-CAM peptide. The ECM of L1-CAM protein, or a portion or fragment thereof, can be used as an immunogen to generate an anti-L1-CAM antibody that binds to the L1-CAM protein, or a portion or fragment thereof using standard techniques for polyclonal and monoclonal antibody preparation.

The full-length L1-CAM protein or fragments thereof, are useful as fragments as immunogens. In some embodiments, a L1-CAM fragment comprises at least five to eight consecutive amino acid residues of the amino acid sequence PKETVKPVEVEEGESVVLPCNPPPSAEPL-RIYWMNSKILHIKQDERVTMGQNGNLYF ANVLT-SDNHSDYICHAHFPGTRTIIQKEPID (SEQ ID NO: 74) (Ig-like C2-type 2 domain of L1-CAM) or TQITQGPRSTIEKKGSRVTFTCQASFDPSLQPSIT-WRGDGRDLQELGDSDKYFIEDGRL VIHSLDYSDQG-NYSCVASTELDVVESRAQLL (SEQ ID NO: 75) (Ig-like C2-type 6 domain of L1-CAM), and encompasses an epitope of the L1-CAM protein such that an antibody raised against the peptide forms a specific immune complex with L1-CAM protein.

In some embodiments, the antigenic L1-CAM peptide overlapping with the 2nd or 6th Ig-like domain comprises at least 5, 8, 10, 15, 20, or 30 amino acid residues. Longer antigenic peptides are sometimes desirable over shorter antigenic peptides, depending on use and according to methods well known to those skilled in the art. Multimers of a given epitope are sometimes more effective than a monomer.

If needed, the immunogenicity of the L1-CAM protein (or fragment thereof) can be increased by fusion or conjugation to a hapten such as keyhole limpet hemocyanin (KLH) or ovalbumin (OVA). Many such haptens are known in the art. One can also combine the L1-CAM protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., L1-CAM protein. In some embodiments, the immunization can occur as a result of vaccinating the individual with a vaccine containing the antigen. For example, the vaccine can be a L1-CAM vaccine comprising one or more L1-CAM protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ T cells. A first exposure to an antigen primes the immune system and additional exposure(s) results in a DTH.

Following appropriate immunization, the anti-L1-CAM antibody can be prepared from the subject's serum. If desired, the antibody molecules directed against the L1-CAM protein can be isolated from the mammal (e.g., from the blood) and further purified by well-known techniques, such as polypeptide A chromatography to obtain the IgG fraction.

Monoclonal Antibody.

In one embodiment of the present technology, the antibody is an anti-L1-CAM monoclonal antibody. For example, in some embodiments, the anti-L1-CAM monoclonal antibody may be a human or a mouse anti-L1-CAM monoclonal antibody. For preparation of monoclonal antibodies directed towards the L1-CAM protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96).

Human monoclonal antibodies can be utilized in the practice of the present technology and can be produced by using human hybridomas (See, e.g., Cote, et al., 1983. *Proc. Natl. Acad. Sci. USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the L1-CAM protein. Alternatively, hybridomas expressing anti-L1-CAM monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., L1-CAM binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of L1-CAM protein. Also, CPG-dinucleotide techniques can be used to enhance the immunogenic properties of the L1-CAM protein. Other manipulations include substituting or deleting particular amino acyl residues that contribute to instability of the antibody during storage or after administration to a subject, and affinity maturation techniques to improve affinity of the antibody of the L1-CAM protein.

Hybridoma Technique.

In some embodiments, the antibody of the present technology is an anti-L1-CAM monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique.

As noted above, the antibodies of the present technology can be produced through the application of recombinant DNA and phage display technology. For example, anti-L1-CAM antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for a L1-CAM polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.,* 85: 5879-5883, 1988; Chaudhary et al., *Proc. Natl. Acad. Sci U.S.A.,* 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-L1-CAM Antibodies.

As noted above, the antibodies of the present technology can be produced through the application of recombinant DNA technology. Recombinant polynucleotide constructs encoding an anti-L1-CAM antibody of the present technology typically include an expression control sequence operably-linked to the coding sequences of anti-L1-CAM antibody chains, including naturally-associated or heterologous promoter regions. As such, another aspect of the technology includes vectors containing one or more nucleic acid sequences encoding an anti-L1-CAM antibody of the present technology. For recombinant expression of one or more of the polypeptides of the present technology, the nucleic acid containing all or a portion of the nucleotide sequence encoding the anti-L1-CAM antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-L1-CAM antibody, and the collection and purification of the anti-L1-CAM antibody, e.g., cross-reacting anti-L1-CAM antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with L1-CAM binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-L1-CAM antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-L1-CAM antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-L1-CAM antibody, etc.).

Another aspect of the present technology pertains to anti-L1-CAM antibody-expressing host cells, which contain a nucleic acid encoding one or more anti-L1-CAM antibodies. The recombinant expression vectors of the present technology can be designed for expression of an anti-L1-CAM antibody in prokaryotic or eukaryotic cells. For example, an anti-L1-CAM antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-L1-CAM antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-L1-CAM antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-L1-CAM antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-L1-CAM antibody can be expressed in insect cells using baculovirus expression vectors. Baculovirus vectors available for expression of polypeptides, e.g., anti-L1-CAM antibody, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding an anti-L1-CAM antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-L1-CAM antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-L1-CAM antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, N Y, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-L1-CAM antibody or can be introduced on a separate vector. Cells stably transfected with the introduced nucleic acid can be identified by drug selection (e.g., cells that have incorporated the selectable marker gene will survive, while the other cells die).

A host cell that includes an anti-L1-CAM antibody of the present technology, such as a prokaryotic or eukaryotic host cell in culture, can be used to produce (i.e., express) recombinant anti-L1-CAM antibody. In one embodiment, the method comprises culturing the host cell (into which a recombinant expression vector encoding the anti-L1-CAM antibody has been introduced) in a suitable medium such that the anti-L1-CAM antibody is produced. In another embodiment, the method further comprises the step of isolating the anti-L1-CAM antibody from the medium or the host cell. Once expressed, collections of the anti-L1-CAM antibody, e.g., the anti-L1-CAM antibodies or the anti-L1-CAM antibody-related polypeptides are purified from culture media and host cells. The anti-L1-CAM antibody can be purified according to standard procedures of the art, including HPLC purification, column chromatography, gel electrophoresis and the like. In one embodiment, the anti-L1-CAM antibody is produced in a host organism by the method of Boss et al., U.S. Pat. No. 4,816,397. Usually, anti-L1-CAM antibody chains are expressed with signal sequences and are thus released to the culture media. However, if the anti-L1-CAM antibody chains are not naturally secreted by host cells, the anti-L1-CAM antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-L1-CAM antibodies, e.g., the anti-L1-CAM antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies.

In one embodiment, the anti-L1-CAM antibody of the present technology is a single-chain anti-L1-CAM antibody. According to the present technology, techniques can be adapted for the production of single-chain antibodies specific to a L1-CAM protein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203: 46-88, 1991; Shu, L. et al., *Proc. Natl. Acad. Sci. USA,* 90: 7995-7999, 1993; and Skerra et al., *Science* 240: 1038-1040, 1988.

Chimeric and Humanized Antibodies.

In one embodiment, the anti-L1-CAM antibody of the present technology is a chimeric anti-L1-CAM antibody. In one embodiment, the anti-L1-CAM antibody of the present technology is a humanized anti-L1-CAM antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-L1-CAM antibodies, such as chimeric and humanized monoclonal antibodies, comprising both human and non-human portions, can be made using standard recombinant DNA techniques, and are within the scope of the present technology. For some uses, including in vivo use of the anti-L1-CAM antibody of the present technology in humans as well as use of these agents in in vitro detection assays, it is possible to use chimeric or humanized anti-L1-CAM antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., PNAS 91: 969-973, 1994), and chain shuffling (U.S. Pat. No. 5,565,332). In one embodiment, a cDNA encoding a murine anti-L1-CAM monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-L1-CAM antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-L1-CAM antibodies, heavy and light chain immunoglobulins.

CDR Antibodies.

In some embodiments, the anti-L1-CAM antibody of the present technology is an anti-L1-CAM CDR antibody. Generally the donor and acceptor antibodies used to generate the anti-L1-CAM CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one need replace only as many as necessary to permit adequate binding of the resulting CDR-grafted antibody to L1-CAM protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-L1-CAM CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-L1-CAM CDR-grafted antibody significantly compared to the same antibody with a fully human FR.

Bispecific Antibodies (BsAbs).

A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, L1-CAM and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, TCR gamma/delta, NKp46 and KIR. In certain embodiments, the BsAbs are capable of binding to tumor cells that express L1-CAM antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for L1-CAM and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54(22):5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In other embodiments, the bispecific fusion protein is tetravalent, comprising, for example, an immunoglobulin (e.g., IgG) with two binding sites for one antigen and two identical scFv for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., L1-CAM) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science* 321:974-977 (2008)).

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10): 1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any L1-CAM immunoglobulin disclosed herein. In some certain embodiments, scFvs are linked to the C-terminal end of the light chain of any L1-CAM immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of a L1-CAM antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a $G_4S$ linker (SEQ ID NO: 76). In some certain embodiments, a BsAb of the present technology comprises a $(G_4S)_n$ linker, wherein n is 1, 2, 3, 4, 5, 6, 7, 8, 9, 10, 11, 12, 13, 14, 15 or more (SEQ ID NO: 78).

Fc Modifications.

In some embodiments, the anti-L1-CAM antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature,* 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-L1-CAM antibody of the present technology has an altered affinity for activating and/or inhibitory receptors, having a variant Fc region with one or more amino acid modifications, wherein said one or more amino acid modification is a N297 substitution with alanine, or a K322 substitution with alanine.

Glycosylation Modifications.

In some embodiments, anti-L1-CAM antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., L1-CAM), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (huL1-CAM-IgG1n) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17: 176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277, 370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, JMB, 336: 1239-49.

Fusion Proteins.

In one embodiment, the anti-L1-CAM antibody of the present technology is a fusion protein. The anti-L1-CAM antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-L1-CAM antibodies. For instance, a region of additional amino acids, particularly charged amino acids, can be added to the N-terminus of the anti-L1-CAM antibody to improve stability and persistence during purification from the host cell or subsequent handling and storage. Also, peptide moieties can be added to an anti-L1-CAM antibody to facilitate purification. Such regions can be removed prior to final preparation of the anti-L1-CAM antibody. The addition of peptide moieties to facilitate handling of polypeptides are familiar and routine techniques in the art. The anti-L1-CAM antibody of the present technology can be fused to marker sequences, such as a peptide which facilitates purification of the fused polypeptide. In select embodiments, the marker amino acid sequence is a hexa-histidine peptide (SEQ ID NO: 79), such as the tag provided in a pQE vector (QIA-GEN, Inc., Chatsworth, Calif.), among others, many of which are commercially available. As described in Gentz et al., *Proc. Natl. Acad. Sci. USA* 86: 821-824, 1989, for instance, hexa-histidine (SEQ ID NO: 79) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., J. Biochem. 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.*, 270: 9459-9471, 1995.

Labeled Anti-L1-CAM Antibodies.

In one embodiment, the anti-L1-CAM antibody of the present technology is coupled with a label moiety, i.e., detectable group. The particular label or detectable group conjugated to the anti-L1-CAM antibody is not a critical aspect of the technology, so long as it does not significantly interfere with the specific binding of the anti-L1-CAM antibody of the present technology to the L1-CAM protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{131}I$, $^{112}In$, $^{99m}Tc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-L1-CAM antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-L1-CAM antibodies. In this case, antigen-coated particles are agglutinated by samples comprising the target antibodies. In this format, none of the components need be labeled and the presence of the target antibody is detected by simple visual inspection.

B. Identifying and Characterizing the Anti-L1-CAM Antibodies of the Present Technology Methods for Identifying and/or Screening the Anti-L1-CAM Antibodies of the Present Technology.

Methods useful to identify and screen antibodies against L1-CAM polypeptides for those that possess the desired specificity to L1-CAM protein include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS,* 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^3$H-thymidine; (4) the phagocytic capacity of granulocytes, macrophages, and other phagocytes in PBMCs can be measured by placing PBMCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-L1-CAM antibodies of the present technology are selected using display of L1-CAM peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-L1-CAM antibodies of the present technology are selected using display of L1-CAM peptides on the surface of a yeast host cell. Methods useful for the isolation of scFv polypeptides by yeast surface display have been described by Kieke et al., *Protein Eng.* 1997 November; 10(11): 1303-10.

In some embodiments, anti-L1-CAM antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In certain embodiments, anti-L1-CAM antibodies of the present technology are selected using tRNA display of L1-CAM peptides. Methods useful for in vitro selection of ligands using tRNA display have been described by Merryman et al., *Chem. Biol.*, 9: 741-46, 2002.

In one embodiment, anti-L1-CAM antibodies of the present technology are selected using RNA display. Methods useful for selecting peptides and proteins using RNA display libraries have been described by Roberts et al. *Proc. Natl. Acad. Sci. USA*, 94: 12297-302, 1997; and Nemoto et al., *FEBS Lett.*, 414: 405-8, 1997. Methods useful for selecting peptides and proteins using unnatural RNA display libraries have been described by Frankel et al., *Curr. Opin. Struct. Biol.*, 13: 506-12, 2003.

In some embodiments, anti-L1-CAM antibodies of the present technology are expressed in the periplasm of gram negative bacteria and mixed with labeled L1-CAM protein. See WO 02/34886. In clones expressing recombinant polypeptides with affinity for L1-CAM protein, the concentration of the labeled L1-CAM protein bound to the anti-L1-CAM antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-L1-CAM antibodies, it is contemplated that said antibodies can be produced in large volume by any technique known to those skilled in the art, e.g., prokaryotic or eukaryotic cell expression and the like. The anti-L1-CAM antibodies which are, e.g., but not limited to, anti-L1-CAM hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of L1-CAM Binding.

In some embodiments, a L1-CAM binding assay refers to an assay format wherein L1-CAM protein and an anti-L1-CAM antibody are mixed under conditions suitable for binding between the L1-CAM protein and the anti-L1-CAM antibody and assessing the amount of binding between the L1-CAM protein and the anti-L1-CAM antibody. The amount of binding is compared with a suitable control, which can be the amount of binding in the absence of the L1-CAM protein, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of L1-CAM protein binding to anti-L1-CAM antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-L1-CAM antibody is at least 1 percent greater than the binding observed in the absence of the candidate anti-L1-CAM antibody, the candidate anti-L1-CAM antibody is useful as an anti-L1-CAM antibody of the present technology.

Measurement of L1-CAM Neutralization.

As used here, "L1-CAM neutralization" refers to reduction of the activity and/or expression of L1-CAM protein through the binding of an anti-L1-CAM antibody. The capacity of anti-L1-CAM antibodies of the present technology to neutralize L1-CAM activity/expression may be assessed in vitro or in vivo using methods known in the art.

Uses of the Anti-L1-CAM Antibodies of the Present Technology

General.

The anti-L1-CAM antibodies of the present technology are useful in methods known in the art relating to the localization and/or quantitation of a L1-CAM protein (e.g., for use in measuring levels of the L1-CAM protein within appropriate physiological samples, for use in diagnostic methods, for use in imaging the polypeptide, and the like). Antibodies of the present technology are useful to isolate a L1-CAM protein by standard techniques, such as affinity chromatography or immunoprecipitation. An anti-L1-CAM antibody of the present technology can facilitate the purification of natural immunoreactive L1-CAM proteins from biological samples, e.g., mammalian sera or cells as well as recombinantly-produced immunoreactive L1-CAM proteins expressed in a host system. Moreover, anti-L1-CAM antibodies can be used to detect an immunoreactive L1-CAM protein (e.g., in plasma, a cellular lysate or cell supernatant) in order to evaluate the abundance and pattern of expression of the immunoreactive polypeptide. The anti-L1-CAM antibodies of the present technology can be used diagnostically to monitor immunoreactive L1-CAM protein levels in tissue as part of a clinical testing procedure, e.g., to determine the efficacy of a given treatment regimen. As noted above, the detection can be facilitated by coupling (i.e., physically linking) the anti-L1-CAM antibodies of the present technology to a detectable substance.

Detection of L1-CAM Protein.

An exemplary method for detecting the presence or absence of an immunoreactive L1-CAM protein in a biological sample involves obtaining a biological sample from a test subject and contacting the biological sample with an anti-L1-CAM antibody of the present technology capable of detecting an immunoreactive L1-CAM protein such that the presence of an immunoreactive L1-CAM protein is detected in the biological sample. Detection may be accomplished by means of a detectable label attached to the antibody.

The term "labeled" with regard to the anti-L1-CAM antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-L1-CAM antibodies disclosed herein are conjugated to one or more detectable labels. For such uses, anti-L1-CAM antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P $^{35}$S, $^{14}$C, $^{51}$Cr, $^{57}$To, $^{58}$Co $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled L1-CAM-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive L1-CAM protein in a biological sample in vitro as well as in vivo. In vitro techniques for detection of an immunoreactive L1-CAM protein include enzyme linked immunosorbent assays (ELISAs), Western blots, immunoprecipitations, radioimmunoassay, and immunofluorescence. Furthermore, in vivo techniques for detection of an immunoreactive L1-CAM protein include introducing into a subject a labeled anti-L1-CAM antibody. For example, the anti-L1-CAM antibody can be labeled with a radioactive marker whose presence and location in a subject can be detected by standard imaging techniques. In one embodiment, the biological sample contains L1-CAM protein molecules from the test subject.

Immunoassay and Imaging.

An anti-L1-CAM antibody of the present technology can be used to assay immunoreactive L1-CAM protein levels in a biological sample (e.g., human plasma) using antibody-based techniques. For example, protein expression in tissues can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^3$H), indium ($^{112}$In), and technetium ($^{99}$mTc), and fluorescent labels, such as fluorescein, rhodamine, and green fluorescent protein (GFP), as well as biotin.

In addition to assaying immunoreactive L1-CAM protein levels in a biological sample, anti-L1-CAM antibodies of the present technology may be used for in vivo imaging of L1-CAM. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-L1-CAM antibodies by labeling of nutrients for the relevant scFv clone.

An anti-L1-CAM antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled anti-L1-CAM antibody will then accumulate at the location of cells which contain the specific target polypeptide. For example, labeled anti-L1-CAM antibodies of the present technology will accumulate within the subject in cells and tissues in which the L1-CAM protein has localized.

Thus, the present technology provides a diagnostic method of a medical condition, which involves: (a) assaying the expression of immunoreactive L1-CAM protein by measuring binding of an anti-L1-CAM antibody of the present technology in cells or body fluid of an individual; (b) comparing the amount of immunoreactive L1-CAM protein present in the sample with a standard reference, wherein an increase or decrease in immunoreactive L1-CAM protein levels compared to the standard is indicative of a medical condition.

Affinity Purification.

The anti-L1-CAM antibodies of the present technology may be used to purify immunoreactive L1-CAM protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers*, pp, 4-12 (1995); Rothschild et al., *Nucl. Acids Res.*, 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association.

An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-L1-CAM Antibodies of the Present Technology

General.

The anti-L1-CAM antibodies of the present technology are useful in diagnostic methods. As such, the present technology provides methods using the antibodies in the diagnosis of L1-CAM activity in a subject. Anti-L1-CAM antibodies of the present technology may be selected such that they have any level of epitope binding specificity and very high binding affinity to a L1-CAM protein. In general, the higher the binding affinity of an antibody the more stringent wash conditions can be performed in an immunoassay to remove nonspecifically bound material without removing target polypeptide. Accordingly, anti-L1-CAM antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that anti-L1-CAM antibodies used as diagnostic reagents have a sufficient kinetic on-rate to reach equilibrium under standard conditions in at least 12 h, at least five (5) h, or at least one (1) hour.

Anti-L1-CAM antibodies can be used to detect an immunoreactive L1-CAM protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of L1-CAM protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-L1-CAM antibody or a population of anti-L1-CAM antibodies immobilized to a solid phase, and another anti-L1-CAM antibody or a population of anti-L1-CAM antibodies in solution. Typically, the solution anti-L1-CAM antibody or population of anti-L1-CAM antibodies is labeled. If an antibody population is used, the population can contain antibodies binding to different epitope specificities within the target polypeptide. Accordingly, the same population can be used for both solid phase and solution antibody. If anti-L1-CAM monoclonal antibodies are used, first and second L1-CAM monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the L1-CAM protein with the anti-L1-CAM antibody, a sample is incubated for a period that usually varies from about 10 min to about 24 hr and is usually about 1 hr. A wash step is then performed to remove components of the sample not specifically bound to the anti-L1-CAM antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive L1-CAM protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the L1-CAM protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-L1-CAM antibodies can be joined to a linker molecule, such as biotin for attachment to a surface bound linker, such as avidin.

In some embodiments, the present disclosure provides an anti-L1-CAM antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the L1-CAM antibodies of the present technology. Macrocyclic chelates such as NOTA (1,4,7-triaza-cyclononane-N,N',N''-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-NH$_2$; (ii) Ac-Lys(HSG)D-Tyr-Lys(HSG)-Lys(Tscg-Cys)-NH$_2$; (iii) DOTA-D-Asp-D-Lys(HSG)-D-Asp-D-Lys(HSG)-NH$_2$; (iv) DOTA-D-Glu-D-Lys(HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-Lys(DTPA)-D-Tyr-D-Lys(DTPA)-NH$_2$; (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys(Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys(HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys(DTPA)-NH$_2$; (xviii) Ac-D-Lys(DTPA)-D-Tyr-D-Lys(DTPA)-D-Lys(Tscg-Cys)-NH$_2$; and (xix) Ac-D-Lys(DOTA)-D-Tyr-D-Lys(DOTA)-D-Lys(Tscg-Cys)-NH$_2$.

Other ring-type chelates such as macrocyclic polyethers, which are of interest for stably binding nuclides, such as $^{223}$Ra for RAIT are also contemplated.

B. Therapeutic Use of Anti-L1-CAM Antibodies of the Present Technology

The immunoglobulin-related compositions (e.g., antibodies or antigen binding fragments thereof) of the present technology are useful for the treatment of L1-CAM associated cancers. Such treatment can be used in patients identified as having pathologically high levels of the L1-CAM (e.g., those diagnosed by the methods described herein) or in patients diagnosed with a disease known to be associated with such pathological levels. In one aspect, the present disclosure provides a method for treating a L1-CAM associated cancer in a subject in need thereof, comprising administering to the subject an effective amount of an antibody (or antigen binding fragment thereof) of the present technology. Examples of cancers that can be treated by the antibodies of the present technology include, but are not limited to: leukemia, Ewing's sarcoma, neuroblastoma, osteosarcoma, glioblastoma multiforme, ovarian cancer, endometrial cancer, uterine cancer, triple negative breast cancer, melanoma, clear cell renal cell cancer, pheochromacytoma and paraganglioma, mesothelioma, small cell lung cancer (SCLC), non-small cell lung cancer, NSCLC, pancreatic ductal cancer, colon cancer, pancreatic cancer, hepatocellular carcinoma, gastric cancer, cholangiocarcinoma, carcinoid, neuroendocrine tumors, gastrointestinal stromal tumor (GIST), pheochromocytoma, glioma, pancreatic neuroectodermal cancer, pancreatic adenocarcinoma, colorectal cancer, renal cell carcinoma, tumor blood vessels, chondrosarcoma, esophageal adenocarcinoma, oligodendroglioma, astrocytoma, ependymoma, pancreatic neuroendocrine carcinoma, adrenal adenoma, leiomyosarcoma, liposarcoma, granular cell tumor of the ovary, schwannoma, primitive neuroectodermal tumor (PNET), epitheliod sarcoma, esthesioneuroblastoma, medulloblastoma, capillary hemangioma, Kaposi sarcoma, rhabdomyosarcoma, submaxillary salivary gland cancer, and head and neck squamous cell carcinoma.

The compositions of the present technology may be employed in conjunction with other therapeutic agents useful in the treatment of L1-CAM associated cancers. For example, the antibodies of the present technology may be separately, sequentially or simultaneously administered with at least one additional therapeutic agent-selected from the group consisting of alkylating agents, platinum agents, taxanes, *vinca* agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-L1-CAM antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-L1-CAM antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-L1-CAM antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting a tumor in a subject in vivo comprising (a) administering to the subject an effective amount of an antibody (or antigen binding fragment thereof) of the present technology, wherein the antibody is configured to localize to a tumor expressing L1-CAM and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, 1Re, $^{177}$Lu, and $^{67}$Cu. Examples of alpha particle-emitting isotopes include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh $^{195m}$Pt, $^{119}$Sb, $^{161}$Ho, $^{189m}$OS, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity.

Optimally, an effective amount (e.g., dose) of anti-L1-CAM antibody described herein will provide therapeutic benefit without causing substantial toxicity to the subject. Toxicity of the anti-L1-CAM antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-L1-CAM antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions.

According to the methods of the present technology, the anti-L1-CAM antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-L1-CAM antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-L1-CAM antibody named in this technology can be present in unsalified or unesterified form, or in salified and/or esterified form, and the naming of such anti-L1-CAM antibody is intended to include both the original (unsalified and unesterified) compound and its pharmaceutically-acceptable salts and esters. Also, certain embodiments of the present technology can be present in more than one stereoisomeric form, and the naming of such anti-L1-CAM antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-L1-CAM antibody, use thereof in the compositions is contemplated. Supplementary active compounds can also be incorporated into the compositions.

A pharmaceutical composition of the present technology is formulated to be compatible with its intended route of administration. The anti-L1-CAM antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-L1-CAM antibody can optionally be administered in combination with other agents that are at least partly effective in treating various L1-CAM associated cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-L1-CAM antibody of the present technology in the required amount in an appropriate solvent with one or a combination of ingredients enumerated above, as required, followed by filtered sterilization. Generally, dispersions are prepared by incorporating the anti-L1-CAM antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-L1-CAM antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-L1-CAM antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-L1-CAM antibody is formulated into ointments, salves, gels, or creams as generally known in the art.

The anti-L1-CAM antibody can also be prepared as pharmaceutical compositions in the form of suppositories (e.g., with conventional suppository bases such as cocoa butter and other glycerides) or retention enemas for rectal delivery.

In one embodiment, the anti-L1-CAM antibody is prepared with carriers that will protect the anti-L1-CAM antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal Suspensions (Including Liposomes Targeted to Infected Cells with Monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the detection and/or treatment of L1-CAM associated cancers, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of L1-CAM associated cancers. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive L1-CAM protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-L1-CAM antibodies of the present technology (or antigen binding fragments thereof) capable of binding a L1-CAM protein in a biological sample; means for determining the amount of the L1-CAM protein in the sample; and means for comparing the amount of the immunoreactive L1-CAM protein in the sample with a standard. One or more of the anti-L1-CAM antibodies may be labeled. The kit components, (e.g., reagents) can be packaged in a suitable container. The kit can further comprise instructions for using the kit to detect the immunoreactive L1-CAM protein.

For antibody-based kits, the kit can comprise, e.g., 1) a first antibody, e.g. a humanized, chimeric or bispecific L1-CAM antibody of the present technology (or an antigen binding fragment thereof), attached to a solid support, which binds to a L1-CAM protein; and, optionally; 2) a second, different antibody which binds to either the L1-CAM protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a L1-CAM protein in vitro or in vivo, or for treatment of L1-CAM associated cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative L1-CAM antibodies of the present technology. Examples 1-11 demonstrate the production of chimeric, humanized, and bispecific antibodies of the present technology, and characterization of their binding specificities and in vivo biological activities.

Example 1: Materials and Methods for Generating and Characterizing the Anti-L1-CAM Antibodies of the Present Technology Immunohistochemistry (IHC). Use of human tumors and normal tissues for IHC was approved by Memorial Sloan-Kettering Cancer Center institutional review board. Five-to seven-micrometer sections of snap-frozen tissues were fixed in acetone for 30 minutes at −20° C. Endogenous biotin-binding activity was blocked by sequential treatment with avidin and biotin (Vector avidin-biotin blocking kit; Invitrogen, Carlsbad, Calif.) for 20 minutes each followed by blocking with 10% horse serum for 1 hour at room temperature. Sections were then sequentially reacted with primary antibody, biotinylated horse antimouse IgG (H+L) (Vector Laboratories, Inc., Burlingame, Calif.) and Avidin-Biotin Complex (Vectastain ABC kit, Vector Laboratories, Inc., Burlingame, Calif.) for 60 minutes respectively at room temperature, and washed between each reaction. Subsequently, sections were stained with dye (DAB Peroxidase substrate kit, Vector Laboratories, Burlingame, Calif.) for 2 min, washed, counterstained with Myer's hematoxylin, washed, dehydrated in 95% ethyl alcohol.

Construction of the Chimeric and Humanized Forms of E71 and E72.

Based on human homologues, CDR sequences of both heavy and light chains of E71 and E72 were grafted into the human IgG1 framework and optimized. The huE71 and huE72 genes were synthesized (Blue Heron Biotechnology, Bothhell, Wash. or Genscript, Piscataway, N.Y.) and incorporated into a mammalian expression vector (Eureka, Calif.), and transfected into DG44 cells or CHO-S cells for stable production. Similarly, human $V_H$ and $V_L$ sequences were grafted onto human IgG4 frameworks to make IgG4 recombinant antibodies. Lastly, these genes were transfected into DG44 cells that lack the GnT1 enzyme to make the special IgG1 glycoforms.

Purification of Chimerized or Humanized E71 and E72.

HuE71 and huE72 producer lines were cultured in Opticho serum free medium (Invitrogen, Carlsbad, Calif.) or PowerCHO-2 (Lonza, Basel, Switzerland) and the mature supernatant was harvested. Protein A affinity column was pre-equilibrated with 25 mM sodium citrate buffer with 0.15 M NaCl, pH 8.2. Bound huE71 or huE72 were eluted with 0.1 M citric acid/sodium citrate buffer, pH 3.9 and alkalinized (1:10 v/v ratio) in 25 mM sodium citrate, pH 8.5. It was passed through a Sartobind-Q membrane and concentrated to 5-10 mg/mL in 25 mM sodium citrate, 0.15 M NaCl, pH 8.2. 2 μg each of the proteins was analyzed by SDS-PAGE under non-reducing or reducing conditions using 4-15% Tris-Glycine Ready Gel System (Bio-Rad, Hercules, Calif.). Invitrogen SeeBlue Plus2 Pre-Stained Standard (Invitrogen, Carlsbad, Calif.) was used as the protein molecular weight marker. After electrophoresis, the gel was stained using GelCode Blue Stain Reagent (Pierce Biotechnology, Waltham, Mass.). The gel was scanned using Bio-Rad Fluor-S MultiImager (Bio-Rad, Hercules, Calif.), and the band intensity quantified with Quantity One software (Bio-Rad, Hercules, Calif.).

In Vitro Binding Kinetics by Biacore T-100 Biosensor (GE Healthcare, Uppsala, Sweden).

CM5 sensor chip (Research grade) and related reagents were purchased from Biacore USA (Piscataway, N.J.). Antigen L1-CAM-Fc or L1-CAM-His was directly immobilized onto the CM5 sensor chip according to the manufacturer's instructions. Purified monoclonal antibodies (MoAbs) (mouse, chimeric IgG1 and IgG4, and humanized IgG1 and IgG4 versions of E71 and E72, and their IgG1n glycoforms) were diluted in HBS-EP buffer at varying concentrations (41.7-666.7 nM) prior to analysis. Samples were injected over the sensor surface at a flow rate of 30 μl/min over 1 min. Association time was set for 1 min, dissociation time was set for from 5 min to 15 min. At the end of each cycle, the surface was regenerated using 50 mM NaOH at a flow rate of 50 μl/min over 1 min. The data were analyzed by the bivalent analyte model and default parameter setting for the rate constants using the Biacore T-100 evaluation software, and the apparent association on rate constant ($k_{on}$), dissociation off rate constant ($k_{off}$) and equilibrium dissociation constant ($K_d = k_{off}/k_{on}$) were calculated.

$^{51}$Chromium Release Assay.

For ADCC assays, effector cells were peripheral blood mononuclear cells (PBMCs) from a healthy donor. Effector cell:Target cell (E:T) ratio was 50:1. For T cell cytotoxicity assay, effector T cells cultured in vitro in the presence of anti-CD3 and anti-CD28 for about 14 days, and used at an E:T ratio of 10:1. All target tumor cells were harvested with 2 mM EDTA in PBS, labeled with $^{51}$Cr (Amersham, Arlington Height, Ill.) at 100 μCi/10$^6$ cells at 37° C. for 1 h. 5000 target cells were added per well, together with antibodies in 96-well polystyrene round-bottom plates (BD Biosciences, Bedford, Mass.) to a final volume of 250 l/well. 10 units/ml of IL2 was added for ADCC assays. The plates were incubated at 37° C. for 4 hours. The released $^{51}$Cr in the supernatant was counted in a γ-counter (Packed Instrument, Downers Grove, Ill.). Percentage of specific release was calculated using the formula: (experimental cpm−background cpm)/(total cpm−background cpm)×100%, where cpm represented counts per minute of $^{51}$Cr released. Total release was assessed by lysis with 10% SDS (Sigma, St Louis, Mo.), and background release was measured in the absence of effector cells. EC50 was calculated using Sigmaplot or Graphpad Prism softwares.

Biodistribution of MoAb in Xenografted Mice.

Female athymic nude mice were purchased from Harlan Sprague Dawley, Inc (Indianapolis, Ind.). All procedures were carried out in accordance with the protocols approved by the Memorial Sloan-Kettering Cancer Center Institutional Animal Care and Use Committee and institutional guidelines for the proper and humane use of animals in research. Tumor cells were harvested and resuspended in Matrigel (BD Biosciences, Bedford, Mass.). Cells ($2$-$10 \times 10^6$) were implanted subcutaneously (s.c.) to the flank of the mice in 0.1 ml volume using 22-gauge needles. Tumors were allowed to grow to the size of ~200 mm$^3$ before initiating treatment. Mice with established tumors were randomly separated into treatment groups. 100 μCi of radioiodinated antibody per mouse was injected intravenously and animals sacrificed usually at 48 hours, and their organs removed and counted in a gamma counter (Packard Instruments, Perkin Elmer, Waltham, Mass.). These organs included skin, liver, spleen, kidney, adrenal, stomach, small intestine, large intestine, bladder, femur, muscle, tumor, heart, lung, spine, and brain. Based on the Ci accumulated in the organ and the organ weight, % injected dose (% ID)/gram of mouse was calculated. Tumor to non-tumor ratios of % ID/g were also calculated.

huE71-BsAb Design, Production, and Purification Analyses.

The huE71-BsAb format was designed as a huOKT3 scFv fusion to the C-terminus of the light chain (huE71-huOKT3) of a huE71-IgG1 using a 15 amino acid linker $(G_4S)_3$ (SEQ ID NO: 77). N297A and K322A mutations in the IgG1 Fc region were introduced. Nucleotide sequences were synthesized by GenScript (Piscataway, N.Y.) with appropriate flanking restriction enzyme sites, and were subcloned into a standard mammalian expression vector. Linearized plasmid DNA was used to transfect CHO-S cells (Invitrogen, Carlsbad, Calif.) for stable production of BsAb. $2 \times 10^6$ cells were transfected with 5 μg of plasmid DNA by Nucleofection (Lonza, Basel, Switzerland) and then recovered in CD OptiCHO medium supplemented with 8 mM L-glutamine (Invitrogen, Carlsbad, Calif.) for 2 d at 37° C. in 6-well culture plates. Stable pools were selected with 500 μg/mL hygromycin for approximately two weeks and single clones were then selected out with limited dilution. huE71-BsAb titer was determined by L1-CAM(+) tumor cells and CD3(+) Jurkat cell ELISA, respectively, and stable clones with highest expression were selected. The BsAb producer line was cultured in PowerCHO-2 medium and the mature supernatant harvested. A protein A affinity column (GE Healthcare, Chicago, Ill.) was pre-equilibrated with 25 mM sodium citrate buffer with 0.15 M NaCl, pH 8.2. Bound BsAb was eluted with 0.1 M citric acid/sodium citrate buffer, pH 3.9 and neutralized with 25 mM sodium citrate, pH 8.5 (1:10 v/v ratio). For storage, BsAb was dialyzed into 25 mM sodium citrate, 0.15 M NaCl, pH 8.2 and frozen in aliquots at −80° C. Two micrograms of the protein was analyzed by SDS-PAGE under reducing conditions using 4-15% Tris-Glycine Ready Gel System (Bio-Rad, Hercules, Calif.). The purity of huE71-BsAb was also evaluated by size-exclusion high-performance liquid chromatography (SE-HPLC). Approximately 20 μg of protein was injected into a TSK-GEL G3000SWXL 7.8 mm×30 cm, 5 m column (TOSOH Bioscience, Tokyo, Japan) with 0.4 M NaClO$_4$, 0.05 M NaH$_2$PO$_4$, pH 6.0 buffer at flow rate of 0.5 mL/min, and UV detection at 280 nm. Ten microliters of gel-filtration standard (Bio-Rad, Hercules, Calif.) was analyzed in parallel for MW markers.

FACS Analyses.

Cells were incubated with different concentrations of primary antibody (chimeric or humanized huE71 and huE72 and their IgG4 subclass and IgG1n variants, as well as the BsAb forms) for 30 minutes at 4° C. in PBS, and a secondary phycoerythrin-labeled antibody specific for human Fc was used after washing off of excess primary antibody. Cells were fixed with 1% paraformaldehyde (PFA) prior to analysis on FACS Calibur cytometer (BD Biosciences, Bedford, Mass.). Controls were cells incubated with Rituximab or Palivizumab, for which the mean fluorescent intensity (MFI) was set to 5.

For quantitation, the Quantum Simply Cellular antimouse IgG kit was used (Bangs Laboratories, Fishers, Ind.). Briefly, the kit comprises five microsphere populations; one blank and four labeled with increasing amounts of antimouse IgG. The beads and the tumor cells (37° C. for 5 hours) were then labeled with the same fluorescently conjugated mouse E71 on ice for 30 minutes. The cells were then washed with PBS and analyzed on the BD FACS Calibur (BD Biosciences, Bedford, Mass.) along with the labeled beads. The Excel-based QuickCal analysis template that was provided with each kit aids in correlating fluorescence intensity with antigen density on the tumor cells. Each data point represented the average of duplicates.

In Vivo Anti-Tumor Assays.

For in vivo studies, BALB-Rag2-KO-IL-2R-γc-KO (DKO) mice (derived from colony of Dr. Mamoru Ito, CIEA, Kawasaki, Japan) were used. See Koo G C et al., Expert Rev Vaccines 8:113-20 (2009). Tumor cells were implanted subcutaneously of a 1:1 mixture of fresh media/ BD Matrigel (BD Biosciences, Bedford, Mass.). For tumor volume measurements, all tumors were measured using hand-held TM900 scanner (Peira, Brussels, BE).

General Laboratory Procedures for Radiolabeled Antibody Studies.

Unless otherwise noted, all chemicals were acquired from Sigma-Aldrich (St. Louis, Mo.) and used as received and all instruments were calibrated and maintained in accordance with standard procedures. $^{89}$Zr was produced at Memorial Sloan Kettering Cancer Center on a TR19/9 cyclotron (Ebco Industries Inc., Richmond, BC, Canada) via the $^{89}$Y(p,n) $^{89}$Zr reaction and purified to yield $^{89}$Zr with a specific activity of 196-496 MBq/mg. Activity measurements were made using a CRC-15R Dose Calibrator (Capintec, Inc., Florham Park, N.J.). For the quantification of activities, samples were counted on an Automatic Wizard gamma counter (Perkin Elmer, Waltham, Mass.). The radiolabeling of ligands was monitored using instant thin-layer chromatography paper (Agilent Technologies, Santa Clara, Calif.) and analyzed on a Bioscan AR-2000 radio-ITLC plate reader using Winscan Radio-TLC software (Bioscan Inc., Washington, D.C.). All in vivo experiments were performed according to protocols approved by the Memorial Sloan Kettering Institutional Animal Care and Use Committee (Protocol 08-07-013).

Cell Culture.

T-75 flasks (Corning, Corning N.Y.) containing cells were stored in cell incubators maintained at 37° C. and a 5% CO$_2$ concentration. SKOV3, a human epithelial ovarian carcinoma cell line (ATCC, Manassas, Va.) was cultured in RPMI McCoy's 5A Medium (Thermo Fisher Scientific, Waltham, Mass.), modified to contain 1.5 mM L-glutamine, were all grown with 100 units/mL penicillin G and 100 μg/mL streptomycin and 10% fetal bovine serum. The SKOV3 cell line was subcultivated once per week using 0.25% trypsin/0.53 mM EDTA in Hank's Buffered Salt Solution without calcium and magnesium and passaged 1:5 for standard cell line passaging.

Xenograft Mouse Models.

Eight to ten week old athymic nu/nu female mice were purchased from Charles River Laboratories (Kingston, N.Y.). Animals were housed in ventilated cages, were given food and water ad libitum, and were allowed to acclimate for approximately 1 week prior to inoculation. SKOV-3 tumors were induced on the right shoulder by a subcutaneous injection of $5.0\times10^6$ cells in a 150 µL cell suspension of a 1:1 mixture of fresh media/BD Matrigel (BD Biosciences, Bedford, Mass.). Experiments were performed approximately 2-3 weeks following the injection of the cancer cells. For tumor volume measurements, all tumors measured using hand-held TM900 scanner (Peira, Brussels, BE). After initial tumor measurements, mice were randomized into groups (n=8-9 per group), ensuring all cohort had approximately equal average tumor volumes to start.

Antibody Bioconjugation.

Antibodies were obtained in citrate buffer (25 mM sodium citrate, 150 mM sodium chloride) at an average concentration of 4-5 mg/mL. The antibodies were concentrated using centrifugal filter units with a 50,000 molecular weight cutoff (Amicon Ultra 4 Centrifugal Filtration Units, Millipore Corp., Billerica, Mass.) to a final concentration of 12-15 mg/mL. After concentrating, the antibodies were pH adjusted to 8.5-9.0 with 0.1 M $Na_2CO_3$ before the addition of 10 equivalents of p-SCN-Bn-DFO or p-SCN-Bn-DOTA (Macrocyclics, Inc. Dallas, Tex.) dissolved in DMSO. The reaction was incubated at 37° C. for 1 hour constantly shaking at 500 rpm. The antibodies were purified using centrifugal filter units with a 50,000 molecular weight cutoff (Amicon Ultra 4 Centrifugal Filtration Units, Millipore Corp., Billerica, Mass.) to purify the ligand-antibody conjugate. The final bioconjugates were aliquoted and stored in PBS pH 7.4 at −80° C.

Radiolabeling.

$^{89}Zr$ was received after target processing as $^{89}Zr$-oxalate in 1.0 M oxalic acid. The solution was neutralized with 1.0 M sodium carbonate to reach pH ~7. DFO-antibodies were incubated together with neutralized $^{89}Zr$ labeled in PBS pH 7.4 at 37° C. for 60 minutes. $^{177}LuCl$ was obtained (specific activity: 170 MBq/mg, Perkin Elmer, Waltham, Mass.) and diluted in ammonia acetate buffer (200 mmol/L, pH 5.4) and incubated with DOTA-antibodies at 42° C. for 1 hour. The progress of the reactions was monitored via radio-ITLC with silica-gel impregnated glass-microfiber paper strips (ITLC-SG, Varian, Lake Forest, Calif.) (analyzed by AR-2000, Bioscan Inc., Washington, D.C.) using 50 mM EDTA at pH 5 as the mobile phase. Antibody complexes remained at the origin, while free radionuclide was taken up by EDTA in the mobile phase and migrated along the solvent front. Crude radiochemical yields were calculated using the radio-ITLC data. Radiolabeled antibodies were then purified using size-exclusion chromatography (PD 10), followed by centrifugal filtration to concentrate the final volume for formulation. The radiochemical purity of the final purified radiolabeled antibodies was confirmed to be >99% by radio-ITLC before use.

Serum Stability.

Aliquots of each $^{89}Zr$-antibody complex (100 µL) were incubated with 900 µL of human serum and agitated constantly on a thermomixer at 37° C. Samples were taken from each microcentrifuge tube and analyzed using radio-ITLC at day 0, 1, 3, 5, and 7 in triplicate. The stability of the complexes was measured as the percentage of $^{89}Zr$ that was retained at the origin of the radio-ITLC strip and reported as % intact.

Immunoreactivity.

The immunoreactive fraction of the $^{89}Zr$-DFO-antibodies was determined using a Lindmo cell binding assay (Ben Q W et al., *Ann Surg Oncol* 17:2213-21 (2010)). To this end, SKOV3 cells were suspended in microcentrifuge tubes at concentrations ranging from $5.0\times10^5$-$5.0\times10^6$ cells/mL in 500 µL PBS, 1% BSA (pH 7.4). Aliquots of $^{89}Zr$-DFO-antibody (50 µL of 1 µCi/mL stock were added to each tube to a final volume of 500 µL. The samples were incubated on a thermomixer for 60 min at 37° C. The treated cells were then pelleted via centrifugation (1400 RPM for 4 min), aspirated supernatant, and washed three times with cold PBS before removing the supernatant and counting the cell-associated radioactivity. The activity data were background-corrected and compared with the total number of counts in appropriate control samples. Immunoreactive fractions were determined by linear regression analysis of a plot of (total/bound) activity against (1/[normalized cell concentration]).

PET Imaging.

PET imaging experiments were conducted on an Inveon PET/CT scanner (Siemens Healthcare Global, Malvern, Pa.). Female, athymic nude mice with SKOV3 xenografts on their right shoulders were administered $^{89}Zr$-antibody (192-214 µCi] in 150 µL of PBS) via intravenous tail vein injection. Animals were anesthetized by inhalation of 2% isoflurane (Baxter Healthcare, Deerfield, Ill.) and medical air gas mixture and placed within the scanner with anesthesia maintained using 2% isoflurane and medical air gas mixture. PET data for each mouse were recorded via static scans at 24, 48, 72, and 96 hours post-injection. An energy window of 350-700 keV and a coincidence timing window of 6 ns were used. Data were sorted into 2D histograms by Fourier rebinning, and transverse images were reconstructed by filtered back-projection (FBP) into a 128×128×63 (0.72×0.72×1.3 mm3) matrix. The counting rates in the reconstructed images were converted to activity concentrations (percentage injected dose per gram of tissue, % ID/g) by use of a system calibration factor derived from the imaging of a mouse-sized water-equivalent phantom containing $^{89}Zr$. Images were analyzed using ASIPro VM software (Concorde Microsystems, Knoxville, Tenn.).

Biodistribution.

Biodistribution studies were performed using the $^{89}Zr$-antibodies SKOV3 tumor-bearing female, athymic nude mice. Animals were administered (17-26 µCi) of each of the $^{89}Zr$-antibodies in 150 µL PBS via intravenous tail vein injection. Animals (n=4 per group) were euthanized by $CO_2$ asphyxiation at 96 hours post-injection. Following euthanasia, 17 organs (blood, tumor, heart, lungs, liver, spleen, stomach, large bowel, small bowel, pancreas, ovary, kidney, bone, muscle, lymph, skin, tail) were collected, weighed, and assayed for radioactivity on a gamma counter calibrated for $^{89}Zr$. Counts were converted into activity using a calibration curve generated from known standards. Count data were background and decay corrected to the time of injection, and the percent injected dose per gram (% ID/g) for each tissue sample was calculated by normalization to the total activity injected. The data depicted in this study are expressed as averages±standard deviation. Statistical differences were analyzed by unpaired, two-tailed, student's t-test using GraphPad Prism 7 software. P-values<0.05 were considered statistically significant and indicated by an asterisk.

Example 2: Structure of the Humanized Anti-L1-CAM Antibodies of the Present Technology Humanized E71 and E72 anti-L1-CAM antibodies were generated. Sequence design was based on human IgG homology calculations while conserving critical mouse amino acid residues. FIG. 6 and FIG. 7 show the $V_H$ and $V_L$ of murine E71, represented as SEQ ID NOs: 1 and 3, and the $V_H$ and $V_L$ of murine E72, represented as SEQ ID NOs: 5 and 7, respectively. The CDRs of the heavy and light chains of murine E71 (see FIG. 6) and E72 (see FIG. 7) were grafted onto human IgG1 frameworks based on their homology with human frameworks. For E71, the homologous human sequences used were IGHV7-4-1 (SEQ ID NO: 2) for the heavy chain and IGKV-58 (SEQ ID NO: 4) for the light chain (FIG. 6). For E72, they were IGHV1-2*02|66.3|IGHJ4*01|85.7 (SEQ ID NO: 6) for the heavy chain and IGKV1-NL1*01|73.7|IGKJ2*02|81.8 (SEQ ID NO: 8) for the light chain, respectively (FIG. 7).

Figure 15:
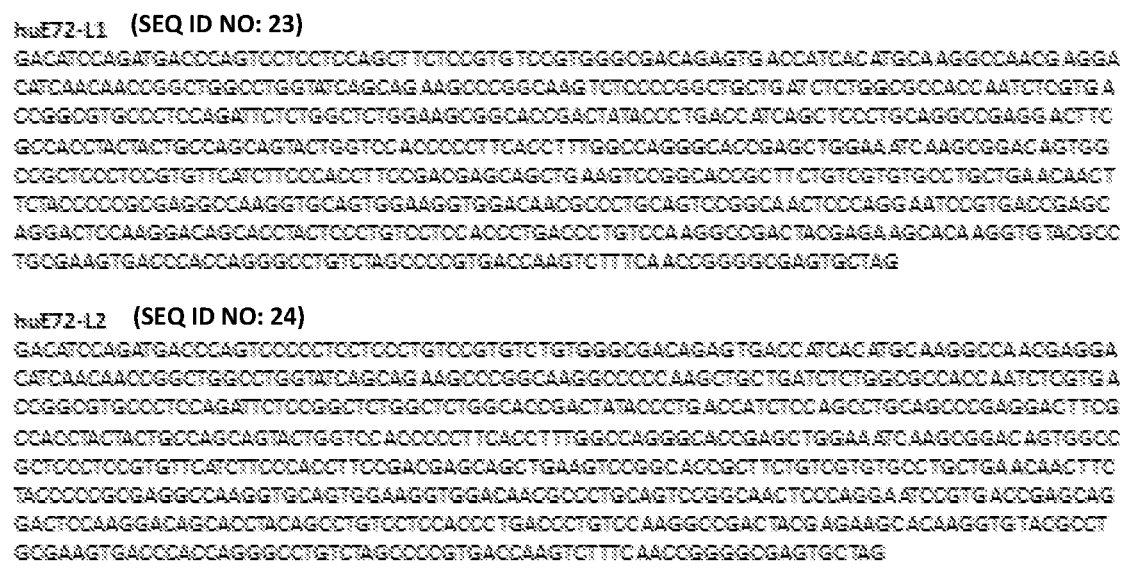

Two different heavy chain sequences (H1 and H2 for huE71; see FIG. 8 for corresponding amino acid sequences, and FIG. 9 for cDNA sequences) and two different light chain sequences (L1 and L2; FIG. 10 for corresponding amino acids, and FIG. 11 for cDNA sequences) were expressed as full IgGs for huE71 and tested for binding and stability. Two different heavy chain sequences (H1 and H2 for huE72; see FIG. 12 for corresponding amino acid sequences, and FIG. 13 for cDNA sequences) and two different light chain sequences (L1 and L2; see FIG. 14 for corresponding amino acid sequences, and FIG. 15 for cDNA sequences) were expressed as full IgGs for huE72 and tested for binding and stability.

The chimeric forms of E71 (FIG. 16 for corresponding amino acid sequences, and FIG. 17 for cDNA sequences) and E72 (FIG. 18 for corresponding amino acid sequences, and FIG. 19 for cDNA sequences) were also made for comparisons. The most stable combination H1 and L1 for E71 (FIG. 20 and FIG. 21, respectively) and H1 and L2 for E72 (FIG. 22 and FIG. 23, respectively) were chosen for the final form of huE71 and huE72 for the rest of the experiments. Additional constructs were made replacing the heavy chain sequences of chE71 with the human IgG4 framework (amino acid sequence in FIG. 24, and cDNA sequence in FIG. 25), and of huE71 with the human IgG4 framework (amino acid in FIG. 26 and cDNA in FIG. 27, respectively). HuE71 is packaged into a single vector (for balanced heavy chain and light chain secretion) transduced into DG44 cells. HuE71-IgG1n is another huE71-IgG1 glycoform expressed in CHO cells with variant glycosylation from a GnT1 deficiency (Jefferis R, *Nat Rev Drug Discov* 8:226-34 (2009)). HuE71-IgG1, huE71-IgG4 and huE71-IgG1n were purified using standard protein A affinity chromatography. Sugar analysis confirmed that huE71-IgG1n has 71.1% (Mol %) Mannose, 26.3% (Mol %)N-Acetyl Glucosamine, and 2.6% (Mol %) Glucose. On SDS gel, huE71 and huE72 migrated as IgG with the appropriate size heavy and light chains; and by HPLC, they all eluted as whole IgG with <5% aggregate formation.

Example 3: Antigen Binding of HuE71 and HuE72 and Derivatives Thereof

Figure 28:
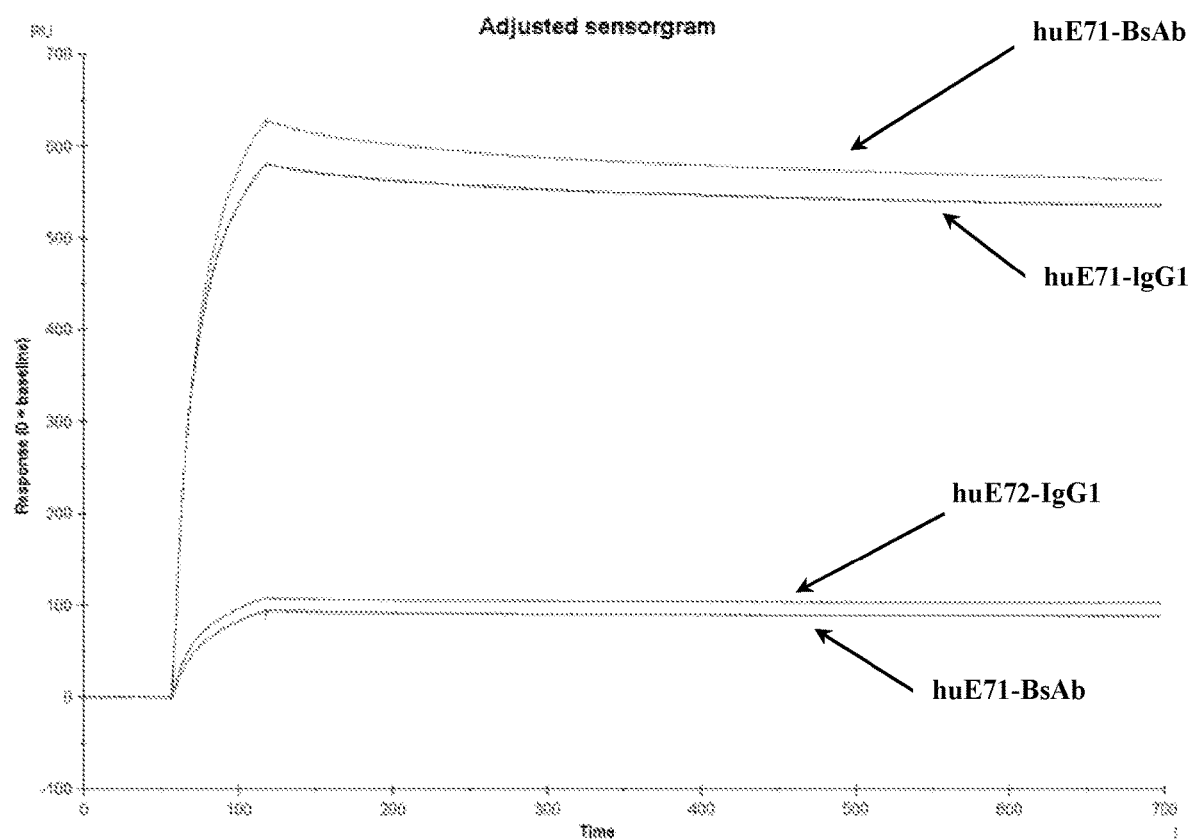
FIG. 28 shows the kinetics of humanized E71 or E72 IgG1s and BsAbs binding.

Antigen (L1-CAM-Fc and L1-CAM-His) was immobilized onto CM5 chips and kinetics of antibody binding ($k_{on}$, $k_{off}$ and $K_d$) were compared by surface plasma resonance (SPR) using Biacore T-100 (FIG. 28 for L1-CAM-Fc). Binding kinetics on L1-CAM-Fc for chimeric and humanized antibodies were summarized in FIG. 29 and FIG. 30, compared with other L1-CAM mouse antibodies. Binding kinetics on L1-CAM-His for chimeric and humanized antibodies are summarized in FIG. 31.

Antigen binding was also analyzed by FACS analysis using L1-CAM(+) tumor cells. Data were expressed as mean fluorescent intensity (MFI) determined by flow cytometry and normalized as percentage of binding of the highest concentration of antibody used (1 μg/$10^6$ cells): Mesothelioma (FIG. 32), leukemia, breast cancer and Ewings family of tumors (FIG. 33), and melanoma, neuroblastoma, osteosarcoma, rhabdomyosarcoma, small cell lung cancer (FIG. 34).

HuE71-IgG1 was stable, its EC50 of antigen binding remained 0.03 μg/million cells after being subjected to a 5 times freezing and thawing process. An ELISA method using tumor cells coated onto plastic plate as antigen was also used to assay huE71-IgG1 and huE71-IgG1n binding; both huE71-IgG1 and huE72-IgG1 showed comparable binding to tumor cells. Binding of huE71-IgG1n to tumor cells was unchanged after being subjected to repeated freezing and thawing for 5 times.

These results demonstrate that the antibodies of the present technology or antigen binding fragments thereof, specifically bind to L1-CAM with high binding affinity. Accordingly, the immunoglobulin-related compositions disclosed herein are useful for detecting L1-CAM protein in a sample.

Example 4: ADCC Mediated by HuE71-IgG1n and HuE72-IgG1n

Figure 61:
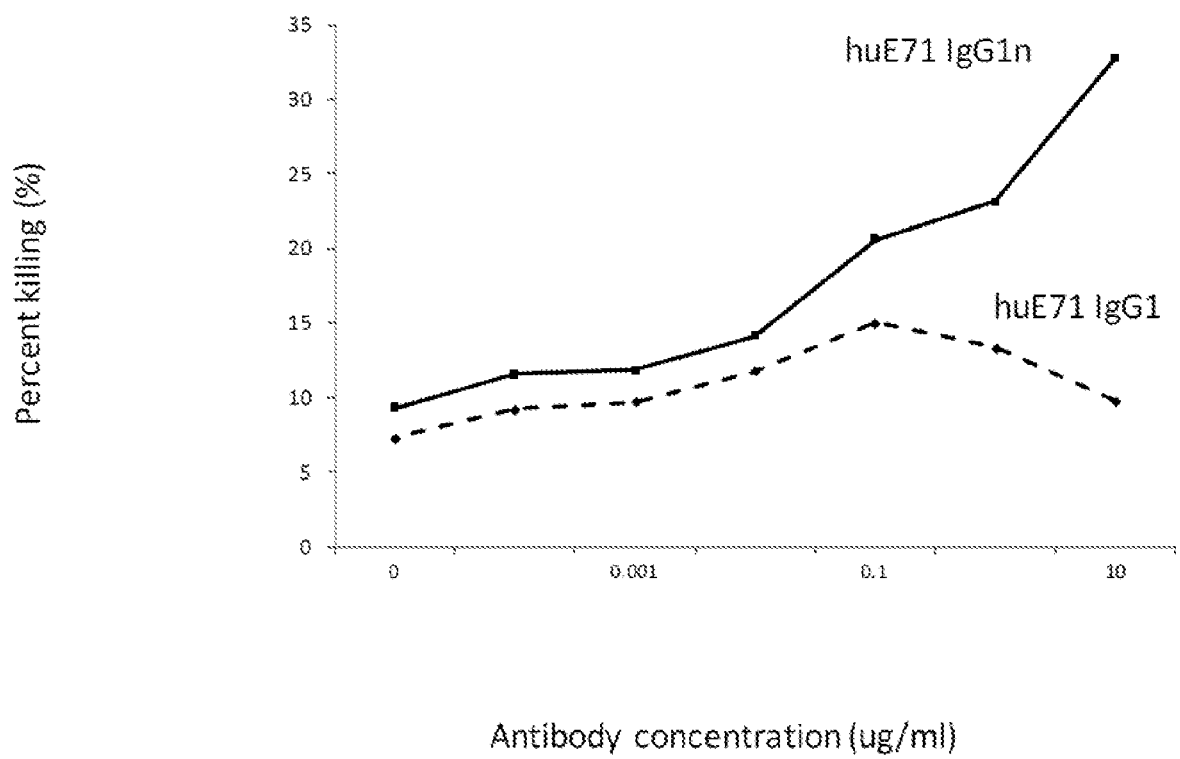
FIG. 61 shows that huE71-IgG1n mediates ADCC in LAN-1 cell line.
Figure 62:
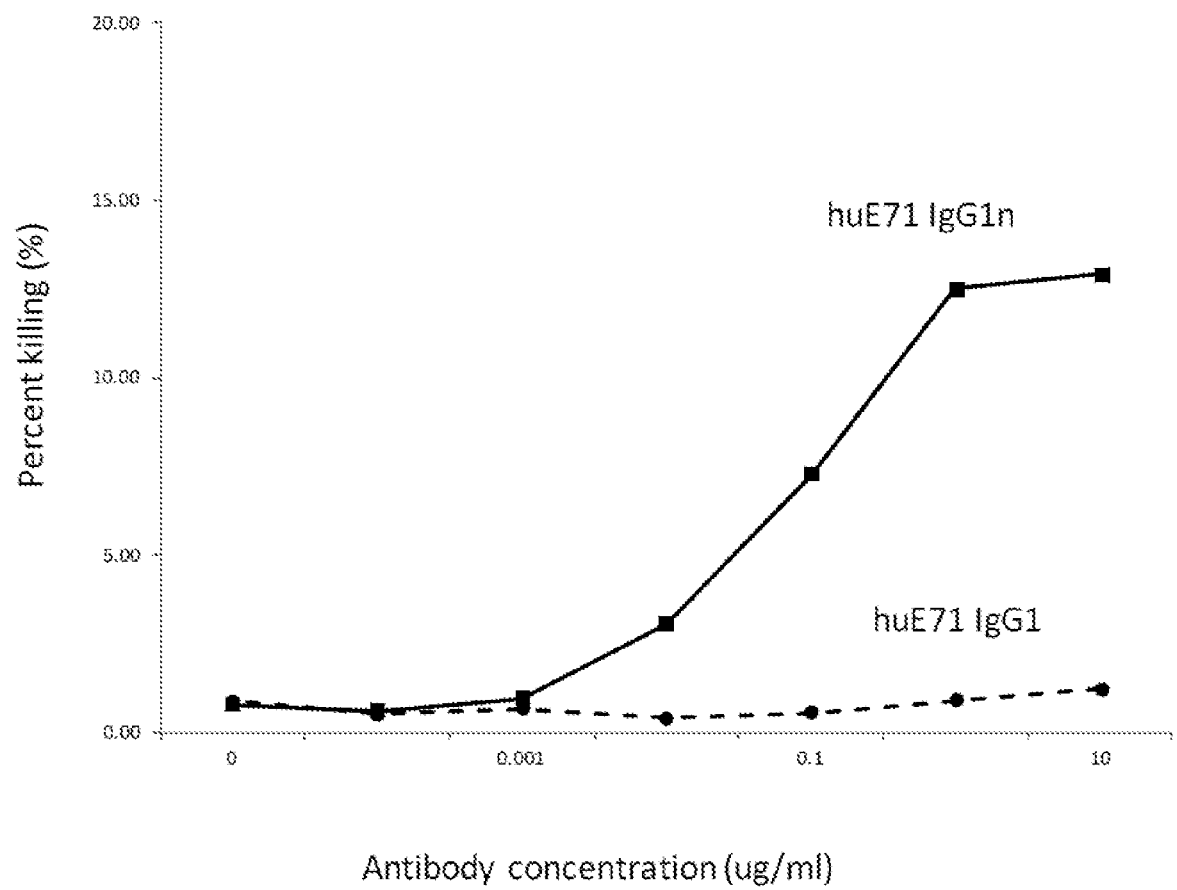
FIG. 62 shows that huE71-IgG1n mediates ADCC in NB1691 cell line.

ADCC (antibody-dependent cell-mediated cytotoxicity) was evaluated using PBMC as effectors from normal volunteers. In contrast to the special glycoforms, all the wild type human IgG1 forms of chE71, huE71, chE72 and huE72 cannot mediate ADCC. Two target cell lines LAN-1 and NB1691 were tested. Only huE71-IgG1n was able to mediate ADCC (EC50 for LAN-1 cells was 0.06 μg/ml, EC50 for NB1691 cells was 0.1 μg/ml). See FIGS. 61 and 62.

These results demonstrate that the antibodies of the present technology or antigen binding fragments thereof can elicit ADCC. Accordingly, the immunoglobulin-related compositions disclosed herein are useful for treating a L1-CAM-positive cancer.

Example 5: HuE71-BsAb and HuE72-BsAb Design and Expression in CHO-S Cells

Figure 35:
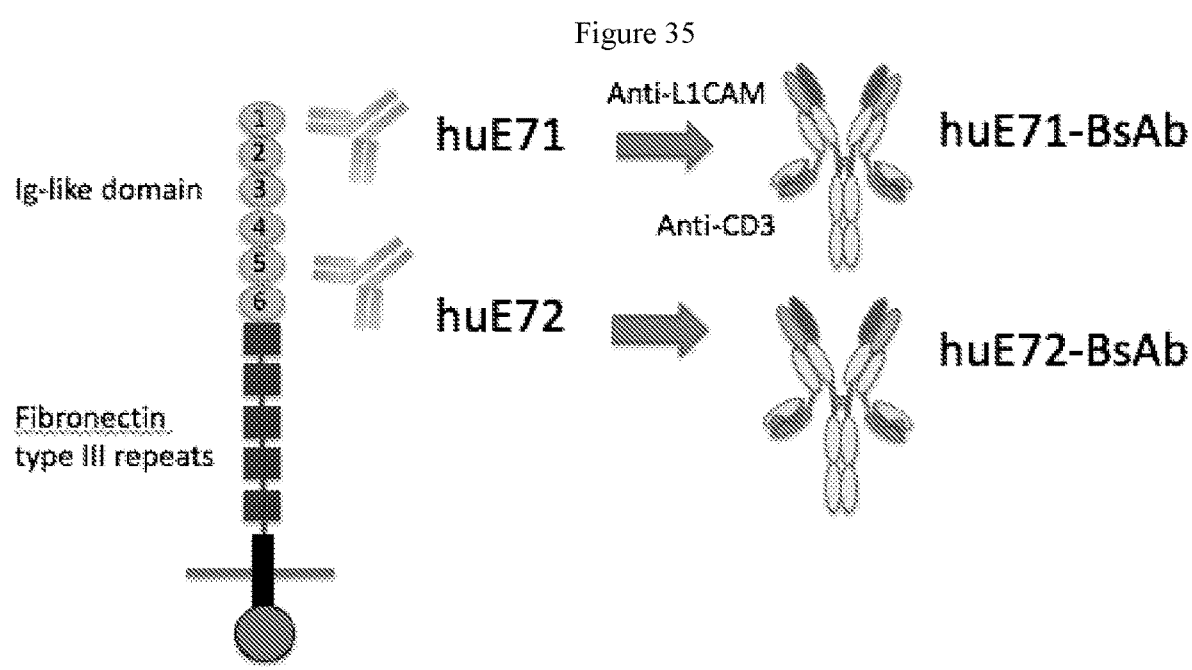
FIG. 35 shows the construction of the T-cell engaging bispecific antibodies (BsAb) for both huE71 and huE72.

BsAbs were designed using the IgG-scFv format (FIG. 35) with the amino acid sequences depicted in FIG. 36. For huE71-huOKT3 format, the heavy chain was identical to that of a huE71 IgG1, the light chain was constructed by extending a huE71 light chain with a C-terminal $(G_4S)_3$ linker (SEQ ID NO: 77) followed by huOKT3 scFv. HuE72-huOKT3 was similarly designed. For both antibodies, N297A and K322A mutations were introduced to hIgG1 Fc region to remove glycosylation and complement activation. The DNA encoding both the heavy chain and light chain of the BsAbs was inserted into a mammalian expression vector, transfected into CHO-S cells, and stable clones displaying the highest expression were selected. Supernatants were collected from shaker flasks and purified on protein A affinity chromatography. Proteins were further purified to >90% monomer by size exclusion chromatography.

Under reducing SDS-PAGE conditions, both BsAbs gave rise to two bands at around 50 KDa, since the huOKT3 scFv fusion to the light chain increased the MW to ~50 KDa. SEC-HPLC showed a major peak (97% by UV analysis) with an approximate MW of 210 KDa for both antibodies, as well as a minor peak of multimers removable by gel filtration. Affinity for L1-CAM for BsAbs were comparable to those of the parental IgGs, when assayed on L1-CAM-Fc by SPR (FIG. 37).

These results demonstrate that the antibodies of the present technology or antigen binding fragments thereof, specifically bind to L1-CAM with high binding affinity. Accordingly, the immunoglobulin-related compositions disclosed herein are useful for detecting L1-CAM protein in a sample.

Figure 38A:
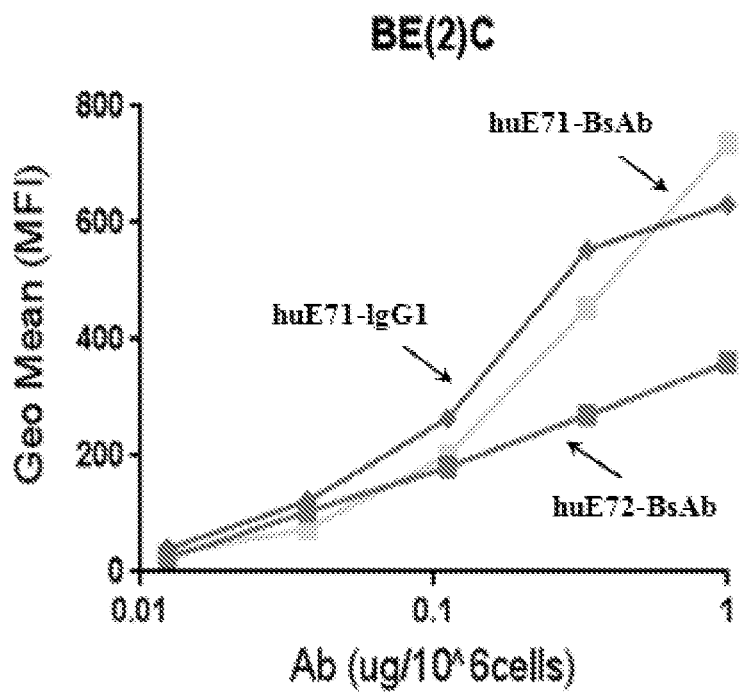
FIG. 38(A) shows the binding of humanized E71-BsAb and humanized E72-BsAb to L1-CAM (+) tumor cells.
Figure 38B:
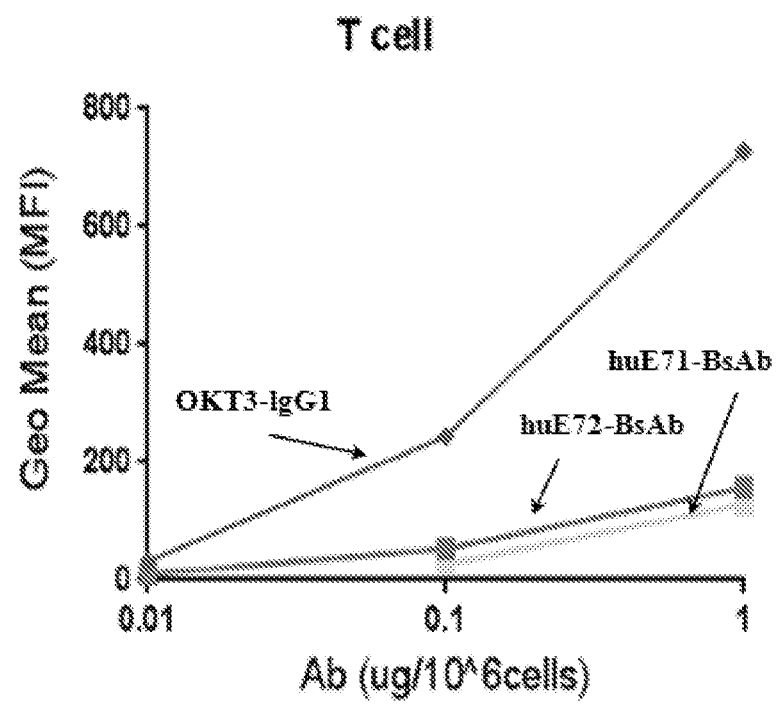
FIG. 38(B) shows the binding of humanized E71-BsAb and humanized E72-BsAb to T cells.
Figure 39A:
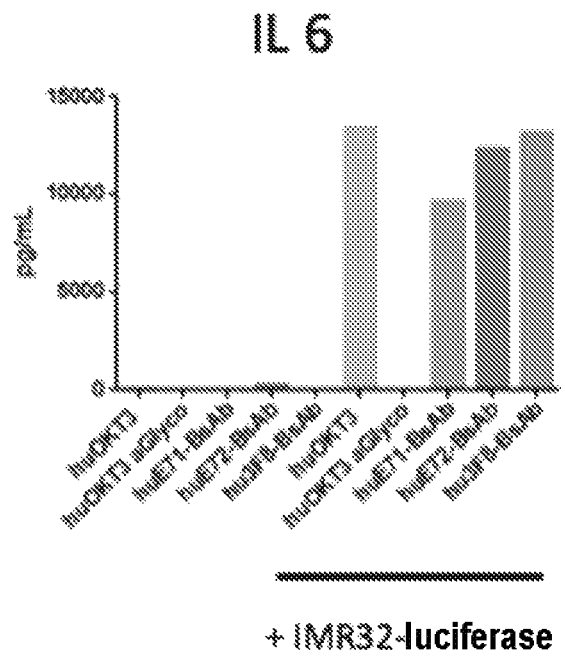
FIG. 39(A) shows the results of the IL-6 cytokine release assay for the antibodies of the present technology in the presence or absence of a L1-CAM (+) tumor cell line.
Figure 39B:
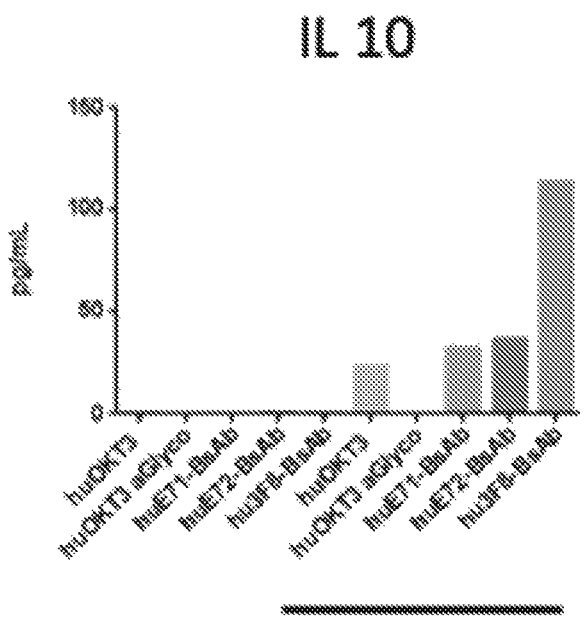
FIG. 39(B) shows the results of the IL-10 cytokine release assay for the antibodies of the present technology in the presence or absence of a L1-CAM (+) tumor cell line.
Figure 39C:
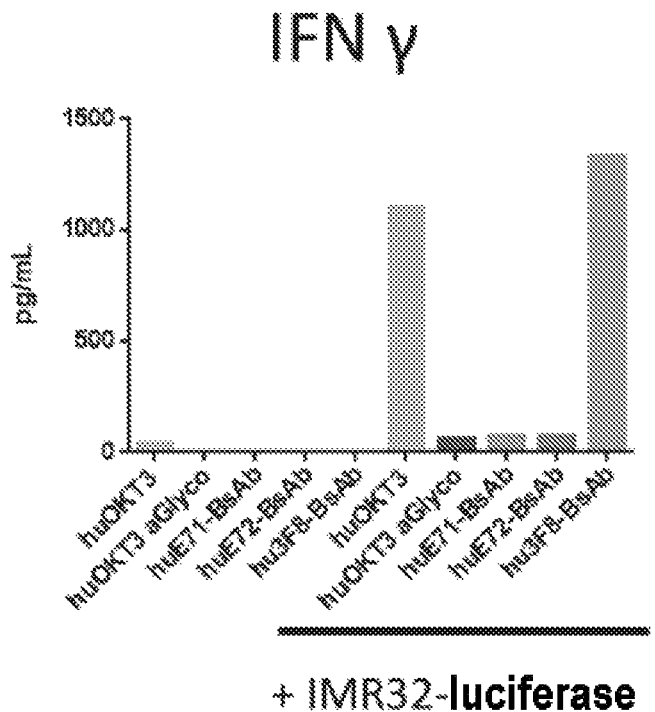
FIG. 39(C) shows the results of the IFN-γ cytokine release assay for the antibodies of the present technology in the presence or absence of a L1-CAM (+) tumor cell line.
Figure 39D:
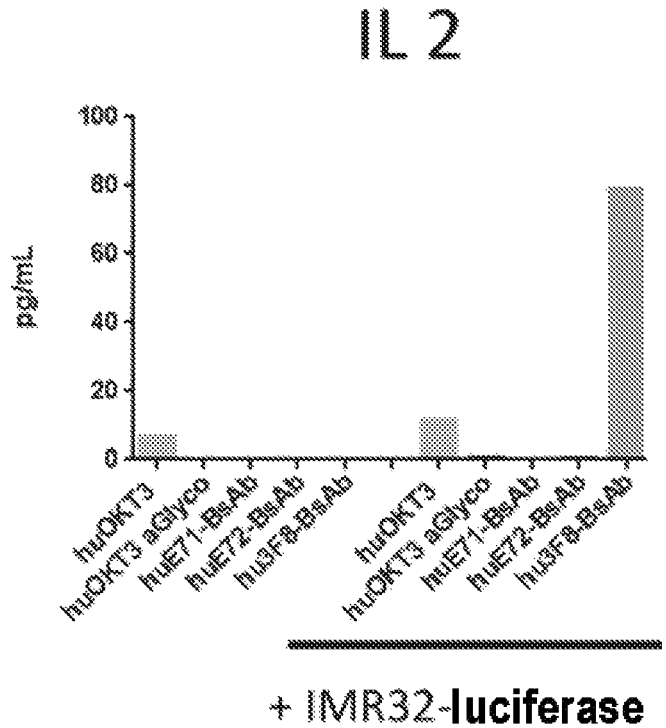
FIG. 39(D) shows the results of the IL-2 cytokine release assay for the antibodies of the present technology in the presence or absence of a L1-CAM (+) tumor cell line.
Figure 39E:
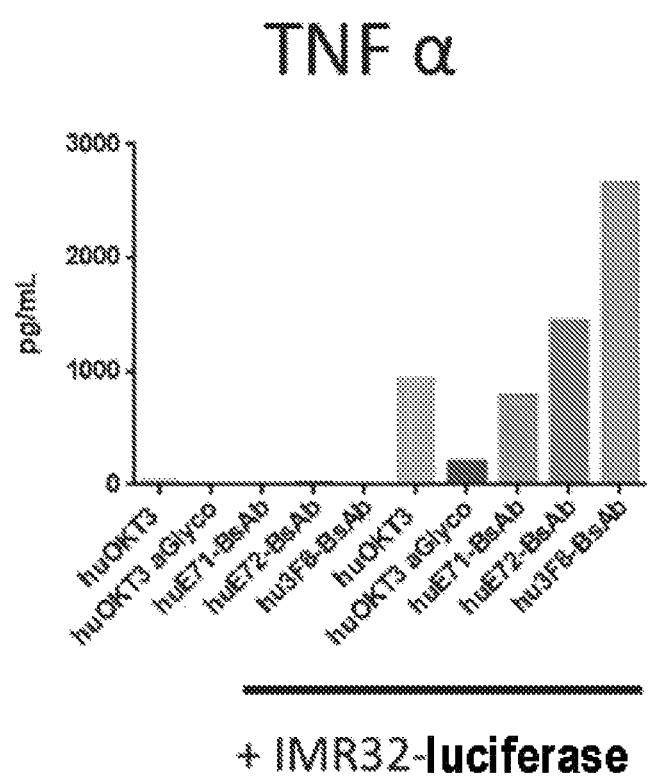
FIG. 39(E) shows the results of the TNF-α cytokine release assay for the antibodies of the present technology in the presence or absence of a L1-CAM (+) tumor cell line.

Example 6: Binding of Anti-L1-CAM BsAbs of the Present Technology to Both Tumor Cells and T Cells Binding kinetics by SPR on L1-CAM-Fc for both BsAbs are shown in FIGS. 28 and 37. The binding of huE71-BsAb and huE72-BsAb to both target cells and effector cells was tested by FACS immunostaining. huE71-BsAb was equally efficient as parental huE71 in binding to L1-CAM(+) neuroblastoma BE(2)C, whereas the binding of huE72-BsAb to BE(2)C was half of that observed with huE71-BsAb (FIG. 38(A)). For binding to CD3(+) T cells, both huE71-BsAb and huE72-BsAb were less efficient compared to huOKT3 IgG1; around 20 fold weaker than huOKT3 (FIG. 38(B)). The reduced avidity of the light chain-anchored scFv of the BsAbs for T cells was attributable in part to the spatial constraints of this format, but is advantageous for minimizing cytokine release especially when target cells were not present.

These data suggest that binding to CD3 was functionally monovalent, which precludes spontaneous activation of T cells in the absence of a tumor target.

Example 7: HuE71-BsAb or HuE72-BsAb Induced Th1 Cytokine Release

Both huE71-BsAb and huE72-BsAb induced release of Th1 cytokine such as TNFα from PBMCs after 24 hours of activation with the cell line IMR32-luciferase. IFNγ and 1L2 levels were relatively low. Both huE71-BsAb and huE72-BsAb also induced Th2 cytokine, IL6 and IL10 release. However, the levels of these cytokines were less than the ones induced by control hu3F8-BsAb (FIGS. 39(A)-(E)).

Figure 40:
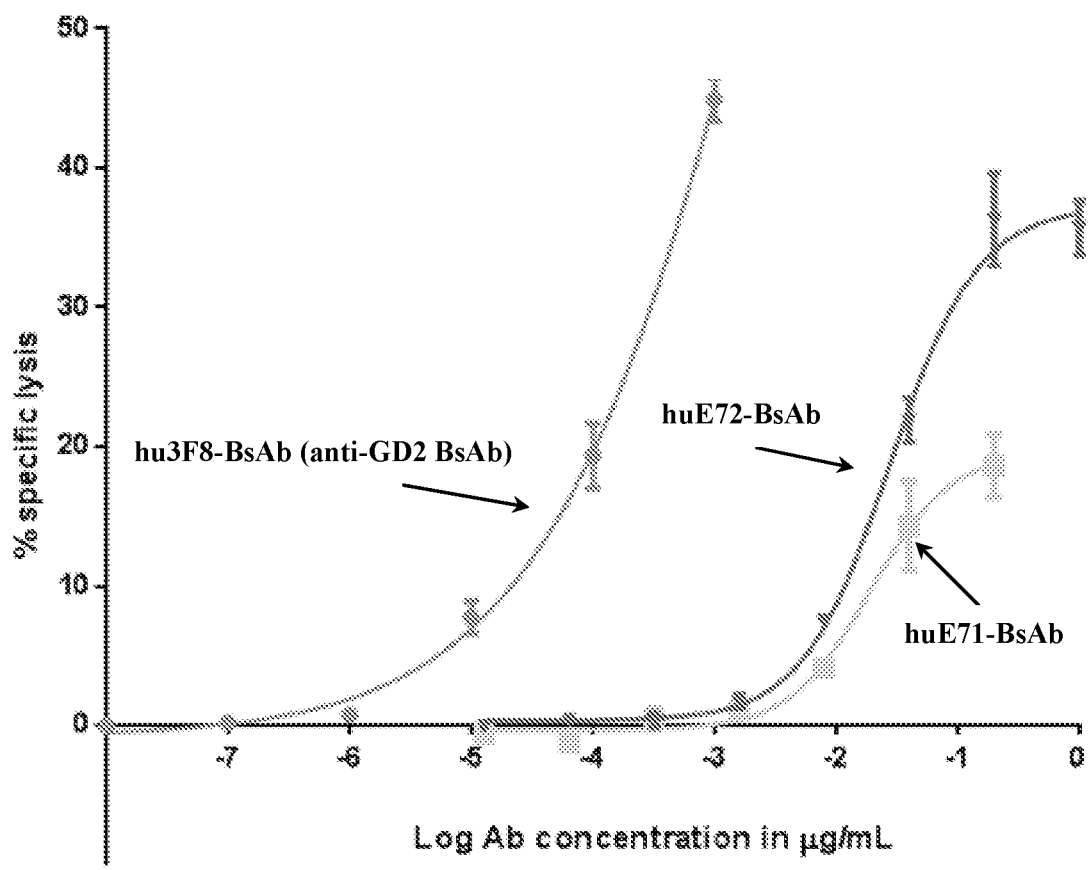
FIG. 40 shows the results of the $^{51}$chromium release assay. Humanized E71-BsAb or humanized E72-BsAb was incubated with T cells and IMR-32 luciferase cell line (E:T ratio=10:1) for 4 hours.
Figure 42A:
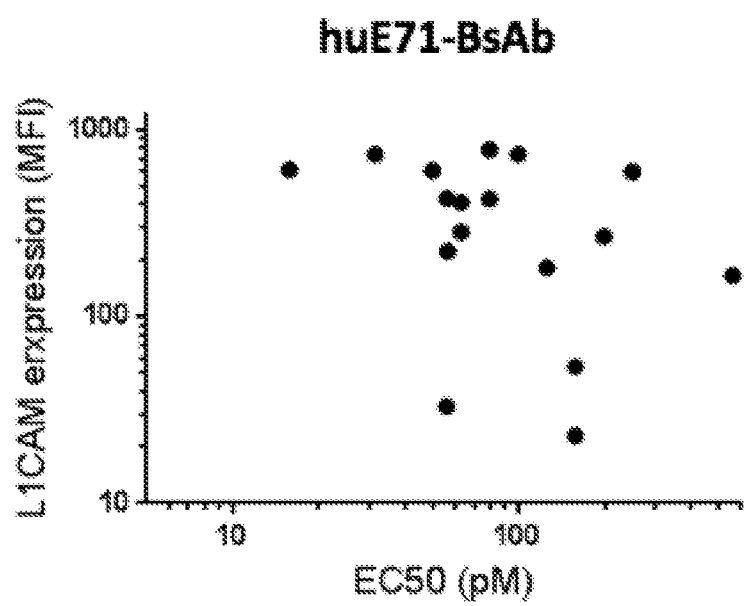
FIG. 42(A) shows that the cytotoxicity (EC50) of humanized E71-BsAb was inversely correlated with the L1-CAM expression of tumor cell lines (MFI).
Figure 42B:
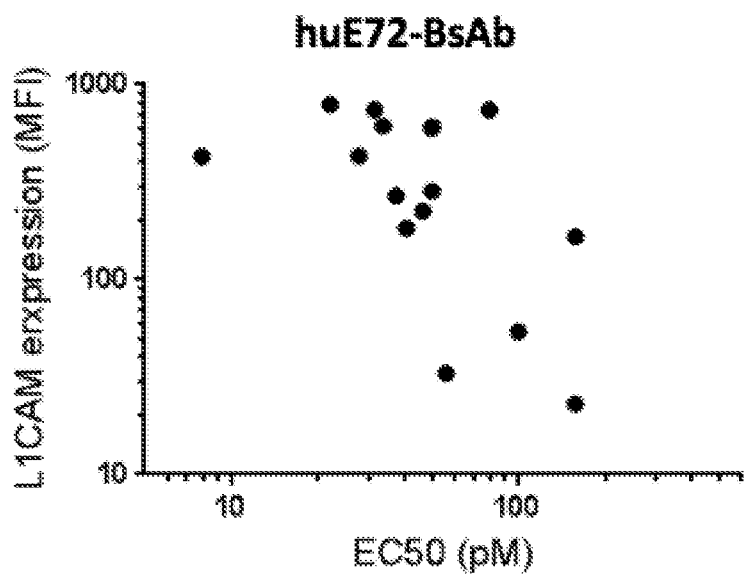
FIG. 42(B) shows that the cytotoxicity (EC50) of humanized E72-BsAb was inversely correlated with the L1-CAM expression of tumor cell lines (MFI).

Example 8: HuE71-BsAb and HuE72-BsAb Redirected T Cell Killing of Human Tumor Cell Lines HuE71-BsAb or huE72-BsAb mediated T cell cytotoxicity on L1-CAM positive cancer cell lines was tested in a standard 4-hour $^{51}$Cr release assays with activated T cells (E:T ratio=10:1). Both BsAbs induced T cell cytotoxicity against tumor cells, and huE72-BsAb was more potent than huE71-BsAb (EC50=50.0 pM and 62.9 pM respectively with IMR32-luciferase cell line) (FIG. 40). When an extended panel of human tumor cell lines (including neuroblastoma, melanoma, ovarian cancer, breast cancer, cervical adenocarcinoma) were tested, huE71-BsAb or huE72-BsAb mediated T cell cytotoxicity correlated with tumor L1-CAM expression as assessed by FACS (FIGS. 41 and 42(A)-42(B)).

Example 9: Efficacy of HuE71-BsAb and HuE72-BsAb Against Xenografts in Humanized Mice For in vivo therapy studies, BALB-Rag2-KO-IL-2R-γc-KO (DKO) mice (Koo G C et al., Expert Rev Vaccines 8:113-20 (2009); Andrade D et al., *Arthritis Rheum* 63:2764-73 (2011)) were used. In separate humanized mouse xenograft models (sc tumor plus sc effector cells, sc tumor plus iv effector cells), iv L1-CAM-BsAb showed high activity against established tumors in the presence of PBMCs from healthy donors.

Figure 43:
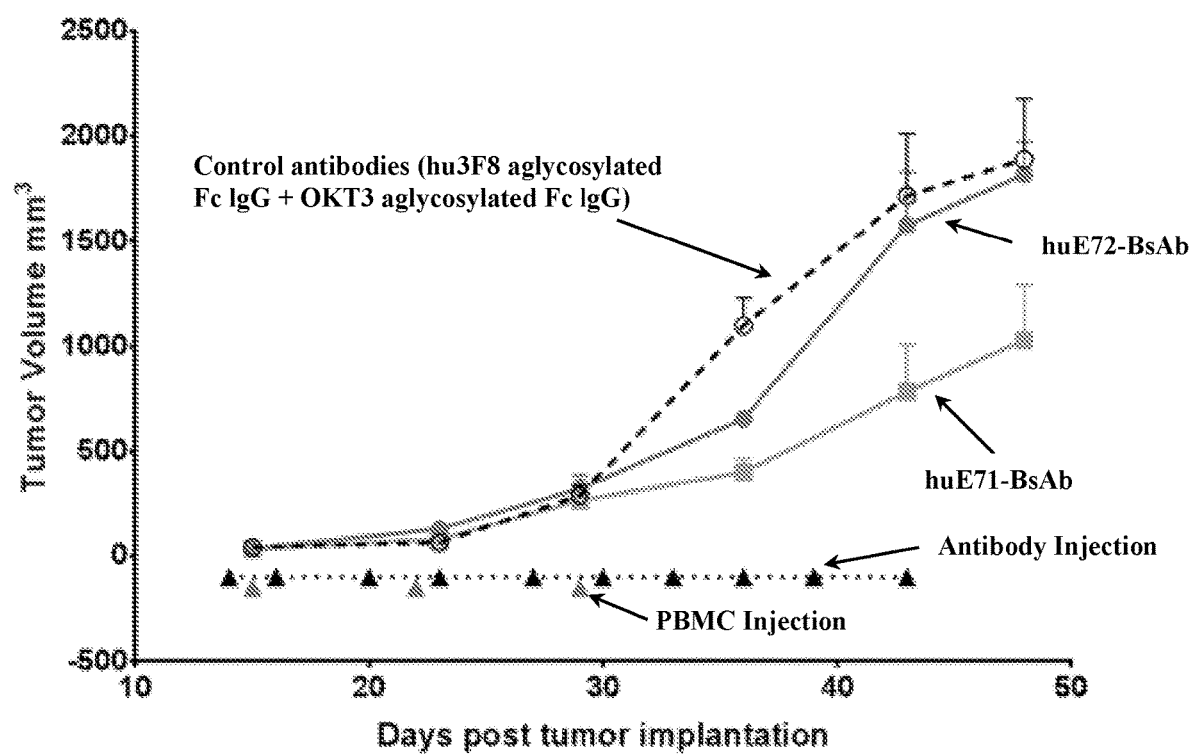
FIG. 43 shows the effects of huE71-BsAb and huE72-BsAb against neuroblastoma tumor in a humanized mouse model. L1-CAM (+) neuroblastoma patient derived xenograft (PDX) was transplanted in DKO mice subcutaneously. HuE71-BsAb or huE72-BsAb treatments were initiated on day 15, when tumors were measurable, using a dosing schedule of two injections per week for five weeks. PBMCs ($7.5\times10^6$) were administered intravenously starting on day 16, followed by weekly injections for 3 weeks. The size of the tumors was measured weekly. Mice treated with huE72-BsAb and PBMCs had tumor growth equivalent to control. HuE71-BsAb with PBMCs significantly suppressed tumor growth.

For in vivo studies, L1-CAM(+) neuroblastoma patient derived xenograft (PDX) (FIG. 43) was transplanted in DKO mice subcutaneously. HuE71-BsAb or huE72-BsAb treatments were initiated on day 15, when tumors were measurable, using a dosing schedule of two injections per week for five weeks. PBMCs ($7.5 \times 10^6$) were administered intravenously starting on day 16, followed by weekly injections for 3 weeks. The size of the tumors was measured weekly. Mice treated with huE72-BsAb and PBMCs had tumor growth equivalent to control. Thus, the in vivo anti-tumor response of huE72-BsAb was unremarkable despite its high binding affinity and superior in vitro tumor killing potency. In contrast, HuE71-BsAb with PBMCs significantly suppressed tumor growth.

Figure 44:
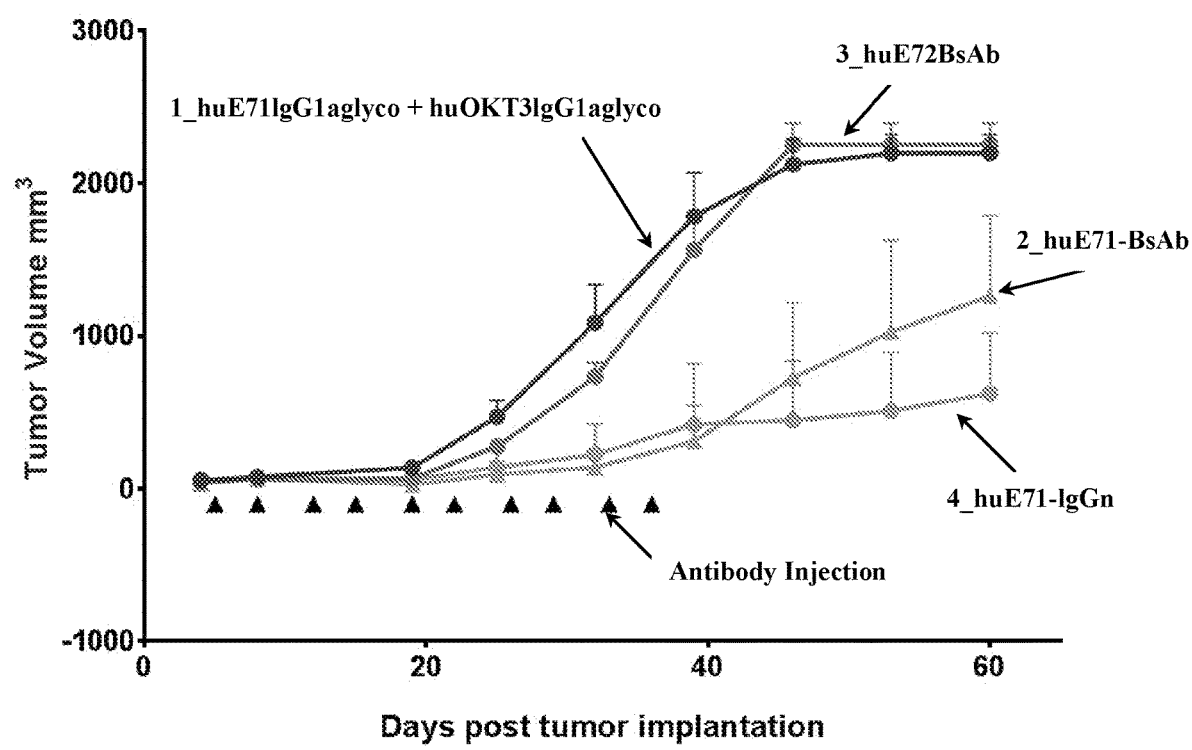
FIG. 44 shows the effects of huE71-BsAb and huE72-BsAb against neuroblastoma tumor in a humanized mouse model. L1-CAM (+) neuroblastoma cell line IMR32 was mixed with human PBMC and planted in DKO mice subcutaneously. HuE71-BsAb or huE72-BsAb treatments were initiated on day 5, when tumors were measurable, using a dosing schedule of two injections per week for five weeks. The size of the tumors was measured weekly. Mice treated with huE72-BsAb or control (aglycosylated huE71-IgG1+ aglycosylated huOKT3) had equivalent tumor growth. HuE71-BsAb or huE71-IgGn significantly suppressed tumor growth.

In FIG. 44, instead of PDX, the IMR32 neuroblastoma cell line was used and planted subcutaneously mixing with an equal number of PBMC. HuE71-BsAb or huE71-IgGn significantly suppressed tumor growth, whereas huE72-BsAb had no effect on tumor volume.

Example 10: Tumor Imaging Using $^{89}$Zr-huE71-IgG1n and $^{89}$Zr-huE72-IgG1n

Figure 45:
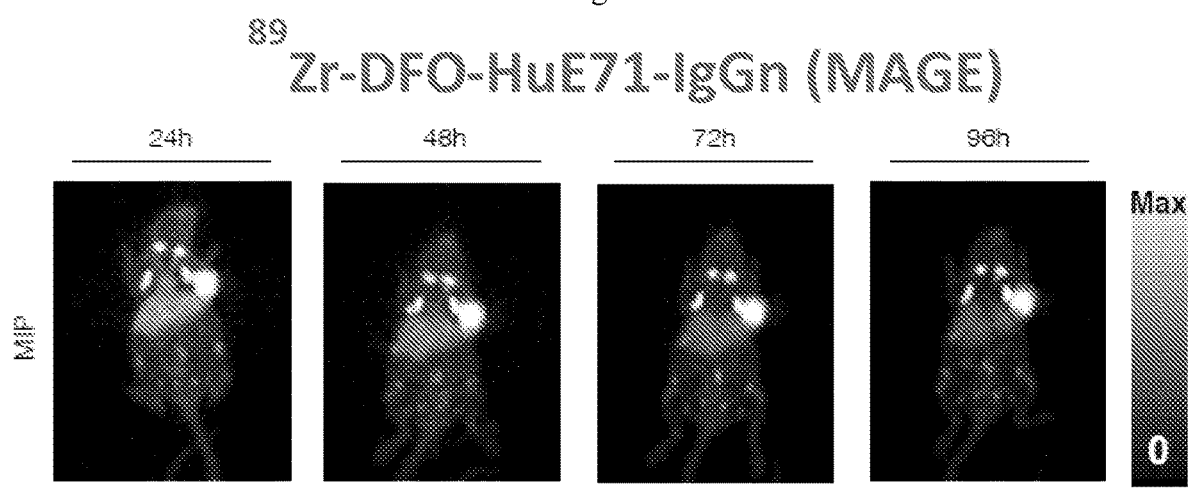
FIG. 45 shows serial PET imaging of $^{89}$Zr-HuE71-IgGn (MAGE). Small-animal PET imaging in a subcutaneous ovarian cancer tumor model revealed high tumor and lymph node activity concentration. Representative maximal intensity projection (MIP) PET images of $^{89}$Zr-HuE71-1 MAGE (192-197 µCi in 150 µL of PBS injected via tail vein) in athymic nude mice bearing subcutaneous SKOV-3 tumors xenografted on the right shoulder. Selective tumor uptake was early at 24 hours and persistently improved through 96 hours.
Figure 46:
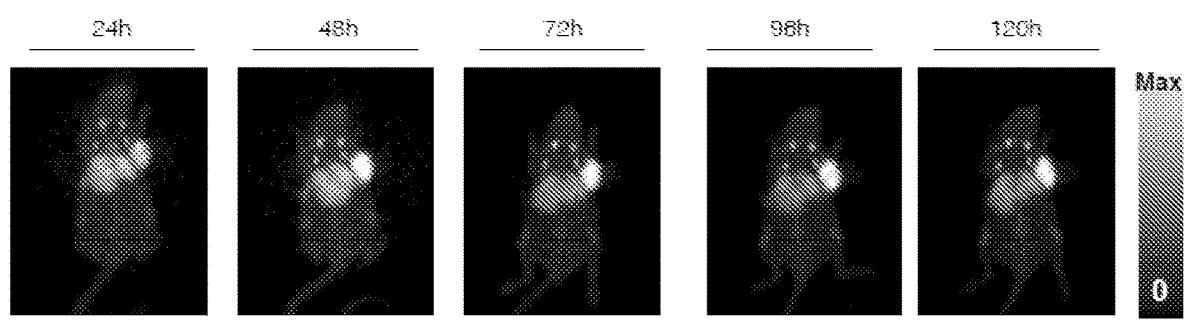
FIG. 46 shows Serial PET imaging of $^{89}$Zr-HuE72-IgGn (MAGE). Small-animal PET imaging in a subcutaneous ovarian cancer tumor model revealed high tumor and lymph node activity concentration. Representative maximal intensity projection (MIP) PET images of $^{89}$Zr-HuE72-IgGn (MAGE) (~200 µCi in 150 µL of PBS injected via tail vein) in athymic nude mice bearing subcutaneous SKOV-3 tumors xenografted on the right shoulder. Selective tumor uptake was suboptimal at 24 hours; it did improve overtime.
Figure 48A:
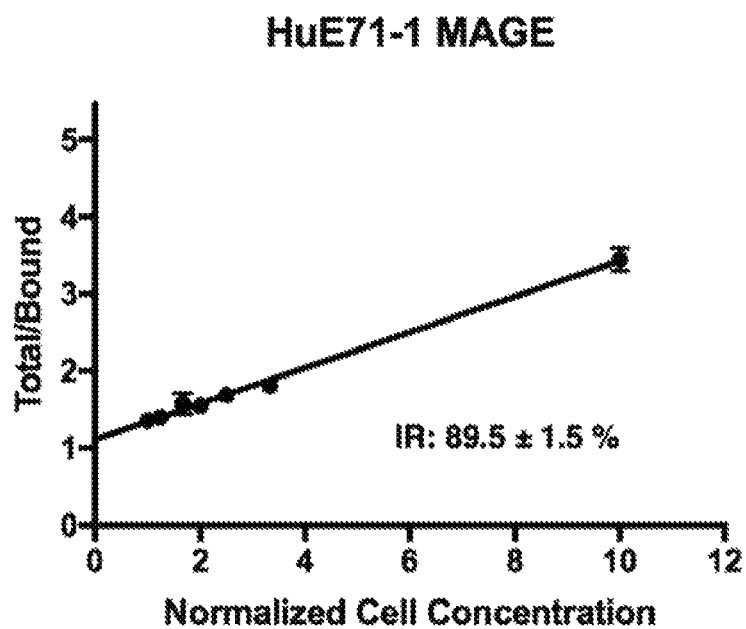
FIGS. 48(A)-48(E) show the immunoreactivity of $^{89}$Zr-radiolabeled L1-CAM antibodies of the present technology. The radioimmunoconjugates were functionally characterized for binding to antigen-expressing cells (SKOV-3) and the determination of the immunoreactive fraction via Lindmo assays (Ben Q W et al., *Ann Surg Oncol* 17:2213-21 (2010)). Aliquots of each radioimmunoconjugate, 50 µL of 1 µCi/mL stock were added to tubes containing $5.0\times10^5$-$5.0\times10^6$ cells/mL (in triplicate) in 500 µL PBS, 1% BSA (pH 7.4 to a final volume of 550 µL). Cell bound activity was counted and data graphed on double-reciprocal plot. Immunoreactive fractions are presented as mean percentages of triplicate samples±SEM.
Figure 48B:
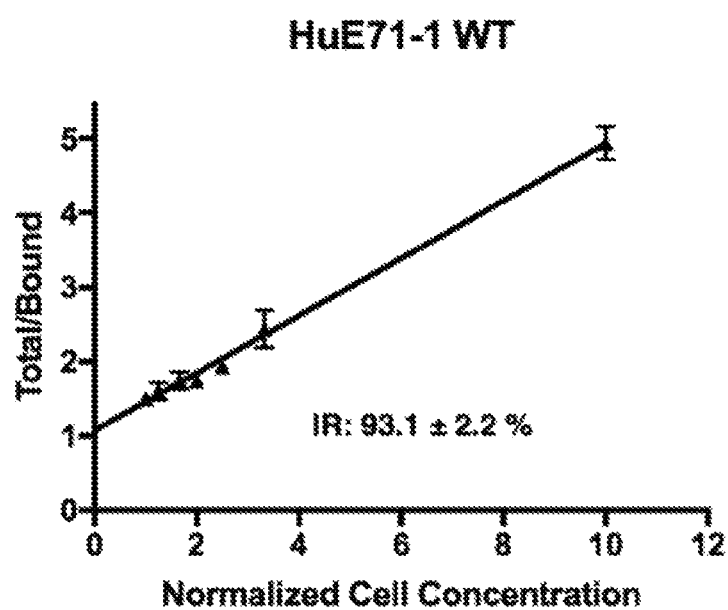
Figure 48C:
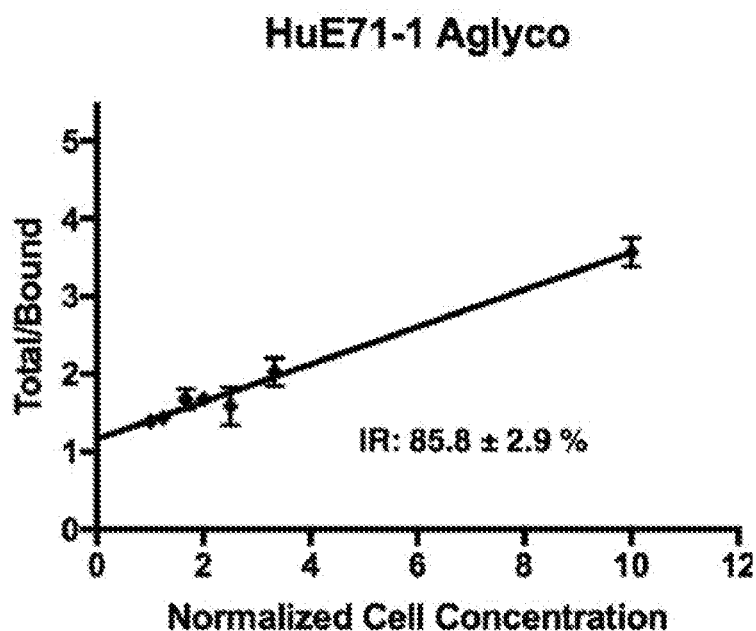
Figure 48D:
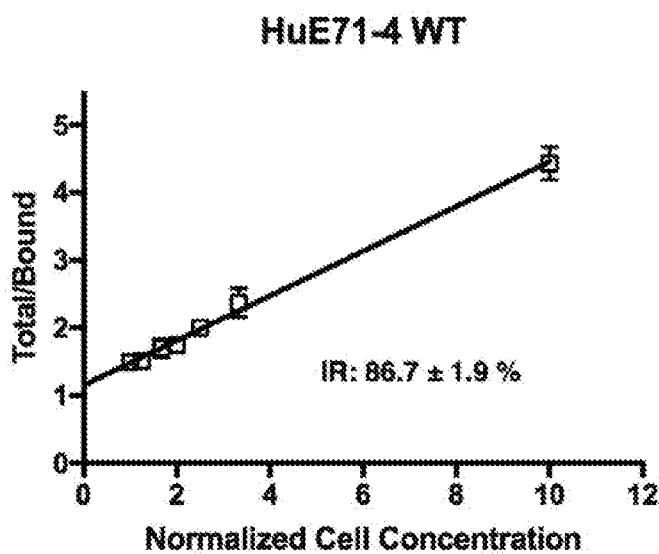
Figure 48E:
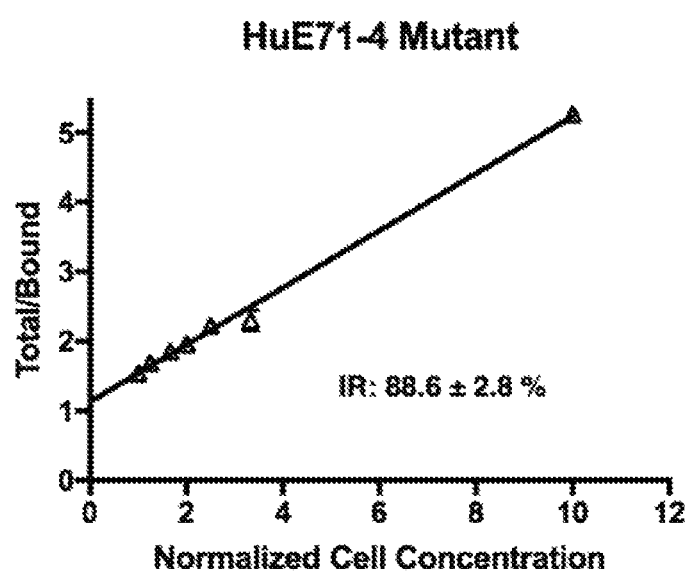

Nude mice planted with SKOV3 human ovarian xenograft sc were imaged with $^{89}$Zr-huE71-IgG1n and $^{89}$Zr-huE72-IgG1n (FIG. 45 and FIG. 46, respectively). Despite the lower affinity of huE71 compared to huE72, the in vivo targeting efficiency of $^{89}$Zr-huE71-IgG1n was superior.

Example 11: L1-CAM Antibody Fc Variants

The following studies evaluate the effect of modifications within in the Fc region of humanized antibodies on their in vivo biodistribution. There are four subclasses of IgG antibodies (IgG1, IgG2, IgG3, and IgG4) in humans, which can be broken down into further subtypes. In addition, there are several types of Fc receptors that bind IgG antibodies, i.e., Fc gamma receptors.

The Fc gamma receptors are further subdivided into classes that are differentially expressed on immune cells with Fc gamma receptor I having the highest affinity for IgG antibodies (Nimmerjahn F, Ravetch J V. *Nat Rev Immunol* 8:34-47 (2008)). IgG1 antibodies are the most abundant in humans and have the highest affinity for activating Fc gamma receptors (Bruhns P et al., *Blood* 113:3716-25 (2009)). In addition, the sugar moieties, or glycosylation state, of IgGs play a large role in the binding to Fc gamma receptors. Specifically, for IgG1 antibodies, the sugar moieties attached to the N297 residue on the constant region interact with and alter Fc binding characteristics of the antibody (Sazinsky S L et al., *Proc Natl Acad Sci USA* 105:20167-72 (2008)). The complex sugar moieties attached to this residue include mannose and N-acetylglucosamine (GlcNAc) along with other branching sugars including fucose, galactose, and sialic acid and alteration of this glycosylation site can dramatically affect binding (Maverakis E et al., *J Autoimmun* 57:1-13 (2015); Arnold J N et al., *Annu Rev Immunol* 25:21-50 (2007). IgG antibodies with an entire deletion of these sugars demonstrate significantly reduced Fc gamma receptor binding without affecting their FcR(n) affinity. On the other hand, removal of fucose residues from the glycosylation site greatly increases the affinity of the IgG for the Fc gamma receptor (Maverakis E et al., *J Autoimmun* 57:1-13 (2015). While IgG1 antibodies have the highest affinity for Fc gamma receptor, IgG4 antibodies, which represent the least abundant IgG in humans, have a significantly lower affinity for the Fc gamma receptor and is generally viewed as an anti-inflammatory IgG that dampens immune responses as a regulatory mechanism. Without wishing to be bound by theory, it is believed that this phenomena is due, in part, to the intrinsic property of IgG4 antibodies known as dynamic Fab arm exchange (Van der Neut Kolfschoten M et al., *Science* 317:1554-7 (2007)).

All the subclasses of IgG antibodies are composed of two heavy-light chain pairs that are bound together by disulfide bonds made by cysteine residues on the heavy chain located in the hinge region of the antibody. This hinge region is variable in length, along with the number of disulfide bonds, depending on the subclass of the IgG. These characteristics influence the flexibility of the hinge region and play a role in the binding affinities to the Fc gamma receptor (Rispens T, et al., *J Biol Chem* 289:6098-109 (2014)). With IgG4 antibodies, the two half-molecules (heavy-light chain pair) are able to disassociate with one another at the hinge region and recombine spontaneously with other half-molecules to form bispecific, monovalent antibodies in vitro and in vivo (Rispens T, et al., *J Biol Chem* 289:6098-109 (2014); Vidarsson G et al., *Front Immunol* 5:520 (2014)). This dynamic Fab arm exchange property can be disabled in IgG4 antibodies by the introduction of a serine to proline mutation (S228P) within the hinge region of the antibody (Silva J P et al., *J Biol Chem* 290:5462-9 (2015)). The experiments performed in this study utilize humanized antibodies in mice expressing mouse Fc gamma receptors. Although the Fc gamma receptors in man and mouse are only 60-70% homologous, recent studies have shown that human IgGs bind to the orthologous mouse Fc gamma receptors with very similar affinities suggesting similar biological activities (Overdijk M B et al., *J Immunol* 189:3430-8 (2012)).

L1-CAM Antibody Modifications.

In order to investigate the effects of the Fc region on the in vivo biodistribution of radioimmunoconjugates, a panel of humanized IgG1 and IgG4 antibodies was developed, all of which have the exact same antigen binding site, but have modifications in the Fc region, thus altering their affinity for the Fc gamma receptors (FIG. 47). HuE71-1 MAGE is an IgG1 antibody against L1-CAM with glycans lacking α-1, 6-fucose that was produced in CHO cells that have a deficiency in the enzyme, UDP-N-acetylglucosamine: α-3-d-mannoside-β-1,2-N-acetylglucosaminyltransferase I (GnT1), thus enhancing the Fc region (Xu H et al., *Cancer Immunol Res* 4:631-8 (2016)). HuE71-1 WT is the wild-type IgG1 antibody against L1-CAM produced in wild-type CHO cells, while HuE71-1 Aglyco is the aglycosylated variant that contains a N297A mutation diminishing its Fc gamma receptor binding. HuE71-4 WT is the IgG4 variant of this antibody while HuE71-4 Mutant contains a S228P mutation which prevents dynamic Fab arm exchange from occurring. Finally, HuCtrl-4 is an IgG4 wild-type antibody targeting GD2, a non-specific antigen in the animal model used for this study.

Conjugation and Radiolabeling.

For conjugation of the L1-CAM antibodies disclosed herein to functionalized isothiocyanate desferrioxamine chelator (p-SCN-Bn-DFO), a concentrated solution of each antibody dissolved in PBS was pH adjusted to 8.5-9 and incubated with the chelator dissolved in DMSO at a 10:1 molar excess for 1 hour at 37° C. Following spin filter purification of the antibodies (Amicon Ultra 50 kDa), aliquots were frozen and samples of the starting material (unconjugated antibody) and the conjugated antibodies were evaluated using matrix-assisted laser desorption/ionization time of flight mass spectrometry (MALDI-ToF MS) to determine the chelate number for each antibody. Because a non-specific conjugation method was used, it was possible for DFO moieties to form multiple thiourea linkages on lysine residues distributed randomly on the antibodies. MALDI-ToF MS analysis of the pre-conjugated and post-conjugated antibodies revealed values of 2.38 chelates per $^{89}$Zr-HuE71-1 MAGE, 1.41 chelates per $^{89}$Zr-HuE71-1 WT, 1.07 chelates per $^{89}$Zr-HuE71-1 Aglyco, 1.30 chelates per $^{89}$Zr-HuE71-4 WT, 0.63 chelates per $^{89}$Zr-HuE71-4 Mutant, and 1.12 chelates per $^{89}$Zr-HuCtrl-4 WT. These values represent the average number of chelates per antibody molecule. For example, a value of 1.41 DFO chelate molecules per $^{89}$Zr-HuE71-1 WT indicates that each antibody molecule has 1 or 2 chelators bound. Each of the antibodies was then radiolabeled with $^{89}$Zr in PBS for 60 minutes at 37° C.

Radiochemical yields and specific activities were calculated using instant thin layer chromatography (ITLC) with a mobile phase of EDTA (pH 5.0, 50 mM) where the free $^{89}$Zr migrates with the solvent front and the chelated $^{89}$Zr remains at the baseline. Radiochemical yields for all of the antibodies were greater than 95% and the radiochemical purities for all of the antibodies were greater than 99% following size exclusion chromatography purification (PD-10 column). Specific activities for all of the antibodies (excluding $^{89}$Zr-HuE71-4 Mutant) were between 6.18-6.89 µCi/g post-radiolabeling. Despite many attempts at optimizing the radiolabeling of $^{89}$Zr-HuE71-4 Mutant, a specific activity above 2.14 µCi/g was never achieved, which consistent with the MALDI-ToF MS data which demonstrated that $^{89}$Zr-HuE71-4 Mutant had the lowest average chelate number of 0.63.

In Vitro Characterization.

In order to assess the radiochemical stability of the tracers, a serum stability challenge was performed. A small aliquot (100 uL) of each radioimmunoconjugate was incubated in human serum (900 µL) at 37° C. through seven days. Samples were taken on days 0, 1, 3, 5 and 7 and evaluated via radio instant thin layer chromatography to determine the percentage of activity remaining bound to the antibody. The study revealed that all of the tracers were stable throughout seven days with values of 97.3±0.8% for $^{89}$Zr-HuE71-1 MAGE, 97.7±0.7% for $^{89}$Zr-HuE71-1 WT, 96.6±0.8% for $^{89}$Zr-HuE71-1 Aglyco, 96.9±0.3% for $^{89}$Zr-HuE71-4 WT, 97.5±0.3% for $^{89}$Zr-HuE71-4 Mutant, and 96.7±1.1% for $^{89}$Zr-HuCtrl-4 WT. These values, all above 95% intact through seven days are in line with what was expected for a $^{89}$Zr-DFO radiolabeled antibody.

To determine the extent to which these antibodies were able to bind the target post-radiolabeling, immunoreactivity assays were performed. Briefly, the $^{89}$Zr-labeled antibodies were incubated with increasing concentrations of target positive ovarian cancer cells (SKOV3) and, following washes, the cell bound activity was counted and used to calculate the immunoreactive fraction. These experiments yielded immunoreactivities greater than 85% for all the antibodies, specifically, 89.5±1.5% for $^{89}$Zr-HuE71-1 MAGE, 93.1±2.2% for $^{89}$Zr-HuE71-1 WT, 85.8±2.9% for $^{89}$Zr-HuE71-1 Aglyco, 86.7±1.9% for $^{89}$Zr-HuE71-4 WT and 88.6±2.8% for $^{89}$Zr-HuE71-4 Mutant (FIGS. 48(A)-48(E)). Because the immunoreactivities of all of the tracers are within range of each other, one may assume that any observable differences in the pattern of imaging and biodistribution of the radioimmunoconjugates are not due to differences in their binding ability to the target antigen (L1-CAM).

Serial PET Imaging.

Serial PET imaging studies on female nude athymic mice bearing subcutaneous SKOV3 tumors on the right shoulder were performed to determine how modifications to the Fc region of the antibodies of the present technology would alter the biodistribution pattern of these radioimmunoconjugates. The radiolabeled immunoconjugates were injected via the tail vein and PET images were acquired at 4 time points post-injection (24, 48, 72 and 96 hours). Presented in all of the imaging figures are coronal slices of the mice through the tumor tissue (all scaled from 0 to 30% injected dose per gram) and maximal intensity projections (MIP) representing the total body image.

Figure 49:
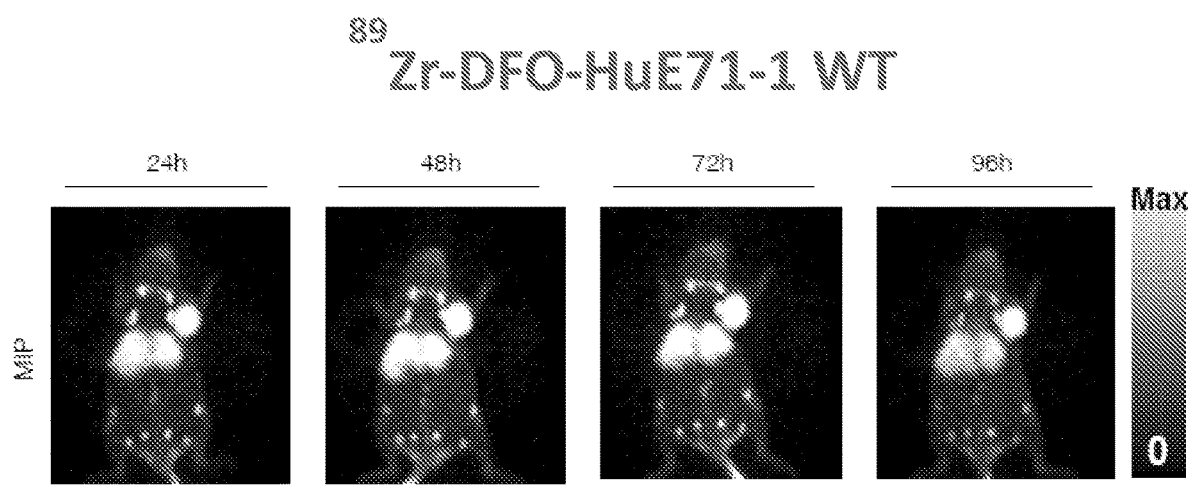
FIG. 49 shows the serial PET imaging of $^{89}$Zr-HuE71-1 WT antibody. Small-animal PET imaging in a subcutaneous ovarian cancer tumor model revealed high tumor, liver and lymph node activity concentration. Representative maximal intensity projection (MIP) PET images of $^{89}$Zr-HuE71-1 WT (194-201 µCi in 150 µL of PBS injected via tail vein) in athymic nude mice bearing subcutaneous L1-CAM-positive SKOV-3 tumors xenografted on the right shoulder.

For $^{89}$Zr-HuE71-1 MAGE (FIG. 45), high radioactivity concentration of the tracer in the tumor tissue (white arrow) with minimal radioactivity in the non-targeted organs was observed at 24 hours post-injection. The tracer cleared rapidly from the blood pool as no heart or large blood vessels can be seen. Interestingly, four bilateral structures within the upper portion of the animal (gray arrow) appeared to have high radioactive concentration as well. These PET-positive tissues were harvested and identified them as the submandibular and axillary lymph nodes. Further, the lymph node uptake with $^{89}$Zr-HuE71-1 MAGE persisted up to 96 hours post-injection of the radiotracer. PET images of SKOV-3 xenografts injected with $^{89}$Zr-HuE71-1 WT revealed high tracer uptake within the tumor tissue at 24 hours which continued to accumulate up to 96 hours (FIG. 49). There was high liver radioactivity concentration that was quite intense at 24 hours then gradually washes out slightly through 96 hours. Once again, the four lymph nodes in the upper portion of the mouse were illuminated on PET at 24 hours, as well as the lower lymph nodes, but they appeared to fade slightly through 96 hours.

Figure 50:
FIG. 50 shows the serial PET imaging of $^{89}$Zr-HuE71-1 Aglyco antibody. Small-animal PET imaging in a subcutaneous ovarian cancer tumor model revealed high tumor and very low background activity concentration. Representative maximal intensity projection (MIP) PET images of $^{89}$Zr-HuE71-1 Aglyco (207-214 µCi in 150 µL of PBS injected via tail vein) in athymic nude mice bearing subcutaneous L1-CAM-SKOV-3 tumors xenografted on the right shoulder.

In the $^{89}$Zr-HuE71-1 Aglyco images (FIG. 50), high radioactivity concentration of the tracer within the tumor tissue at 24 hours was observed, which continued to accumulate up to 96 hours. Blood pool activity with this tracer was quite high and clearly visible at 24 hours in the heart, descending aorta, and right and left common carotid arteries but this activity cleared out rapidly by 72 hours post-injection. Based on the PET imaging data of the IgG1 radiolabeled antibodies, $^{89}$Zr-HuE71-1 Aglyco has the cleanest biodistribution profile, in that the tumor tissue had the highest radioactivity concentration with the least amount of non-targeted tissue activity from 24 hours post-injection to 96 hours.

Figure 51:
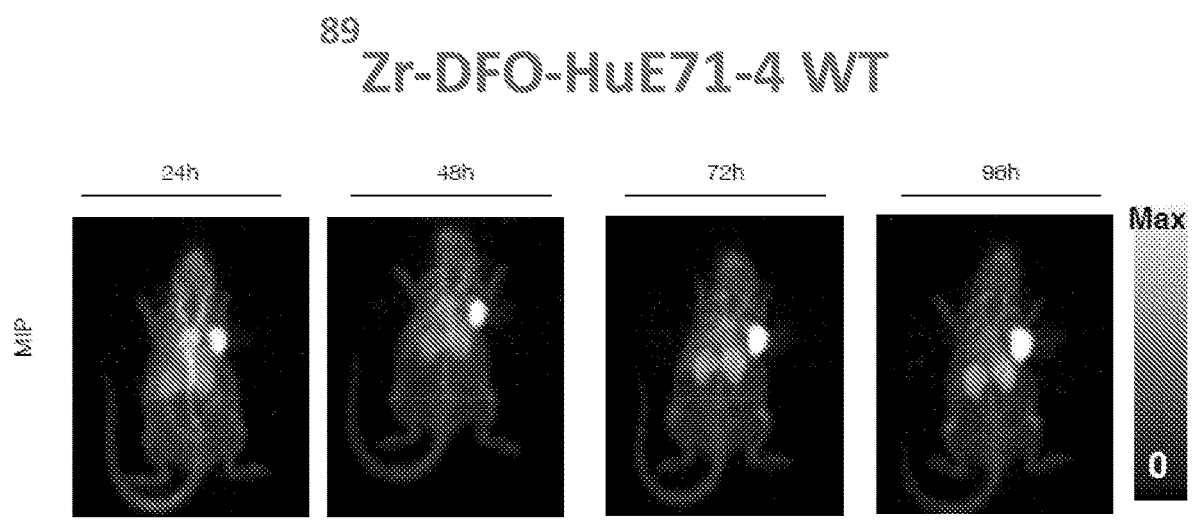
FIG. 51 shows the serial PET imaging of $^{89}$Zr-HuE71-4 WT antibody. Small-animal PET imaging in a subcutaneous ovarian cancer tumor model revealed high tumor and kidney activity concentration. Representative maximal intensity projection (MIP) PET images of $^{89}$Zr-HuE71-4 WT (198-204 µCi in 150 µL of PBS injected via tail vein) in athymic nude mice bearing subcutaneous L1-CAM-positive SKOV-3 tumors xenografted on the right shoulder.

For $^{89}$Zr-HuE71-4 WT (FIG. 51), the majority of the activity was within the tumor tissue at 24 hours and in the maximal intensity projections, blood pool activity could be visualized quite clearly. Two bilateral structures in the middle of the animal (gray arrow) could also be seen and these have been confirmed to be kidneys. The high activity within the tumor tissue persisted up to 96 hours post-injection, as well as the kidney activity.

Figure 52:
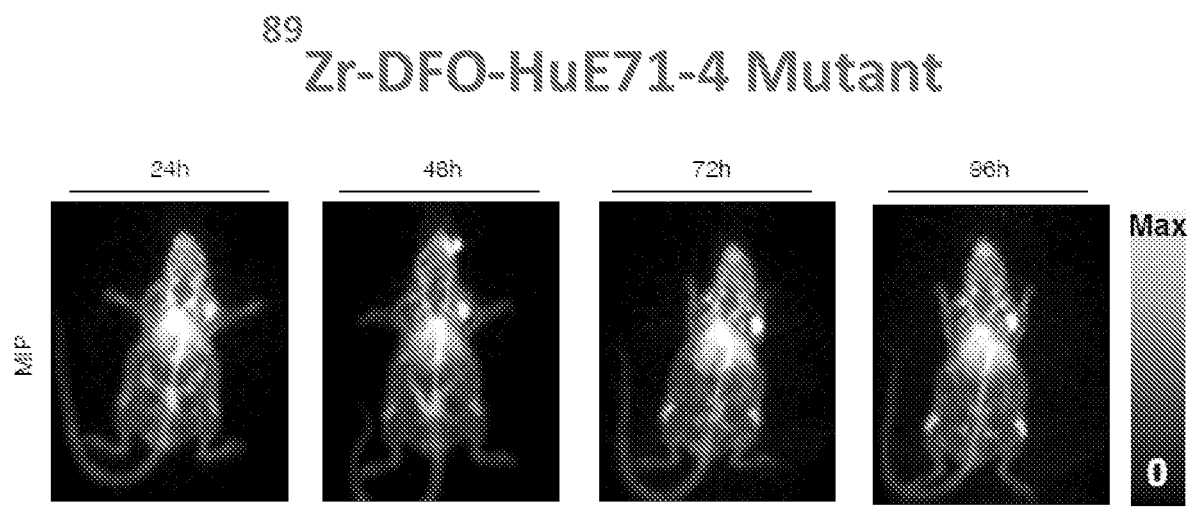
FIG. 52 shows the serial PET imaging of $^{89}$Zr-HuE71-4 Mutant antibody. Small-animal PET imaging in a subcutaneous ovarian cancer tumor model revealed high tumor and background tissue activity while kidney activity appeared minimal. Representative maximal intensity projection (MIP) PET images of $^{89}$Zr-HuE71-4 Mutant (206-212 µCi in 150 µL of PBS injected via tail vein) in athymic nude mice bearing subcutaneous L1-CAM-positive SKOV-3 tumors xenografted on the right shoulder.

In images of $^{89}$Zr-HuE71-4 Mutant (FIG. 52), a slight tumor uptake at 24 hours was observed that continued to gradually accumulate over a period of time up to 96 hours. Here, there was blood pool activity that, in this case, appeared to partially decrease throughout 96 hours. Most notable, however, is the absence of kidney uptake with $^{89}$Zr-HuE71-4 Mutant that was clearly observed with $^{89}$Zr-HuE71-4 WT.

Figure 53:
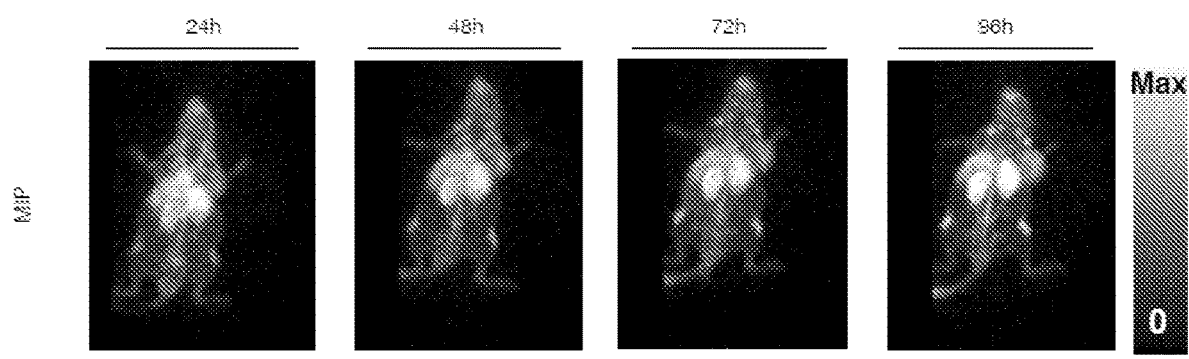
FIG. 53 shows the serial PET imaging of $^{89}$Zr-HuCtrl-4 WT antibody. Small-animal PET imaging in a subcutaneous ovarian cancer tumor model revealed low tumor but high kidney activity. Representative maximal intensity projection (MIP) PET images of $^{89}$Zr-HuCtrl-4 WT (200-211 µCi in 150 µL of PBS injected via tail vein) in athymic nude mice bearing subcutaneous L1-CAM-positive SKOV-3 tumors xenografted on the right shoulder.

The final tracer imaged in this study was a non-specific control antibody, $^{89}$Zr-HuCtrl-4 WT (FIG. 53). At all time points the activity within the tumor tissue was very minimal, consistent with the fact that the target of the antibody, GD2, was not highly expressed by the SKOV-3 cell line. Liver activity could be seen through all of the time points as well as intense kidney activity.

Besides the control antibody ($^{89}$Zr-HuCtrl-4 WT), all of the other tracers had the exact same antigen binding site targeting L1-CAM. The only differences between the five L1-CAM tracers are within the Fc region, which had a significant impact on in vivo biodistribution. According to the PET images, the antibody variants that had lower Fc receptor binding ($^{89}$Zr-HuE71-1 Aglyco, $^{89}$Zr-HuE71-4 WT, $^{89}$Zr-HuE71-4 Mutant) did not exhibit lymph node uptake. Conversely, the antibodies that have normal or enhanced Fc gamma receptor binding ($^{89}$Zr-HuE71-1 WT, $^{89}$Zr-HuE71-1 MAGE) have intense lymph node uptake. Taken together, the data suggests that local expression of the antigen does not play a role in lymph node uptake because the antigen binding regions of all of the L1-CAM tracers were the same. Further, L1-CAM radioimmunoconjugates yielded greater than 85% immunoreactive fractions in the immunoreactivity assays, which excludes differences in antigen binding as a cause for the differential lymph node uptake. Because the normal and enhanced Fc gamma receptor binding antibodies ($^{89}$Zr-HuE71-1 MAGE and $^{89}$Zr-HuE71-1 WT) exhibited statistically significantly higher lymph node uptake as compared to the low Fc gamma receptor binding antibodies ($^{89}$Zr-HuE71-1 Aglyco, $^{89}$Zr-HuE71-4 WT, $^{89}$Zr-HuE71-4 Mutant), the high lymph node uptake observed is likely due to differences in Fc binding.

With respect to the IgG4 tracers, high kidney uptake was observed in the wild-type variant. A S228P mutation in this tracer was able to reduce the kidney uptake to the point where it could not be visualized on PET at any time point. IgG4 antibodies, as described earlier, undergo dynamic Fab arm exchange and are capable of spontaneously breaking apart at the hinge region (to form a ~75 kDa construct) and then recombine with other half molecules. Without wishing to be bound by theory, it is believed that the kidney uptake observed in the wild type IgG4 L1-CAM antibody may be a secondary effect of the dynamic Fab arm exchange property because the S228P mutation prevents this renal accumulation from occurring. Also, the 75 kDa half antibody may be undergoing further reduction into 25 and 50 kDa fragments allowing them to pass through the glomeruli within the kidneys. The non-specific $^{89}$Zr-HuCtrl-4 WT IgG4 antibody exhibits high accumulation within the renal tissue, which is consistent with the IgG4-renal uptake theory.

Ex Vivo Biodistribution.

Figure 54:
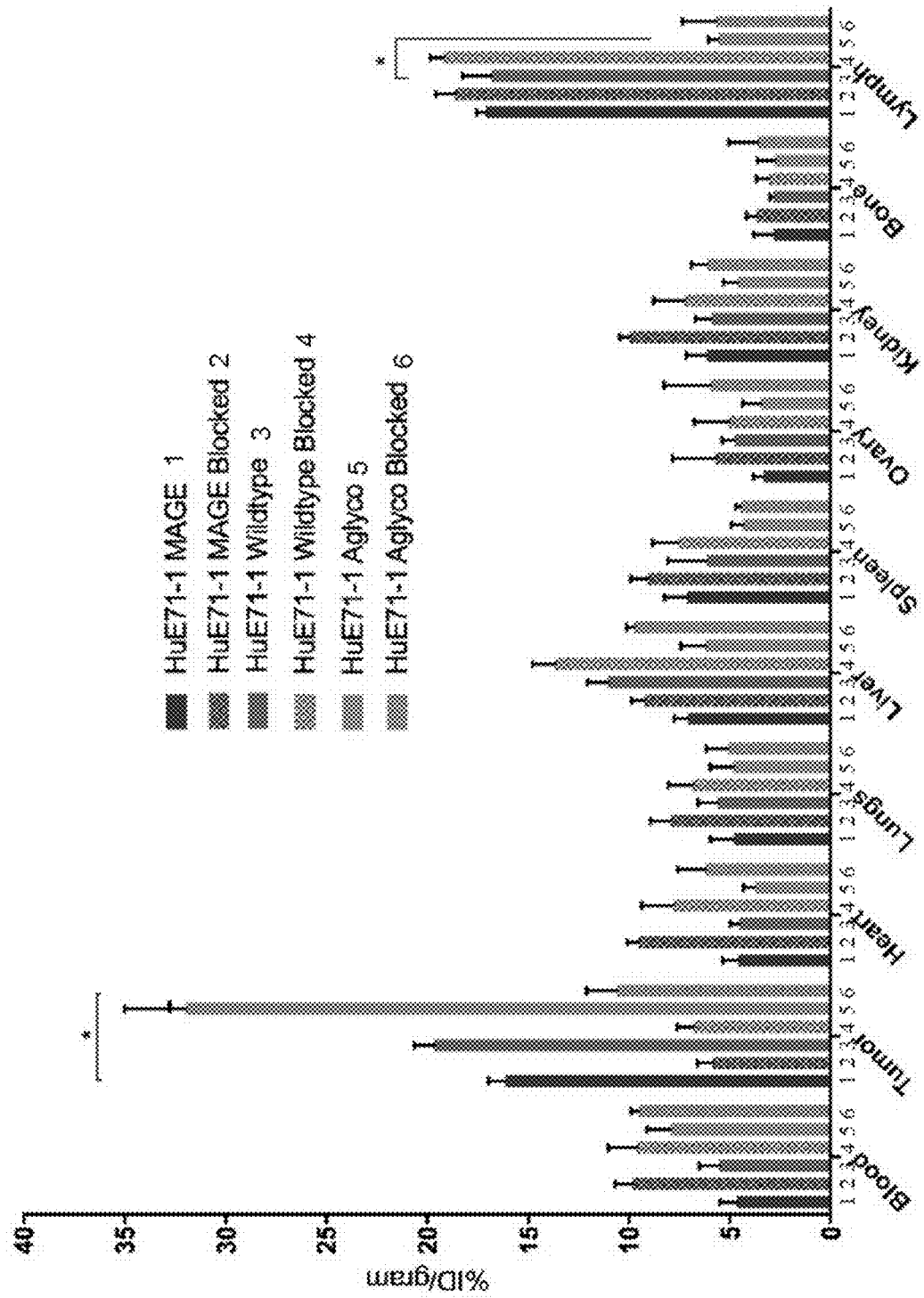
FIG. 54 shows the ex vivo biodistribution of IgG1 antibodies 96 hours post-injection of tracer. Acute biodistribution of radioimmunoconjugates in SKOV-3 tumor-bearing mice. Biodistribution data from athymic nude mice (n=4 per group) following the administration of IgG1 radioimmunoconjugates via tail vein injection (17-24 µCi, 3-6 µg). A 50-fold excess was co-injected for the blocking groups. % ID/g values listed in FIG. 55. Asterisk indicates P<0.05.

To confirm the PET imaging results and to verify specificity of the tracers, ex vivo biodistribution studies were performed (FIG. 54 and FIG. 55). The radiolabeled immunoconjugates were injected via tail vein into female athymic nude mice bearing SKOV3 tumors and various tissues were collected at 96 hours post-injection, analyzed on a gamma counted, and weight normalized. The results of these studies matched the trends that were revealed by the PET imaging experiments. The antibodies known to have normal or enhanced Fc gamma receptor binding ($^{89}$Zr-HuE71-1 WT, $^{89}$Zr-HuE71-1 MAGE) displayed high lymph node uptake (16.85±1.39% ID/gram, 17.16±0.41% ID/gram). Conversely, the aglycosylated variant of the antibody, $^{89}$Zr-HuE71-1 Aglyco, demonstrated a basal level of lymph node uptake of 5.59±0.49% ID/gram. The values obtained via ex vivo biodistribution correlate with the PET imaging data and further corroborate the hypothesis that increased lymph node uptake is due to binding of the Fc region of the antibody as opposed to the variable region.

Figure 56:
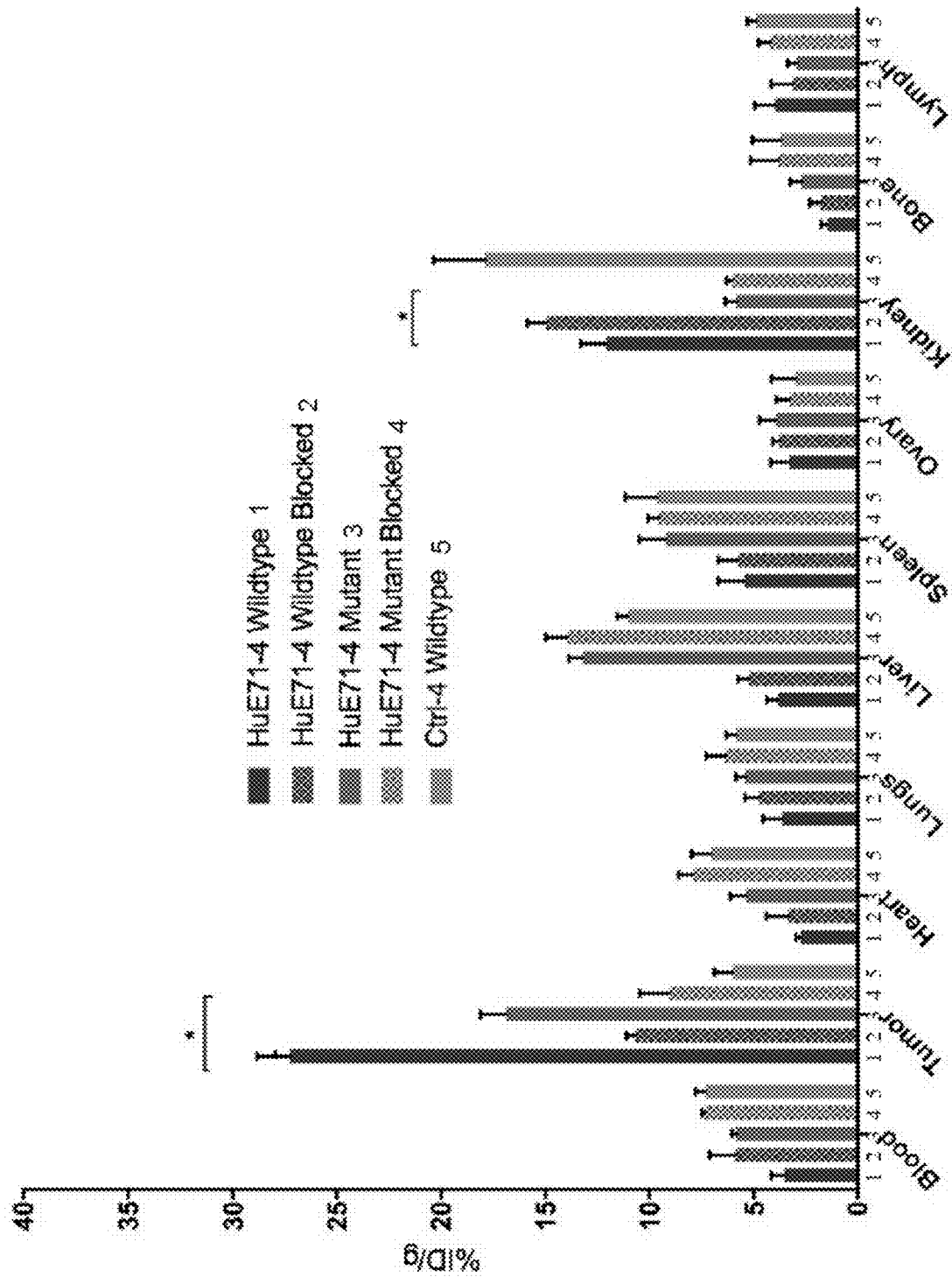
FIG. 56 shows the ex vivo biodistribution of IgG4 antibodies 96 hours post-injection of tracer. Acute biodistribution of radioimmunoconjugates in SKOV-3 tumor-bearing mice. Biodistribution data from athymic nude mice (n=4 per group) following the administration of IgG4 radioimmunoconjugates via tail vein injection (21-26 µCi, 3-6 µg). A 50-fold excess was co-injected for the blocking groups. % ID/g values listed in FIG. 57. Asterisk indicates P<0.05.

For the IgG4 antibodies, $^{89}$Zr-HuE71-4 WT displayed lymph node uptake of 3.98±0.969% ID/gram while $^{89}$Zr-HuE71-4 Mutant was 3.70±0.975% ID/gram (FIG. 56 and FIG. 57). No significant difference was seen with these two antibodies within the lymph nodes. $^{89}$Zr-HuE71-4 WT accumulated in the kidneys with a value of 12.06±1.23% ID/gram while $^{89}$Zr-HuE71-4 Mutant was significantly lower at 5.83±0.537% ID/gram. These data recapitulate what was observed in the PET imaging data and further suggest that the IgG4 property of dynamic Fab arm exchange plays a role in the renal uptake of the tracers.

To evaluate the specificity of these tracers for the target, blocking groups were included in the ex vivo biodistribution studies. Fifty-fold excess of the cold tracer was co-injected with the radiolabeled tracer via the tail vein. In theory, the addition of the cold tracer would dramatically reduce the specific activity of the hot tracer and a significant decrease in uptake of the hot tracer would be observed. This was observed for all five of the L1-CAM targeted antibodies. Tumor tissue uptake values were reduced from 16.15±0.85% ID/gram to 5.87±0.76% ID/gram for $^{89}$Zr-HuE71-1 MAGE, 19.67±1.23% ID/gram to 6.82±0.809% ID/gram for $^{89}$Zr-HuE71-1 WT, 32.02±2.99% ID/gram to 10.58±1.52% ID/gram for $^{89}$Zr-HuE71-1 Aglyco, 27.29±1.55% ID/gram to 10.65±0.472% ID/gram for $^{89}$Zr-HuE71-4 WT, and 16.90±1.21% ID/gram to 9.04±1.42% ID/gram for $^{89}$Zr-HuE71-4 Mutant. For $^{89}$Zr-HuCtrl-4 WT, a non-specific antibody in this model, the tumor uptake was quite low at 6.02±0.90% ID/gram. This uptake in the tumor tissue can be attributed to the enhanced permeability and retention (EPR) effect. See Heneweer C et al., *J Nucl Med* 52:625-33 (2011).

Ex Vivo Histology.

Figure 58:
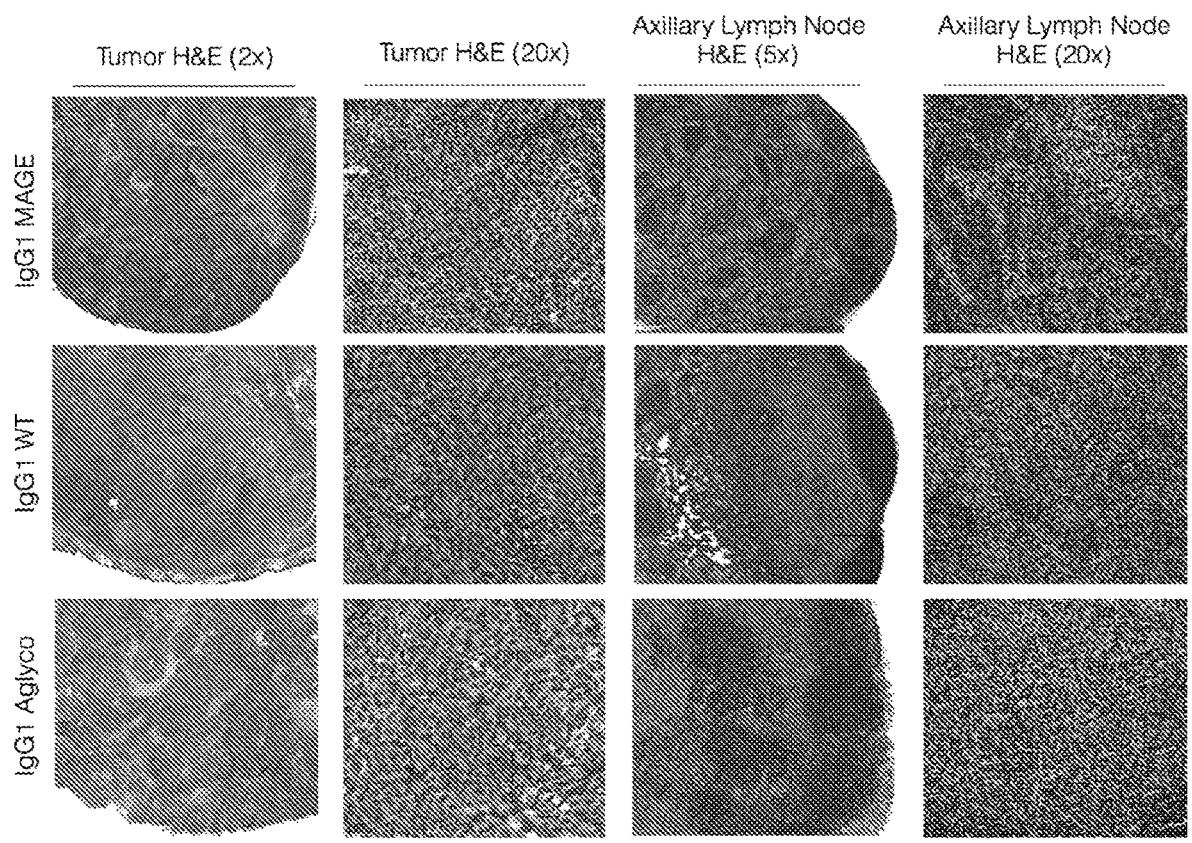
FIG. 58 shows the ex vivo histological analysis of tumor and lymph node tissue. Tumor and lymph node tissue of mice injected with specified radioimmunoconjugate were collected, embedded in paraffin and subjected to routine H&E staining and analysis.

Lymph nodes and tumors were collected and analyzed histologically to determine whether the lymph node uptake that was observed in PET imaging studies with the IgG1 tracers actually indicated metastatic disease (FIG. 58). Hematoxylin and eosin staining of the tumor tissue confirmed the mass to be anaplastic carcinoma. The tumor tissue was described as well demarcated, unencapsulated, densely cellular nodular neoplastic mass which consists of tightly packed lobules and nests of neoplastic epithelial cells supported by fine fibrovascular septa. Neoplastic cells were polygonal to spindloid, had variably distinct cell borders, abundant amounts of eosinophilic cytoplasm occasionally vacuolated, and round nuclei with finely granular to vesicular chromatin and 1-2 evident magenta nucleoli. There was severe anisocytosis and anisokaryosis. Mitoses average 4-6 per single high power field (40×). There were multifocal areas of coagulative necrosis. Hematoxylin and eosin staining of the right and left axillary lymph nodes and mesenteric lymph nodes revealed histiocytosis and plasmacytosis, a common manifestation of drainage reaction, within the medullary sinuses and no evidence of neoplastic cells.

$^{177}$Lu Radioimmunotherapy Study.

Figure 59A:
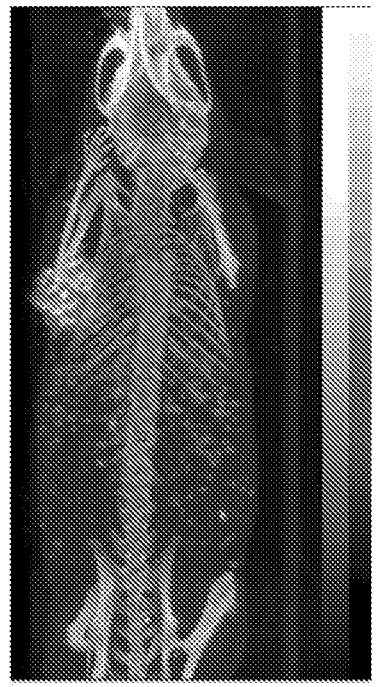
FIGS. 59(A)-59(C) show the results for $^{177}$Lu-HuE71-1 Aglyco imaging and ex vivo biodistribution.
Figure 59B:
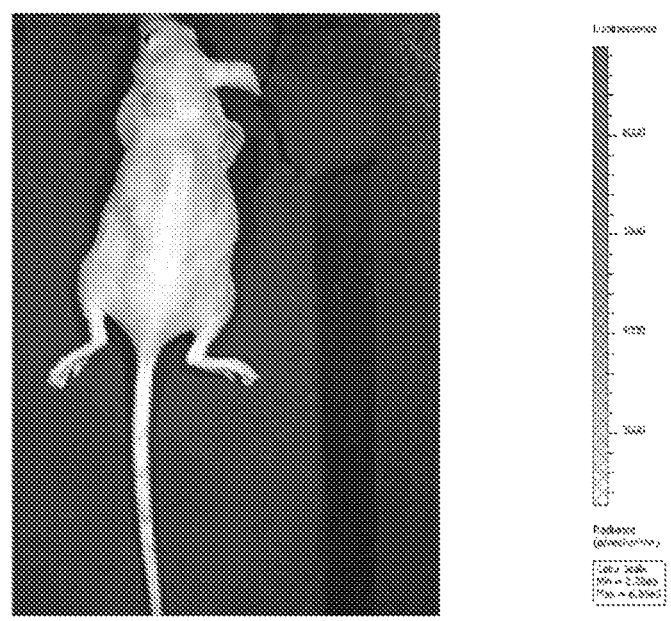
Figure 59C:
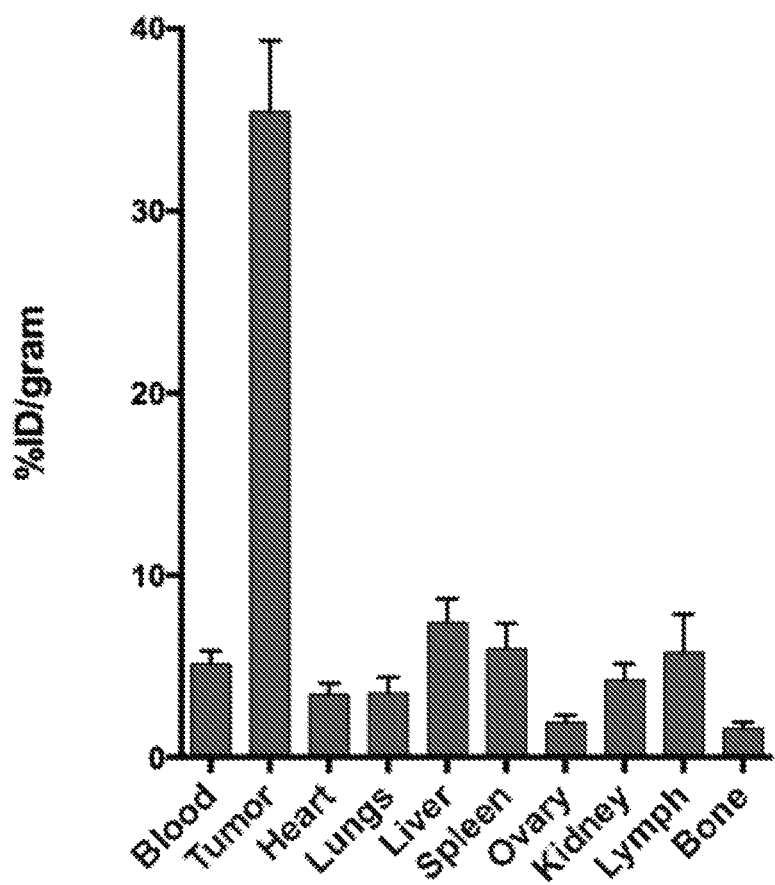

As demonstrated above, $^{89}$Zr-HuE71-1 Aglyco exhibited high tumor activity concentration of 32.02±2.99% ID/gram at 96 hours post-injection along with low background tissue uptake (especially kidneys and blood). $^{89}$Zr-HuE71-1 Aglyco was labeled with the metallic radionuclide $^{177}$Lu because of its radiochemical properties (half-life, 6.7 days; mean range, 0.2 mm; %ß=100) and the widespread use of $^{177}$Lu in imaging and radioimmunotherapy applications. The HuE71-1 Aglyco antibody was conjugated to DOTA, labeled with $^{177}$Lu specific activity of 3.94 mCi/mg (radiochemical purity>99%) and subjected to imaging studies and an ex vivo biodistribution study in athymic nude female mice bearing SKOV-3 subcutaneous tumors (FIGS. 59(A)-59(C)). These studies confirmed a similar biodistribution profile as observed with the $^{89}$Zr-HuE71-1 Aglyco with the majority of the activity localizing to the tumor tissue as seen in the SPECT/CT image and Cerenkov image, and confirmed by ex vivo biodistribution 168 hours post-injection.

Figure 60:
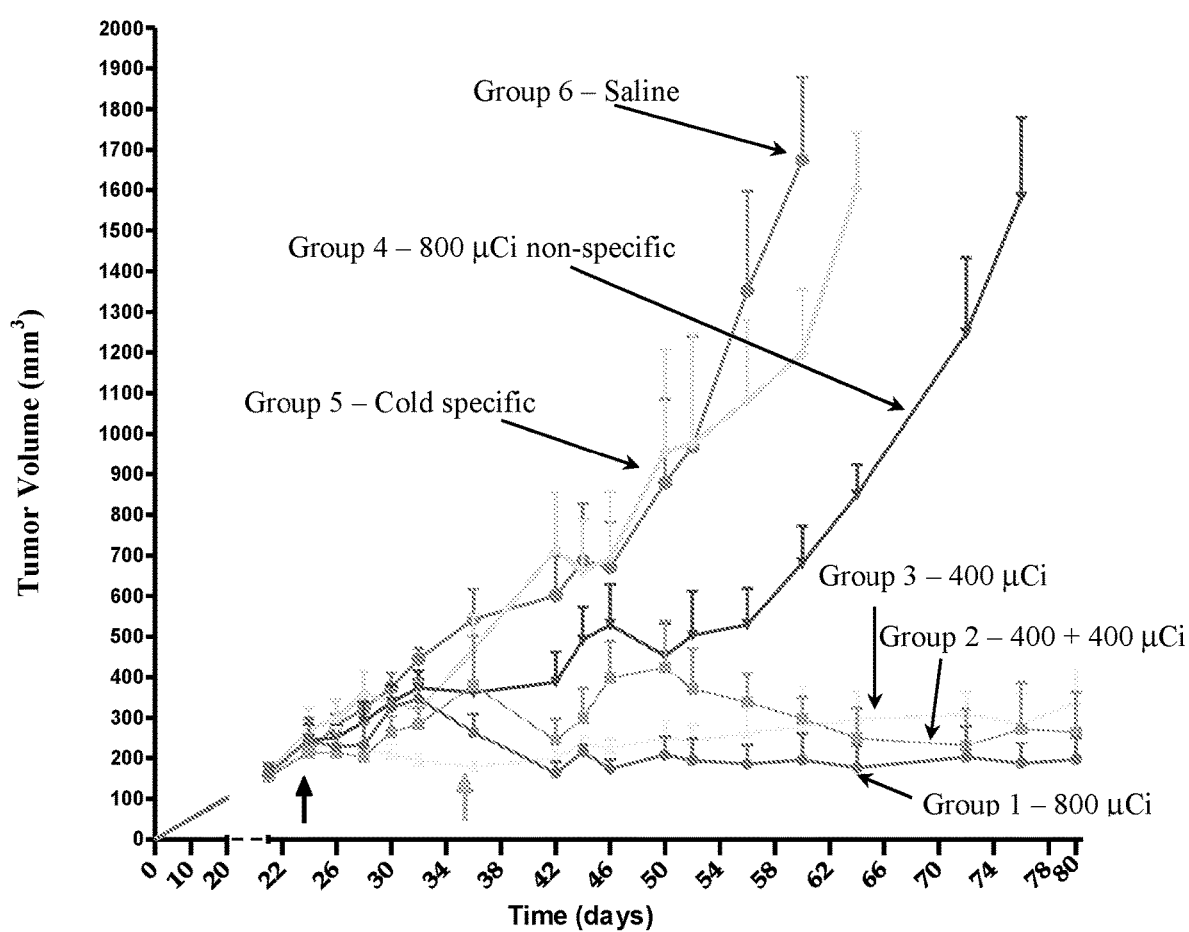
FIG. 60 shows the average tumor volumes in animals subjected to $^{177}$Lu-HuE71-1 Aglyco radioimmunotherapy. Plot of the average tumor volume for each cohort of mice during the first 80 days of the PRIT study are shown with error bars denoting standard deviation. Black arrow indicates first injection of the specified treatment and gray arrow indicates second dose of $^{177}$Lu-HuE71-1 Aglyco in the fractionated dose group. Tumor volumes were acquired using hand-held TM900 scanner (Peira, Brussels, BE). After initial tumor measurements, mice were randomized into groups (n=8-9 per group), ensuring all cohorts had approximately equal average tumor volumes to start.

The efficacy of $^{177}$Lu-HuE71-1 Aglyco as a radioimmunotherapeutic agent was evaluated at 3 doses (800 µCi, 800 µCi fractionated [2 doses, staggered 14 days], and 400 Ci) and compared with the cold antibody, 800 µCi non-specific antibody control, and saline in the same animal model (n=8-9 per group) (FIG. 60). Following the average tumor volume through 80 days (60 days post initial treatment), significant differential responses were observed between the control groups and the radiolabeled treatment groups. Notably, none of the control groups displayed signs of tumor regression beyond the starting volume. The three $^{177}$Lu-HuE71-1 Aglyco groups showed significant growth-delay effects through 80 days post-inoculation. However, there was no significant difference within the $^{177}$Lu-HuE71-1 Aglyco groups in terms of tumor volume during the later time points of the study with the average tumor volumes for these groups being equivalent within error on Day 80. In addition, signs of toxicity (weight loss>80% and petechiae) were observed in 4/8 of the mice in the highest treatment group (800 µCi, $^{177}$Lu-HuE71-1 Aglyco) within the first 2 weeks following treatment. Toxicity was not observed in any of the mice injected with 800 Ci of the non-specific control antibody, which is most likely due to the difference in clearance/elimination of the tracers. These data suggest that a single dose of 400 µCi $^{177}$Lu-HuE71-1 Aglyco is sufficient to delay tumor growth in this model while avoiding toxicity issues.

Taken together, these results demonstrate that the antibodies or antigen binding fragments of the present technology can detect tumors and inhibit the progression of tumor growth and/or metastasis. Accordingly, the immunoglobulin-related compositions disclosed herein are useful for detecting and treating a L1-CAM-positive cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An anti-L1-CAM antibody or antigen binding fragment thereof comprising a heavy chain immunoglobulin variable domain ($V_H$) and a light chain immunoglobulin variable domain ($V_L$), wherein:
   (a) the $V_H$ comprises a $V_H$-CDR1 sequence of GYTFT-SYWMQ (SEQ ID NO: 53), a $V_H$-CDR2 sequence of EINPSNGRTNYNEMFKS (SEQ ID NO: 54), and a $V_H$-CDR3 sequence of YDGYYAMDY (SEQ ID NO: 55); and
   (b) the $V_L$ comprises a $V_L$-CDR1 sequence of KSSQSL-LYSSNQKNYLA (SEQ ID NO: 56), a $V_L$-CDR2 sequence of WASTRES (SEQ ID NO: 57), and a $V_L$-CDR3 sequence of QQYHSYPFT (SEQ ID NO: 58),
   optionally wherein the antibody or antigen binding fragment is conjugated to an agent selected from the group consisting of an isotope, a dye, a chromagen, a contrast agent, a drug, a toxin, a cytokine, an enzyme, an enzyme inhibitor, a hormone, a hormone antagonist, a growth factor, a radionuclide, a metal, a liposome, a nanoparticle, RNA, DNA and any combination thereof.

2. The antibody or antigen binding fragment of claim 1, further comprising a Fc domain of an isotype selected from the group consisting of IgG1, IgG2, IgG3, IgG4, IgA1, IgA2, IgM, IgD, and IgE.

3. The antibody of claim 2, comprising
   an IgG1 constant region comprising one or two amino acid substitutions selected from the group consisting of N297A and K322A; or
   an IgG4 constant region comprising a S228P mutation.

4. The antigen binding fragment of claim 1, wherein the antigen binding fragment is selected from the group consisting of Fab, F(ab')₂, Fab', scFv, and Fv.

5. The antibody of claim 1, wherein the antibody is a monoclonal antibody, chimeric antibody, bispecific antibody, or humanized antibody.

6. The antibody of claim 5, wherein the bispecific antibody binds to T cells, B-cells, myeloid cells, plasma cells, or mast-cells or wherein the bispecific antibody binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

7. The antibody of claim 1, further comprising a heavy chain (HC) amino acid sequence of SEQ ID NO: 9, SEQ ID NO: 10, SEQ ID NO: 26, SEQ ID NO: 42, SEQ ID NO: 46, or SEQ ID NO: 49, or a light chain (LC) amino acid sequence of SEQ ID NO: 13, SEQ ID NO: 14, SEQ ID NO: 25, SEQ ID NO: 41, SEQ ID NO: 45, or SEQ ID NO: 50.

8. A composition comprising the antibody or antigen binding fragment of claim 1 and a pharmaceutically-acceptable carrier.

9. An anti-L1-CAM antibody comprising a heavy chain (HC) amino acid sequence and a light chain (LC) amino acid sequence selected from the group consisting of:
   SEQ ID NO: 9 and SEQ ID NO: 13 (huE71 H1/L1);
   SEQ ID NO: 9 and SEQ ID NO: 14 (huE71 H1/L2);
   SEQ ID NO: 10 and SEQ ID NO: 13 (huE71 H2/L1);
   SEQ ID NO: 10 and SEQ ID NO: 14 (huE71 H2/L2);
   SEQ ID NO: 17 and SEQ ID NO: 21 (huE72 H1/L1);
   SEQ ID NO: 17 and SEQ ID NO: 22 (huE72 H1/L2);
   SEQ ID NO: 18 and SEQ ID NO: 21 (huE72 H2/L1);
   SEQ ID NO: 18 and SEQ ID NO: 22 (huE72 H2/L2);
   SEQ ID NO: 26 and SEQ ID NO: 25 (chE71IgG1);
   SEQ ID NO: 30 and SEQ ID NO: 29 (chE72 IgG1);
   SEQ ID NO: 42 and SEQ ID NO: 41 (chE71IgG4);
   SEQ ID NO: 46 and SEQ ID NO: 45 (huE71IgG4);
   SEQ ID NO: 49 and SEQ ID NO: 50 (huE71 BsAb); and
   SEQ ID NO: 51 and SEQ ID NO: 52 (huE72 BsAb),
   optionally wherein the antibody is conjugated to an agent selected from the group consisting of an isotope, a dye, a chromagen, a contrast agent, a drug, a toxin, a cytokine, an enzyme, an enzyme inhibitor, a hormone, a hormone antagonist, a growth factor, a radionuclide, a metal, a liposome, a nanoparticle, RNA, DNA and any combination thereof.

10. The antibody of claim 9, wherein the antibody is a chimeric antibody, bispecific antibody, or a humanized antibody.

11. The antibody of claim 10, wherein the bispecific antibody binds to T cells, B-cells, myeloid cells, plasma cells, or mast-cells or wherein the bispecific antibody binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

12. A composition comprising the antibody of claim 9 and a pharmaceutically-acceptable carrier.

13. An anti-L1-CAM antibody or antigen binding fragment thereof comprising the heavy chain immunoglobulin variable domain ($V_H$) amino acid sequence and the light chain immunoglobulin variable domain ($V_L$) amino acid sequence that are present in
   SEQ ID NO: 9 and SEQ ID NO: 13 (huE71 H1/L1);
   SEQ ID NO: 9 and SEQ ID NO: 14 (huE71 H1/L2);
   SEQ ID NO: 10 and SEQ ID NO: 13 (huE71 H2/L1);
   SEQ ID NO: 10 and SEQ ID NO: 14 (huE71 H2/L2);
   SEQ ID NO: 17 and SEQ ID NO: 21 (huE72 H1/L1);
   SEQ ID NO: 17 and SEQ ID NO: 22 (huE72 H1/L2);
   SEQ ID NO: 18 and SEQ ID NO: 21 (huE72 H2/L1); or
   SEQ ID NO: 18 and SEQ ID NO: 22 (huE72 H2/L2),
   respectively.

14. A method for treating a L1-CAM associated cancer or tumor in a subject in need thereof, comprising administering to the subject an effective amount of the antibody of claim 9, wherein the antibody specifically binds to and neutralizes L1-CAM activity.

15. The method of claim 14, wherein the L1-CAM associated cancer or tumor is leukemia, Ewing's sarcoma, neuroblastoma, osteosarcoma, glioblastoma multiforme, ovarian cancer, endometrial cancer, uterine cancer, triple negative breast cancer, melanoma, clear cell renal cell cancer, pheochromacytoma and paraganglioma, mesothelioma, small cell lung cancer (SCLC), non-small cell lung cancer (NSCLC), pancreatic ductal cancer, colon cancer, pancreatic cancer, hepatocellular carcinoma, gastric cancer, cholangiocarcinoma, carcinoid, neuroendocrine tumors, gastrointestinal stromal tumor (GIST), pheochromocytoma, glioma, pancreatic neuroectodermal cancer, pancreatic adenocarcinoma, colorectal cancer, renal cell carcinoma, chondrosarcoma, esophageal adenocarcinoma, oligodendroglioma, astrocytoma, ependymoma, pancreatic neuroendocrine carcinoma, adrenal adenoma, leiomyosarcoma, liposarcoma, granular cell tumor of the ovary, schwannoma, primitive neuroectodermal tumor (PNET), epitheliod sarcoma, esthesioneuroblastoma, medulloblastoma, capillary hemangioma, Kaposi sarcoma, rhabdomyosarcoma, submaxillary salivary gland cancer, or head and neck squamous cell carcinoma.

16. The method of 14, wherein the antibody is administered to the subject separately, sequentially or simultaneously with an additional therapeutic agent.

17. The method of claim 16, wherein the additional therapeutic agent is one or more of alkylating agents, platinum agents, taxanes, *vinca* agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents.

18. A method for detecting a tumor in a subject in vivo comprising
   (a) administering to the subject an effective amount of the antibody of claim 1, wherein the antibody is configured to localize to a tumor expressing L1-CAM and is labeled with a radioisotope; and
   (b) detecting the presence of a tumor in the subject by detecting radioactive levels emitted by the antibody that are higher than a reference value, optionally wherein the radioactive levels emitted by the antibody are detected using positron emission tomography or single photon emission computed tomography.

19. A method for detecting a tumor in a subject in vivo comprising
   (a) administering to the subject an effective amount of the antibody of claim 9, wherein the antibody is configured to localize to a tumor expressing L1-CAM and is labeled with a radioisotope; and
   (b) detecting the presence of a tumor in the subject by detecting radioactive levels emitted by the antibody that are higher than a reference value, optionally wherein the radioactive levels emitted by the antibody are detected using positron emission tomography or single photon emission computed tomography.

* * * * *

SEQUENCE LISTING

```
<160> NUMBER OF SEQ ID NOS: 79

<210> SEQ ID NO 1
<211> LENGTH: 118
<212> TYPE: PRT
<213> ORGANISM: Mus sp.

<400> SEQUENCE: 1

Gln Val Gln Leu Gln Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Met Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Leu Tyr Asp Gly Tyr Tyr Ala Met Asp Tyr Trp Gly Gln Gly Thr
                100                 105                 110

Ser Val Thr Val Ser Ser
            115

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80
```

```
Leu Gln Ile Cys Ser Leu Lys Ala Glu Asp Thr Ala Val Tyr Tyr Cys
                85                  90                  95

Ala Arg

<210> SEQ ID NO 3
<211> LENGTH: 114
<212> TYPE: PRT
<213> ORGANISM: Mus sp.

<400> SEQUENCE: 3

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Leu Tyr Tyr Cys Gln Gln
                85                  90                  95

Tyr His Ser Tyr Pro Phe Thr Phe Gly Ser Gly Thr Lys Leu Glu Ile
                100                 105                 110

Lys Arg

<210> SEQ ID NO 4
<211> LENGTH: 113
<212> TYPE: PRT
<213> ORGANISM: Homo sapiens

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Tyr Thr Phe Gly Gln Gly Thr Lys Leu Glu
                100                 105                 110

Ile

<210> SEQ ID NO 5
<211> LENGTH: 120
<212> TYPE: PRT
<213> ORGANISM: Mus sp.

<400> SEQUENCE: 5

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Gly Tyr
```

```
                    20                  25                  30
Trp Met His Trp Val Lys Gln Arg Pro Gly His Gly Leu Glu Trp Ile
            35                  40                  45
Gly Glu Ile Asn Pro Ser Asn Gly Arg Thr Asn Tyr Asn Glu Arg Phe
        50                  55                  60
Lys Ser Lys Ala Thr Leu Thr Val Asp Lys Ser Ser Thr Thr Ala Phe
65                  70                  75                  80
Met Gln Leu Ser Gly Leu Thr Ser Glu Asp Ser Ala Val Tyr Phe Cys
                85                  90                  95
Ala Arg Asp Tyr Tyr Gly Thr Ser Tyr Asn Phe Asp Tyr Trp Gly Gln
            100                 105                 110
Gly Thr Thr Leu Thr Val Ser Ser
            115                 120

<210> SEQ ID NO 6
<211> LENGTH: 113
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Tyr Phe Asp Tyr Trp Gly Gln Gly Thr Leu Val Thr Val Ser
            100                 105                 110
Ser

<210> SEQ ID NO 7
<211> LENGTH: 108
<212> TYPE: PRT
<213> ORGANISM: Mus sp.

<400> SEQUENCE: 7

Asp Ile Gln Met Thr Gln Ser Ser Ser Phe Ser Val Ser Leu Gly
1               5                   10                  15
Asp Arg Val Thr Ile Thr Cys Lys Ala Asn Glu Asp Ile Asn Asn Arg
            20                  25                  30
Leu Ala Trp Tyr Gln Gln Thr Pro Gly Asn Ser Pro Arg Leu Leu Ile
            35                  40                  45
Ser Gly Ala Thr Asn Leu Val Thr Gly Val Pro Ser Arg Phe Ser Gly
        50                  55                  60
Ser Gly Ser Gly Lys Asp Tyr Thr Leu Thr Ile Thr Ser Leu Gln Ala
65                  70                  75                  80
Glu Asp Phe Ala Thr Tyr Tyr Cys Gln Gln Tyr Trp Ser Thr Pro Phe
                85                  90                  95
Thr Phe Gly Ser Gly Thr Glu Leu Glu Ile Lys Arg
            100                 105
```

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Cys
                85                  90                  95

Thr Phe Gly Gln Gly Thr Lys Leu Glu Ile Lys Arg
            100                 105

<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Met Phe
    50                  55                  60

Lys Ser Lys Ala Val Leu Ser Val Asp Lys Ser Val Ser Thr Ala Tyr
65                  70                  75                  80

Met Gln Leu Ser Ser Leu Thr Ala Glu Asp Thr Ala Val Tyr Tyr Cys
                85                  90                  95

Ala Leu Tyr Asp Gly Tyr Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

```
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 10
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ser Glu Leu Lys Lys Pro Gly Ala
1               5                   10                  15
Ser Val Lys Leu Ser Cys Lys Ala Ser Gly Tyr Thr Phe Thr Ser Tyr
            20                  25                  30
Trp Met Gln Trp Val Arg Gln Ala Pro Gly Gln Gly Leu Glu Trp Ile
        35                  40                  45
Gly Glu Ile Asn Pro Ser Asn Gly Arg Thr Asn Tyr Asn Glu Met Phe
    50                  55                  60
Lys Ser Arg Ala Val Leu Ser Val Asp Thr Ser Val Ser Thr Ala Tyr
65                  70                  75                  80
Met Gln Leu Cys Ser Leu Lys Ala Glu Asp Thr Ala Val Tyr Tyr Cys
                85                  90                  95
Ala Leu Tyr Asp Gly Tyr Tyr Ala Met Asp Tyr Trp Gly Gln Gly Thr
            100                 105                 110
Leu Val Thr Val Ser Ser Ala Ser Thr Lys Gly Pro Ser Val Phe Pro
```

```
                 115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445

<210> SEQ ID NO 11
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtgcagc tggtgcagcc cggcgacgag ctggtgaagc ccggcgcctc cgtgaagctg      60
tcctgcaagg cctccggcta caccttcacc tcctactgga tgcagtgggt gaagcagcgg     120
cccggccagg gcctggagtg gatcggcgag atcaacccct ccaacggccg gaccaactac     180
```

```
aacgagatgt tcaagtccaa ggccgtgctg tccgtggaca agtccgtgtc caccgcctac    240
atgcagctgt cctccctgac cgccgaggac accgccgtgt actactgcgc cctgtacgac    300
ggctactacg ccatggacta ctggggccag ggcaccctgg tgaccgtgtc ctccgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccccggcg tcctacagtc ctcaggactc    540
tactccctca gcagcgtggt gaccgtgccc tccagcagct gggcaccca gacctacatc     600 tgcaacgtga atcacaagcc cagcaacacc aaggtggaca agagagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga                                       1347

<210> SEQ ID NO 12
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggtgcagc tggtgcagtc cggctccgag ctgaagaagc ccggcgcctc cgtgaagctg     60
tcctgcaagg cctccggcta caccttcacc tcctactgga tgcagtgggt gcggcaggcc    120
cccggccagg gcctggagtg gatcggcgag atcaaccccct ccaacggccg gaccaactac    180
aacgagatgt tcaagtcccg ggccgtgctg tccgtggaca cctccgtgtc caccgcctac    240
atgcagctgt gctccctgaa ggccgaggac accgccgtgt actactgcgc cctgtacgac    300
ggctactacg ccatggacta ctggggccag ggcaccctgg tgaccgtgtc ctccgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccccggcg tcctacagtc ctcaggactc    540
tactccctca gcagcgtggt gaccgtgccc tccagcagct gggcaccca gacctacatc     600 tgcaacgtga atcacaagcc cagcaacacc aaggtggaca agagagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
```

```
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatga                                        1347
```

<210> SEQ ID NO 13
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Asp Ile Val Met Thr Gln Ser Pro Ser Ser Leu Ala Val Ser Val Gly
1               5                   10                  15

Glu Arg Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Val Ala Leu Tyr Tyr Cys Gln Gln
                85                  90                  95

Tyr His Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 14
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr His Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 15
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gacatcgtga tgacccagtc cccctcctcc ctggccgtgt ccgtgggcga gcgggtgacc      60
atgtcctgca agtcctccca gtccctgctg tactcctcca accagaagaa ctacctggcc     120
tggtaccagc agaagcccgg ccagtccccc aagctgctga tctactgggc ctccacccgg     180
gagtccggcg tgcccgaccg gttctccggc tccggctccg gcaccgactt caccctgacc     240
atctcctccg tgaaggccga ggacgtggcc ctgtactact gccagcagta ccactcctac     300
cccttcacct tcggccaggg caccaagctg gagatcaagc ggaccgtggc cgcccccctcc    360 gtgttcatct tccccccctc cgacgagcag ctgaagtccg gcaccgcctc cgtggtgtgc     420
ctgctgaaca acttctaccc ccgggaggcc aaggtgcagt ggaaggtgga caacgccctg     480
cagtccggca actcccagga gtccgtgacc gagcaggact ccaaggactc cacctactcc     540
ctgtcctcca ccctgaccct gtccaaggcc gactacgaga agcacaaggt gtacgcctgc     600
gaggtgaccc accagggcct gtcctccccc gtgaccaagt ccttcaaccg gggcgagtgc     660
tag                                                                   663

<210> SEQ ID NO 16
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gacatcgtga tgacccagtc ccccgactcc ctggccgtgt ccctgggcga gcgggtgacc      60
atgaactgca gtcctccca gtccctgctg tactcctcca accagaagaa ctacctggcc     120
tggtaccagc agaagcccgg ccagcccccc aagctgctga tctactgggc ctccacccgg     180
gagtccggcg tgcccgaccg gttctccggc tccggctccg gcaccgactt caccctgacc     240
atctcctccc tgcaggccga ggacgtggcc ctgtactact gccagcagta ccactcctac     300
cccttcacct tcggccaggg caccaagctg gagatcaagc ggaccgtggc cgccccctcc     360
gtgttcatct ccccccctc cgacgagcag ctgaagtccg gcaccgcctc cgtggtgtgc     420
ctgctgaaca acttctaccc ccgggaggcc aaggtgcagt ggaaggtgga caacgccctg     480
cagtccggca actcccagga gtccgtgacc gagcaggact ccaaggactc cacctactcc     540
ctgtcctcca ccctgaccct gtccaaggcc gactacgaga agcacaaggt gtacgcctgc     600
gaggtgaccc accagggcct gtcctccccc gtgaccaagt ccttcaaccg gggcgagtgc     660
tag                                                                   663
```

<210> SEQ ID NO 17
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Gly Tyr
            20                  25                  30

Trp Met His Trp Val Lys Gln Ala Pro Gly Gln Gly Leu Glu Trp Ile
        35                  40                  45

Gly Glu Ile Asn Pro Ser Asn Gly Arg Thr Asn Tyr Asn Glu Arg Phe
    50                  55                  60

Lys Ser Lys Ala Thr Leu Thr Val Asp Lys Ser Ile Thr Thr Ala Phe
65                  70                  75                  80

Met Glu Leu Ser Arg Leu Arg Ser Asp Asp Thr Ala Val Tyr Phe Cys
                85                  90                  95

Ala Arg Asp Tyr Tyr Gly Thr Ser Tyr Asn Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Pro Gly Ala Glu Val Lys Lys Pro Gly Ala
1               5                   10                  15

Ser Val Lys Leu Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Glu Ile Asn Pro Ser Asn Gly Arg Thr Asn Tyr Asn Glu Arg Phe
    50                  55                  60

Lys Ser Arg Ala Thr Leu Thr Val Asp Lys Ser Ile Ser Thr Ala Tyr
```

```
            65                  70                  75                  80
Met Glu Leu Ser Arg Leu Arg Ser Asp Asp Thr Ala Val Tyr Phe Cys
                85                  90                  95

Ala Arg Asp Tyr Tyr Gly Thr Ser Tyr Asn Phe Asp Tyr Trp Gly Gln
            100                 105                 110

Gly Thr Leu Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 19
<211> LENGTH: 1350
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 19
caggtgcagc tggtgcagcc tggcgctgaa gtcgtgaagc caggcgcctc cgtgaagctg        60
tcctgcaagg cttccggcta caccttcacc ggctactgga tgcactgggt caagcaggcc       120
cctggacagg gcctggaatg gatcggcgag atcaaccctt ccaacggccg gaccaactac       180
aacgagcggt tcaagtccaa ggccaccctg accgtggaca agtccatcac caccgccttc       240
atggaactgt cccggctgag atccgacgat accgccgtgt acttctgcgc cagagactac       300 tacggcaccct cctacaactt cgactactgg ggccagggca ccctgctgac cgtgtcctct       360
gcttctacca agggcccatc ggtcttcccc ctggcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggccgtcct acagtcctca       540
ggactctact ccctcagcag cgtggtgacc gtgccctcca gcagcttggg cacccagacc       600
tacatctgca acgtgaatca caagcccagc aacaccaagg tggacaagag agttgagccc       660
aaatcttgtg acaaaactca cacatgccca ccgtgcccag cacctgaact cctgggggga       720
ccgtcagtct tcctcttccc cccaaaaccc aaggacaccc tcatgatctc ccggacccct       780
gaggtcacat gcgtggtggt ggacgtgagc cacgaagacc ctgaggtcaa gttcaactgg       840
tacgtggacg gcgtggaggt gcataatgcc aagacaaagc cgcgggagga gcagtacaac       900
agcacgtacc gtgtggtcag cgtcctcacc gtcctgcacc aggactggct gaatggcaag       960
gagtacaagt gcaaggtctc caacaaagcc ctcccagccc ccatcgagaa aaccatctcc      1020
aaagccaaag gcagccccg agaaccacag gtgtacaccc tgcccccatc ccgggatgag      1080
ctgaccaaga accaggtcag cctgacctgc ctggtcaaag gcttctatcc cagcgacatc      1140
gccgtggagt gggagagcaa tgggcagccg gagaacaact acaagaccac gcctcccgtg      1200
ctggactccg acggctcctt cttcctctac agcaagctca ccgtggacaa gagcaggtgg      1260
cagcagggga acgtcttctc atgctccgtg atgcatgagg ctctgcacaa ccactacacg      1320
cagaagagcc tctccctgtc tccgggtaaa                                      1350

<210> SEQ ID NO 20
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggtgcagc tggtgcagcc tggcgctgaa gtgaagaaac ctggcgcctc cgtgaagctg        60
tcctgcaagg cttccggcta caccttcacc ggctactgga tgcactgggt cgacaggct        120 ccaggccagg gactggaatg gatcggcgag atcaaccct ccaacggccg gaccaactac        180
aacgagcggt tcaagtctcg ggccaccctg accgtggaca agtccatctc caccgcctac       240
atggaactgt cccggctgag atccgacgat accgccgtgt acttctgcgc cagagactac       300 tacggcaccct cctacaactt cgactactgg ggccagggca ccctgctgac cgtgtcctct       360
gcttctacca agggcccatc ggtcttcccc ctggcaccct cctccaagag cacctctggg       420
ggcacagcgg ccctgggctg cctggtcaag gactacttcc ccgaaccggt gacggtgtcg       480
```

```
tggaactcag gcgccctgac cagcggcgtg cacaccttcc cggccgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

<210> SEQ ID NO 21
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Ser Ser Ser Phe Ser Val Ser Val Gly
1               5                   10                  15

Asp Arg Val Thr Ile Thr Cys Lys Ala Asn Glu Asp Ile Asn Asn Arg
            20                  25                  30

Leu Ala Trp Tyr Gln Gln Lys Pro Gly Lys Ser Pro Arg Leu Leu Ile
        35                  40                  45

Ser Gly Ala Thr Asn Leu Val Thr Gly Val Pro Ser Arg Phe Ser Gly
    50                  55                  60

Ser Gly Ser Gly Thr Asp Tyr Thr Leu Thr Ile Ser Ser Leu Gln Ala
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

-continued

Phe Asn Arg Gly Glu Cys
    210

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Val Ser Val Gly
1               5                   10                  15

Asp Arg Val Thr Ile Thr Cys Lys Ala Asn Glu Asp Ile Asn Asn Arg
            20                  25                  30

Leu Ala Trp Tyr Gln Gln Lys Pro Gly Lys Ala Pro Lys Leu Leu Ile
        35                  40                  45

Ser Gly Ala Thr Asn Leu Val Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gacatccaga tgacccagtc ctcctccagc ttctccgtgt ccgtgggcga cagagtgacc      60
atcacatgca aggccaacga ggacatcaac aaccggctgg cctggtatca gcagaagccc     120
ggcaagtctc cccggctgct gatctctggc gccaccaatc tcgtgaccgg cgtgccctcc     180
agattctctg gctctggaag cggcaccgac tataccctga ccatcagctc cctgcaggcc     240
gaggacttcg ccacctacta ctgccagcag tactggtcca cccccttcac ctttggccag     300
ggcaccgagc tggaaatcaa gcggacagtg gccgctccct ccgtgttcat cttcccacct     360

```
tccgacgagc agctgaagtc cggcaccgct tctgtcgtgt gcctgctgaa caacttctac    420
ccccgcgagg ccaaggtgca gtggaaggtg acaacgccc  tgcagtccgg caactcccag    480
gaatccgtga ccgagcagga ctccaaggac agcacctact ccctgtcctc cacctgacc     540 ctgtccaagg ccgactacga aagcacaag  gtgtacgcct gcgaagtgac ccaccagggc    600
ctgtctagcc ccgtgaccaa gtctttcaac cggggcgagt gctag                    645
```

<210> SEQ ID NO 24
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
gacatccaga tgacccagtc cccctcctcc ctgtccgtgt ctgtgggcga cagagtgacc    60
atcacatgca aggccaacga ggacatcaac aaccggctgg cctggtatca gcagaagccc    120
ggcaaggccc ccaagctgct gatctctggc gccaccaatc tcgtgaccgg cgtgccctcc    180
agattctccg gctctggctc tggcaccgac tatacctga  ccatctccag cctgcagccc    240
gaggacttcg ccacctacta ctgccagcag tactggtcca ccccttcac  ctttggccag    300 ggcaccgagc tggaaatcaa gcggacagtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg acaacgccc  tgcagtccgg caactcccag    480
gaatccgtga ccgagcagga ctccaaggac agcacctaca gcctgtcctc cacctgacc    540 ctgtccaagg ccgactacga aagcacaag  gtgtacgcct gcgaagtgac ccaccagggc    600
ctgtctagcc ccgtgaccaa gtctttcaac cggggcgagt gctag                    645
```

<210> SEQ ID NO 25
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Leu Tyr Tyr Cys Gln Gln
                85                  90                  95

Tyr His Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
210                 215                 220
```

<210> SEQ ID NO 26
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Val Gln Leu Gln Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Met Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Leu Tyr Asp Gly Tyr Tyr Ala Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270
```

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 27
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gacattgtga tgtcacagtc tccatcctcc ctagctgtgt cagttggaga gaaggttact      60
atgagctgca agtccagtca gagccttttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg ggacagattt cactctcacc    240
attagcagtg tgaaggctga agacctggca ctttattact gtcagcaata tcatagctat    300
ccattcacgt tcggctcggg gacaaagctg gaaataaagc ggaccgtggc cgccccctcc    360
gtgttcatct tcccccctc cgacgagcag ctgaagtccg gcaccgcctc cgtggtgtgc     420
ctgctgaaca acttctaccc ccgggaggcc aaggtgcagt ggaaggtgga caacgccctg    480
cagtccggca actcccagga gtccgtgacc gagcaggact ccaaggactc cacctactcc    540
ctgtcctcca ccctgaccct gtccaaggcc gactacgaga gcacaaggt gtacgcctgc     600 gaggtgaccc accagggcct gtcctccccc gtgaccaagt ccttcaaccg gggcgagtgc    660
tag                                                                   663

<210> SEQ ID NO 28
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
caggtccaac tgcagcagcc tggggatgaa ctggtgaagc ctggggcttc agtgaagctg    60
tcctgcaagg cttctggcta caccttcacc agctactgga tgcagtgggt gaagcagagg   120
cctggacaag gccttgagtg gattggagag attaatccta gcaacggtcg tactaattat   180
aatgagatgt tcaagagcaa ggccacactg actgtagaca atcctccag cacagcctac    240 atgcaactca gcagcctgac atctgaggac tctgcggtct attactgtgc cctctatgat   300
ggttactacg ctatggacta ctggggtcaa ggaacctcag tcaccgtctc ctcagcctcc   360
accaagggcc catcggtctt ccccctggca ccctcctcca agagcacctc tgggggcaca   420
gcggccctgg gctgcctggt caaggactac ttccccgaac cggtgacggt gtcgtggaac   480
tcaggcgccc tgaccagcgg cgtgcacacc ttcccggccg tcctacagtc ctcaggactc   540
tactccctca gcagcgtggt gaccgtgccc tccagcagct gggcaccca  gacctacatc    600 tgcaacgtga atcacaagcc cagcaacacc aaggtggaca agagagttga gcccaaatct   660
tgtgacaaaa ctcacacatg cccaccgtgc ccagcacctg aactcctggg gggaccgtca   720
gtcttcctct tccccccaaa acccaaggac accctcatga tctcccggac ccctgaggtc   780
acatgcgtgg tggtggacgt gagccacgaa gaccctgagg tcaagttcaa ctggtacgtg   840
gacggcgtgg aggtgcataa tgccaagaca aagccgcggg aggagcagta caacagcacg   900
taccgtgtgg tcagcgtcct caccgtcctg caccaggact ggctgaatgg caaggagtac   960
aagtgcaagg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
agcctctccc tgtctccggg taaatga                                      1347
```

<210> SEQ ID NO 29
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Asp Ile Gln Met Thr Gln Ser Ser Ser Ser Phe Ser Val Ser Leu Gly
1               5                   10                  15

Asp Arg Val Thr Ile Thr Cys Lys Ala Asn Glu Asp Ile Asn Asn Arg
            20                  25                  30

Leu Ala Trp Tyr Gln Gln Thr Pro Gly Asn Ser Pro Arg Leu Leu Ile
        35                  40                  45

Ser Gly Ala Thr Asn Leu Val Thr Gly Val Pro Ser Arg Phe Ser Gly
    50                  55                  60

Ser Gly Ser Gly Lys Asp Tyr Thr Leu Thr Ile Thr Ser Leu Gln Ala
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Glu Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Met Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Leu Tyr Asp Gly Tyr Tyr Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 31
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacccagtc ctcctccagc ttctccgtgt ccctgggcga cagagtgacc     60
atcacatgca aggccaacga ggacatcaac aaccggctgg cctggtatca gcagaccccc    120
ggcaactccc ccagactgct gatctctggc gccaccaacc tcgtgaccgg cgtgcccagt    180
agattctccg gctctggctc cggcaaggac tacaccctga caatcacatc cctgcaggcc    240
gaggacttcg ccacctacta ctgccagcag tactggtcca ccccttcac ctttggcagc     300 ggcaccgagc tggaaatcaa gcggacagtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caacagccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gctag              645

<210> SEQ ID NO 32
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 32

```
caggtccaac tgcagcagcc tggggatgaa ctggtgaagc ctggggcttc agtgaagctg      60
tcctgcaagg cttctggcta ccttcacc agctactgga tgcagtgggt gaagcagagg      120
cctggacaag gccttgagtg gattggagag attaatccta gcaacggtcg tactaattat     180
aatgagatgt tcaagagcaa ggccacactg actgtagaca atcctccag cacagcctac      240
atgcaactca gcagcctgac atctgaggac tctgcggtct attactgtgc cctctatgat     300
ggttactacg ctatggacta ctggggtcaa ggaacctcag tcaccgtctc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggccg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gagagttga gcccaaatct     660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc     1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaatga                                         1347
```

<210> SEQ ID NO 33
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Gln Val Gln Leu Val Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Met Phe
    50                  55                  60

Lys Ser Lys Ala Val Leu Ser Val Asp Lys Ser Val Ser Thr Ala Tyr
65                  70                  75                  80

Met Gln Leu Ser Ser Leu Thr Ala Glu Asp Thr Ala Val Tyr Tyr Cys
                85                  90                  95

Ala Leu Tyr Asp Gly Tyr Tyr Ala Met Asp Tyr Trp Gly Gln Gly Thr
            100                 105                 110
```

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 34
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggtgcagc tggtgcagcc cggcgacgag ctggtgaagc ccggcgcctc cgtgaagctg      60
tcctgcaagg cctccggcta caccttcacc tcctactgga tgcagtgggt gaagcagcgg     120

-continued

```
cccggccagg gcctggagtg gatcggcgag atcaacccct ccaacggccg gaccaactac    180
aacgagatgt tcaagtccaa ggccgtgctg tccgtggaca agtccgtgtc caccgcctac    240
atgcagctgt cctccctgac cgccgaggac accgccgtgt actactgcgc cctgtacgac    300
ggctactacg ccatggacta ctggggccag ggcaccctgg tgaccgtgtc ctccgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccggccg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gagagttga gcccaaatct    660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca agccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga    1347
```

<210> SEQ ID NO 35
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Asp Ile Val Met Thr Gln Ser Pro Ser Ser Leu Ala Val Ser Val Gly
1               5                   10                  15

Glu Arg Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Val Ala Leu Tyr Tyr Cys Gln Gln
                85                  90                  95

Tyr His Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 36
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gacatcgtga tgacccagtc cccctcctcc ctggccgtgt ccgtgggcga gcgggtgacc      60
atgtcctgca agtcctccca gtccctgctg tactcctcca accagaagaa ctacctggcc     120
tggtaccagc agaagcccgg ccagtccccc aagctgctga tctactgggc ctccacccgg     180
gagtccggcg tgcccgaccg gttctccggc tccggctccg gcaccgactt cacccctgacc    240 atctcctccg tgaaggccga ggacgtggcc ctgtactact gccagcagta ccactcctac     300
cccttcacct tcggccaggg caccaagctg gagatcaagc ggaccgtggc cgccccctcc     360
gtgttcatct tccccccctc cgacgagcag ctgaagtccg gcaccgcctc cgtggtgtgc     420
ctgctgaaca acttctaccc ccgggaggcc aaggtgcagt ggaaggtgga caacgccctg     480
cagtccggca actcccagga gtccgtgacc gagcaggact ccaaggactc cacctactcc     540
ctgtcctcca ccctgaccct gtccaaggcc gactacgaga agcacaaggt gtacgcctgc     600
gaggtgaccc accagggcct gtcctccccc gtgaccaagt ccttcaaccg ggcgagtgc     660 tag                                                                   663

<210> SEQ ID NO 37
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Gly Tyr
            20                  25                  30

Trp Met His Trp Val Lys Gln Ala Pro Gly Gln Gly Leu Glu Trp Ile
        35                  40                  45

Gly Glu Ile Asn Pro Ser Asn Gly Arg Thr Asn Tyr Asn Glu Arg Phe
    50                  55                  60

Lys Ser Lys Ala Thr Leu Thr Val Asp Lys Ser Ile Thr Thr Ala Phe
65                  70                  75                  80

Met Glu Leu Ser Arg Leu Arg Ser Asp Asp Thr Ala Val Tyr Phe Cys
            85                  90                  95

Ala Arg Asp Tyr Tyr Gly Thr Ser Tyr Asn Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 38
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
caggtgcagc tggtgcagcc tggcgctgaa gtcgtgaagc caggcgcctc cgtgaagctg      60
tcctgcaagg cttccggcta caccttcacc ggctactgga tgcactgggt caagcaggcc     120
cctggacagg gcctggaatg gatcggcgag atcaaccctt ccaacggccg gaccaactac     180
aacgagcggt tcaagtccaa ggccaccctg accgtggaca gtccatcac caccgccttc     240
atggaactgt cccggctgag atccgacgat accgccgtgt acttctgcgc cagagactac     300
tacggcaccct cctacaactt cgactactgg ggccagggca ccctgctgac cgtgtcctct     360
gcttctacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggccgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                      1350
```

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Asp Ile Gln Met Thr Gln Ser Pro Ser Ser Leu Ser Val Ser Val Gly
1               5                  10                  15

Asp Arg Val Thr Ile Thr Cys Lys Ala Asn Glu Asp Ile Asn Asn Arg
            20                  25                  30

Leu Ala Trp Tyr Gln Gln Lys Pro Gly Lys Ala Pro Lys Leu Leu Ile
        35                  40                  45

Ser Gly Ala Thr Asn Leu Val Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Glu Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 40
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
gacatccaga tgacccagtc cccctcctcc ctgtccgtgt ctgtgggcga cagagtgacc      60
atcacatgca aggccaacga ggacatcaac aaccggctgg cctggtatca gcagaagccc     120
ggcaaggccc ccaagctgct gatctctggc gccaccaatc tcgtgaccgg cgtgccctcc     180
agattctccg gctctggctc tggcaccgac tataccctga ccatctccag cctgcagccc     240
gaggacttcg ccacctacta ctgccagcag tactggtcca ccccttcac ctttggccag      300
ggcaccgagc tggaaatcaa gcggacagtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctaca gcctgtcctc caccctgacc     540
ctgtccaagg ccgactacga gaagcacaag gtgtacgcct gcgaagtgac ccaccagggc     600
ctgtctagcc ccgtgaccaa gtctttcaac cggggcgagt gctag                     645
```

<210> SEQ ID NO 41
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Asp Ile Val Met Ser Gln Ser Pro Ser Ser Leu Ala Val Ser Val Gly
1               5                   10                  15
Glu Lys Val Thr Met Ser Cys Lys Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
```

```
                65                  70                  75                  80
Ile Ser Ser Val Lys Ala Glu Asp Leu Ala Leu Tyr Tyr Cys Gln Gln
                    85                  90                  95

Tyr His Ser Tyr Pro Phe Thr Phe Gly Ser Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 42
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
                35                  40                  45

Gly Glu Ile Asn Pro Ser Asn Gly Arg Thr Asn Tyr Asn Glu Met Phe
            50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Leu Tyr Asp Gly Tyr Tyr Ala Met Asp Tyr Trp Gly Gln Gly Thr
                100                 105                 110

Ser Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205
```

```
Asn Thr Lys Val Asp Lys Arg Val Glu Ser Lys Tyr Gly Pro Pro Cys
    210                 215                 220
Pro Ser Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 43
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
tacattgtga tgtcacagtc tccatcctcc ctagctgtgt cagttggaga gaaggttact      60
atgagctgca agtccagtca gagcctttta tatagtagca atcaaaagaa ctacttggcc     120
tggtaccagc agaaaccagg gcagtctcct aaactgctga tttactgggc atccactagg     180
gaatctgggg tccctgatcg cttcacaggc agtggatctg ggacagattt cactctcacc     240
attagcagtg tgaaggctga agacctggca ctttattact gtcagcaata tcatagctat     300
ccattcacgt tcggctcggg gacaaagctg gaaataaagc ggaccgtggc cgcccctcc      360 gtgttcatct tccccccctc cgacgagcag ctgaagtccg gcaccgcctc cgtggtgtgc     420
ctgctgaaca acttctaccc ccgggaggcc aaggtgcagt ggaaggtgga caacgccctg     480
cagtccggca actcccagga gtccgtgacc gagcaggact ccaaggactc cacctactcc     540
ctgtcctcca ccctgaccct gtccaaggcc gactacgaga agcacaaggt gtacgcctgc     600
gaggtgaccc accagggcct gtcctccccc gtgaccaagt ccttcaaccg gggcgagtgc     660
tag                                                                  663
```

<210> SEQ ID NO 44
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
caggtccaac tgcagcagcc tggggatgaa ctggtgaagc ctggggcttc agtgaagctg        60
tcctgcaagg cttctggcta caccttcacc agctactgga tgcagtgggt gaagcagagg       120
cctggacaag gccttgagtg gattggagag attaatccta gcaacggtcg tactaattat       180
aatgagatgt tcaagagcaa ggccacactg actgtagaca atcctccag cacagcctac       240
atgcaactca gcagcctgac atctgaggac tctgcggtct attactgtgc cctctatgat       300
ggttactacg ctatggacta ctggggtcaa ggaacctcag tcaccgtctc ctcagcctcc       360
accaagggcc cctccgtgtt cccctggcc cctgctccc ggtccacctc cgagtccacc         420
gccgccctgg gctgcctggt gaaggactac ttccccgagc ccgtgaccgt gtcctggaac       480
tccggcgccc tgacctccgg cgtgcacacc ttccccgccg tgctgcagtc ctccggcctg       540
tactccctgt cctccgtggg gaccgtgccc tcctcctccc tgggcaccaa gacctacacc       600
tgcaacgtgg accacaagcc ctccaacacc aaggtggaca gcgggtgga gtccaagtac        660
ggccccccct gccccctcctg ccccgccccc gagttcctgg gcggccctc cgtgttcctg       720
ttccccccca gcccaagga caccctgatg atctcccgga ccccgaggt gacctgcgtg         780
gtggtggacg tgtcccagga ggaccccgag gtgcagttca actggtacgt ggacggcgtg       840
gaggtgcaca cgccaagac caagcccgg gaggagcagt tcaactccac ctaccgggtg         900
gtgtccgtgc tgaccgtgct gcaccaggac tggctgaacg caaggagta caagtgcaag       960
gtgtccaaca gggcctgcc ctcctccatc gagaagacca ctccaaggc caagggccag       1020
ccccgggagc cccaggtgta caccctgccc ccctcccagg aggagatgac caagaaccag     1080
gtgtccctga cctgcctggt gaagggcttc taccctccg acatcgccgt ggagtgggag     1140
tccaacggcc agcccgagaa caactacaag accaccccc ccgtgctgga ctccgacggc     1200
tccttcttcc tgtactcccg gctgaccgtg gacaagtccc ggtggcagga gggcaacgtg     1260
ttctcctgct ccgtgatgca cgaggccctg cacaaccact acacccagaa gtccctgtcc     1320
ctgtccctgg gcaagtga                                                   1338
```

<210> SEQ ID NO 45
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Val Met Thr Gln Ser Pro Ser Leu Ala Val Ser Val Gly
1               5                   10                  15

Glu Arg Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
```

```
            50                  55                  60
Pro Asp Arg Phe Ser Gly Ser Gly Ser Gly Thr Asp Phe Thr Leu Thr
65                  70                  75                  80

Ile Ser Ser Val Lys Ala Glu Asp Val Ala Leu Tyr Tyr Cys Gln Gln
                85                  90                  95

Tyr His Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Met Phe
        50                  55                  60

Lys Ser Lys Ala Val Leu Ser Val Asp Lys Ser Val Ser Thr Ala Tyr
65                  70                  75                  80

Met Gln Leu Ser Ser Leu Thr Ala Glu Asp Thr Ala Val Tyr Tyr Cys
                85                  90                  95

Ala Leu Tyr Asp Gly Tyr Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 47
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacatcgtga tgacccagtc cccctcctcc ctggccgtgt ccgtgggcga gcgggtgacc       60
atgtcctgca gtcctcccca gtccctgctg tactcctcca accagaagaa ctacctggcc      120
tggtaccagc agaagcccgg ccagtccccc aagctgctga tctactgggc ctccacccgg      180
gagtccggcg tgcccgaccg gttctccggc tccggctccg gcaccgactt caccctgacc      240
atctcctccg tgaaggccga ggacgtggcc ctgtactact gccagcagta ccactcctac      300
cccttcacct tcggccaggg caccaagctg gagatcaagc ggaccgtggc cgccccctcc      360
gtgttcatct ccccccctc cgacgagcag ctgaagtccg gcaccgcctc cgtggtgtgc      420
ctgctgaaca acttctaccc ccgggaggcc aaggtgcagt ggaaggtgga caacgccctg      480
cagtccggca actcccagga gtccgtgacc gagcaggact ccaaggactc cacctactcc      540
ctgtcctcca ccctgaccct gtccaaggcc gactacgaga agcacaaggt gtacgcctgc      600

-continued

```
gaggtgaccc accagggcct gtcctccccc gtgaccaagt ccttcaaccg gggcgagtgc    660
tag                                                                  663
```

<210> SEQ ID NO 48
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
caggtgcagc tggtgcagcc cggcgacgag ctggtgaagc ccggcgcctc cgtgaagctg     60
tcctgcaagg cctccggcta caccttcacc tcctactgga tgcagtgggt gaagcagcgg    120
cccggccagg gctggagtg atcggcgag atcaaccct ccaacggccg gaccaactac       180
aacgagatgt tcaagtccaa ggccgtgctg tccgtggaca gtccgtgtc caccgcctac    240 atgcagctgt cctccctgac cgccgaggac accgccgtgt actactgcgc cctgtacgac    300
ggctactacg ccatggacta ctggggccag ggcacctgg tgaccgtgtc ctccgcctcc    360
accaagggcc cctccgtgtt cccctggcc cctgctccc ggtccacctc cgagtccacc     420
gccgccctgg gctgcctggt gaaggactac ttccccgagc ccgtgaccgt gtcctggaac    480
tccggcgccc tgacctccgg cgtgcacacc ttccccgccg tgctgcagtc ctccggcctg    540
tactccctgt cctccgtggt gaccgtgccc tcctcctccc tgggcaccaa gacctacacc    600
tgcaacgtgg accacaagcc ctccaacacc aaggtggaca gcggggtgga gtccaagtac    660
ggccccccct gccctcctg ccccgccccc gagttcctgg gcggcccctc cgtgttcctg    720
ttccccccca gccccaagga cacctgatg atctcccgga cccccgaggt gacctgcgtg    780
gtggtggacg tgtcccagga ggaccccgag gtgcagttca actggtacgt ggacggcgtg    840
gaggtgcaca cgccaagac caagcccgg gaggagcagt tcaactccac ctaccgggtg    900
gtgtccgtgc tgaccgtgct gcaccaggac tggctgaacg gcaaggagta caagtgcaag    960
gtgtccaaca agggcctgcc ctcctccatc gagaagacca tctccaaggc caagggccag   1020
ccccgggagc cccaggtgta cacctgcc ccctcccagg aggagatgac caagaaccag   1080
gtgtccctga cctgcctggt gaagggcttc taccctccg acatcgccgt ggagtgggag   1140
tccaacggcc agcccgagaa caactacaag accaccccc ccgtgctgga ctccgacggc   1200
tccttcttcc tgtactcccg gctgaccgtg gacaagtccc ggtggcagga gggcaacgtg   1260
ttctcctgct ccgtgatgca cgaggccctg cacaaccact acacccagaa gtccctgtcc   1320
ctgtccctgg gcaagtga                                                 1338
```

<210> SEQ ID NO 49
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Gln Pro Gly Asp Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
```

```
            35                  40                  45
Gly Glu Ile Asn Pro Ser Asn Gly Arg Thr Asn Tyr Asn Glu Met Phe
 50                  55                  60

Lys Ser Lys Ala Val Leu Ser Val Asp Lys Ser Val Ser Thr Ala Tyr
 65                  70                  75                  80

Met Gln Leu Ser Ser Leu Thr Ala Glu Asp Thr Ala Val Tyr Tyr Cys
                 85                  90                  95

Ala Leu Tyr Asp Gly Tyr Tyr Ala Met Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 50
```

```
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Ser Ser Leu Ala Val Ser Val Gly
1               5                   10                  15

Glu Arg Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Val Ala Leu Tyr Tyr Cys Gln Gln
                85                  90                  95

Tyr His Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Thr Ser Gly Gly
    210                 215                 220

Gly Gly Ser Gly Gly Gly Ser Gly Gly Gly Ser Gln Val Gln
225                 230                 235                 240

Leu Val Gln Ser Gly Gly Val Val Gln Pro Gly Arg Ser Leu Arg
                245                 250                 255

Leu Ser Cys Lys Ala Ser Gly Tyr Thr Phe Thr Arg Tyr Thr Met His
            260                 265                 270

Trp Val Arg Gln Ala Pro Gly Lys Cys Leu Glu Trp Ile Gly Tyr Ile
        275                 280                 285

Asn Pro Ser Arg Gly Tyr Thr Asn Tyr Asn Gln Lys Phe Lys Asp Arg
    290                 295                 300

Phe Thr Ile Ser Arg Asp Asn Ser Lys Asn Thr Ala Phe Leu Gln Met
305                 310                 315                 320

Asp Ser Leu Arg Pro Glu Asp Thr Gly Val Tyr Phe Cys Ala Arg Tyr
                325                 330                 335

Tyr Asp Asp His Tyr Ser Leu Asp Tyr Trp Gly Gln Gly Thr Pro Val
            340                 345                 350

Thr Val Ser Ser Gly Gly Gly Gly Ser Gly Gly Gly Ser Gly Gly
        355                 360                 365

Gly Gly Ser Gly Gly Gly Gly Ser Gly Gly Gly Gly Ser Gly Gly Gly
```

```
                    370                 375                 380
Gly Ser Asp Ile Gln Met Thr Gln Ser Pro Ser Ser Leu Ser Ala Ser
385                 390                 395                 400

Val Gly Asp Arg Val Thr Ile Thr Cys Ser Ala Ser Ser Val Ser
                405                 410                 415

Tyr Met Asn Trp Tyr Gln Gln Thr Pro Gly Lys Ala Pro Lys Arg Trp
                420                 425                 430

Ile Tyr Asp Thr Ser Lys Leu Ala Ser Gly Val Pro Ser Arg Phe Ser
                435                 440                 445

Gly Ser Gly Ser Gly Thr Asp Tyr Thr Phe Thr Ile Ser Ser Leu Gln
                450                 455                 460

Pro Glu Asp Ile Ala Thr Tyr Tyr Cys Gln Gln Trp Ser Ser Asn Pro
465                 470                 475                 480

Phe Thr Phe Gly Cys Gly Thr Lys Leu Gln Ile Thr Arg
                485                 490

<210> SEQ ID NO 51
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Gly Tyr
                20                  25                  30

Trp Met His Trp Val Lys Gln Ala Pro Gly Gln Gly Leu Glu Trp Ile
            35                  40                  45

Gly Glu Ile Asn Pro Ser Asn Gly Arg Thr Asn Tyr Asn Glu Arg Phe
        50                  55                  60

Lys Ser Lys Ala Thr Leu Thr Val Asp Lys Ser Ile Thr Thr Ala Phe
65                  70                  75                  80

Met Glu Leu Ser Arg Leu Arg Ser Asp Asp Thr Ala Val Tyr Phe Cys
                85                  90                  95

Ala Arg Asp Tyr Tyr Gly Thr Ser Tyr Asn Phe Asp Tyr Trp Gly Gln
                100                 105                 110

Gly Thr Leu Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Val Ser Val Gly
1               5                   10                  15

Asp Arg Val Thr Ile Thr Cys Lys Ala Asn Glu Asp Ile Asn Asn Arg
            20                  25                  30

Leu Ala Trp Tyr Gln Gln Lys Pro Gly Lys Ala Pro Lys Leu Leu Ile
        35                  40                  45

Ser Gly Ala Thr Asn Leu Val Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Gly Gly
            340                 345                 350

Gly Gly Ser Gly Gly Gly Ser Gly Gly Gly Ser Gly Gly Gly
        355                 360                 365

Gly Ser Gly Gly Gly Ser Gly Gly Gly Ser Asp Ile Gln Met
        370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
            485

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Thr Phe Thr Ser Tyr Trp Met Gln

```
<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Ile Asn Pro Ser Asn Gly Arg Thr Asn Tyr Asn Glu Met Phe Lys
1               5                   10                  15
Ser

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Asp Gly Tyr Tyr Ala Met Asp Tyr
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Ser Ser Gln Ser Leu Leu Tyr Ser Ser Asn Gln Lys Asn Tyr Leu
1               5                   10                  15
Ala

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Ala Ser Thr Arg Glu Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln Tyr His Ser Tyr Pro Phe Thr
1               5

<210> SEQ ID NO 59
<211> LENGTH: 384
```

-continued

```
<212> TYPE: PRT
<213> ORGANISM: Homo sapiens

<400> SEQUENCE: 59
```

| | | | | | | | | | | | | | | | |
|---|---|---|---|---|---|---|---|---|---|---|---|---|---|---|---|
| Ala | Pro | Thr | Lys | Ala | Pro | Asp | Val | Phe | Pro | Ile | Ile | Ser | Gly | Cys | Arg |
| 1 | | | | 5 | | | | | 10 | | | | | 15 | |
| His | Pro | Lys | Asp | Asn | Ser | Pro | Val | Val | Leu | Ala | Cys | Leu | Ile | Thr | Gly |
| | | | 20 | | | | | 25 | | | | | 30 | | |
| Tyr | His | Pro | Thr | Ser | Val | Thr | Val | Thr | Trp | Tyr | Met | Gly | Thr | Gln | Ser |
| | | 35 | | | | | 40 | | | | | 45 | | | |
| Gln | Pro | Gln | Arg | Thr | Phe | Pro | Glu | Ile | Gln | Arg | Arg | Asp | Ser | Tyr | Tyr |
| | 50 | | | | | 55 | | | | | 60 | | | | |
| Met | Thr | Ser | Ser | Gln | Leu | Ser | Thr | Pro | Leu | Gln | Gln | Trp | Arg | Gln | Gly |
| 65 | | | | | 70 | | | | 75 | | | | | | 80 |
| Glu | Tyr | Lys | Cys | Val | Val | Gln | His | Thr | Ala | Ser | Lys | Ser | Lys | Lys | Glu |
| | | | | 85 | | | | | 90 | | | | | 95 | |
| Ile | Phe | Arg | Trp | Pro | Glu | Ser | Pro | Lys | Ala | Gln | Ala | Ser | Ser | Val | Pro |
| | | | 100 | | | | | 105 | | | | | 110 | | |
| Thr | Ala | Gln | Pro | Gln | Ala | Glu | Gly | Ser | Leu | Ala | Lys | Ala | Thr | Thr | Ala |
| | | 115 | | | | | 120 | | | | | 125 | | | |
| Pro | Ala | Thr | Thr | Arg | Asn | Thr | Gly | Arg | Gly | Gly | Glu | Glu | Lys | Lys | Lys |
| | 130 | | | | | 135 | | | | | 140 | | | | |
| Glu | Lys | Glu | Lys | Glu | Glu | Gln | Glu | Glu | Arg | Glu | Thr | Lys | Thr | Pro | Glu |
| 145 | | | | | 150 | | | | 155 | | | | | | 160 |
| Cys | Pro | Ser | His | Thr | Gln | Pro | Leu | Gly | Val | Tyr | Leu | Leu | Thr | Pro | Ala |
| | | | | 165 | | | | | 170 | | | | | 175 | |
| Val | Gln | Asp | Leu | Trp | Leu | Arg | Asp | Lys | Ala | Thr | Phe | Thr | Cys | Phe | Val |
| | | | 180 | | | | | 185 | | | | | 190 | | |
| Val | Gly | Ser | Asp | Leu | Lys | Asp | Ala | His | Leu | Thr | Trp | Glu | Val | Ala | Gly |
| | | 195 | | | | | 200 | | | | | 205 | | | |
| Lys | Val | Pro | Thr | Gly | Gly | Val | Glu | Glu | Gly | Leu | Leu | Glu | Arg | His | Ser |
| | 210 | | | | | 215 | | | | | 220 | | | | |
| Asn | Gly | Ser | Gln | Ser | Gln | His | Ser | Arg | Leu | Thr | Leu | Pro | Arg | Ser | Leu |
| 225 | | | | | 230 | | | | 235 | | | | | | 240 |
| Trp | Asn | Ala | Gly | Thr | Ser | Val | Thr | Cys | Thr | Leu | Asn | His | Pro | Ser | Leu |
| | | | | 245 | | | | | 250 | | | | | 255 | |
| Pro | Pro | Gln | Arg | Leu | Met | Ala | Leu | Arg | Glu | Pro | Ala | Ala | Gln | Ala | Pro |
| | | | 260 | | | | | 265 | | | | | 270 | | |
| Val | Lys | Leu | Ser | Leu | Asn | Leu | Leu | Ala | Ser | Ser | Asp | Pro | Pro | Glu | Ala |
| | | 275 | | | | | 280 | | | | | 285 | | | |
| Ala | Ser | Trp | Leu | Leu | Cys | Glu | Val | Ser | Gly | Phe | Ser | Pro | Pro | Asn | Ile |
| | 290 | | | | | 295 | | | | | 300 | | | | |
| Leu | Leu | Met | Trp | Leu | Glu | Asp | Gln | Arg | Glu | Val | Asn | Thr | Ser | Gly | Phe |
| 305 | | | | | 310 | | | | 315 | | | | | | 320 |
| Ala | Pro | Ala | Arg | Pro | Pro | Gln | Pro | Gly | Ser | Thr | Thr | Phe | Trp | Ala | |
| | | | | 325 | | | | | 330 | | | | | 335 | |
| Trp | Ser | Val | Leu | Arg | Val | Pro | Ala | Pro | Pro | Ser | Pro | Gln | Pro | Ala | Thr |
| | | | 340 | | | | | 345 | | | | | 350 | | |
| Tyr | Thr | Cys | Val | Val | Ser | His | Glu | Asp | Ser | Arg | Thr | Leu | Leu | Asn | Ala |
| | | 355 | | | | | 360 | | | | | 365 | | | |
| Ser | Arg | Ser | Leu | Glu | Val | Ser | Tyr | Val | Thr | Asp | His | Gly | Pro | Met | Lys |
| | 370 | | | | | 375 | | | | | 380 | | | | |

```
<210> SEQ ID NO 60
```

```
<211> LENGTH: 330
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 326
<212> TYPE: PRT
<213> ORGANISM: Homo sapiens

<400> SEQUENCE: 61

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 62
<211> LENGTH: 377
<212> TYPE: PRT
<213> ORGANISM: Homo sapiens

<400> SEQUENCE: 62

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser

```
                50                  55                  60
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 63
<211> LENGTH: 452
<212> TYPE: PRT
<213> ORGANISM: Homo sapiens

<400> SEQUENCE: 63

Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
                35                  40                  45
```

```
Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
    195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
    275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
    355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
    435                 440                 445

Gly Thr Cys Tyr
450
```

<210> SEQ ID NO 64
<211> LENGTH: 327
<212> TYPE: PRT
<213> ORGANISM: Homo sapiens

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 65
<211> LENGTH: 353
<212> TYPE: PRT
<213> ORGANISM: Homo sapiens

<400> SEQUENCE: 65

Ala Ser Pro Thr Ser Pro Lys Val Phe Pro Leu Ser Leu Cys Ser Thr

| | 1 | | | | 5 | | | | | 10 | | | | | 15 | |
|---|---|---|---|---|---|---|---|---|---|---|---|---|---|---|---|---|
| | Gln | Pro | Asp | Gly | Asn | Val | Val | Ile | Ala | Cys | Leu | Val | Gln | Gly | Phe | Phe |
| | | | | 20 | | | | | 25 | | | | | 30 | | |
| | Pro | Gln | Glu | Pro | Leu | Ser | Val | Thr | Trp | Ser | Glu | Ser | Gly | Gln | Gly | Val |
| | | | | 35 | | | | | 40 | | | | | 45 | | |
| | Thr | Ala | Arg | Asn | Phe | Pro | Pro | Ser | Gln | Asp | Ala | Ser | Gly | Asp | Leu | Tyr |
| | | | | 50 | | | | | 55 | | | | | 60 | | |
| | Thr | Thr | Ser | Ser | Gln | Leu | Thr | Leu | Pro | Ala | Thr | Gln | Cys | Leu | Ala | Gly |
| | 65 | | | | | 70 | | | | | 75 | | | | | 80 |
| | Lys | Ser | Val | Thr | Cys | His | Val | Lys | His | Tyr | Thr | Asn | Pro | Ser | Gln | Asp |
| | | | | | 85 | | | | | 90 | | | | | 95 | |
| | Val | Thr | Val | Pro | Cys | Pro | Val | Pro | Ser | Thr | Pro | Pro | Thr | Pro | Ser | Pro |
| | | | | 100 | | | | | 105 | | | | | 110 | | |
| | Ser | Thr | Pro | Pro | Thr | Pro | Ser | Pro | Ser | Cys | Cys | His | Pro | Arg | Leu | Ser |
| | | | | 115 | | | | | 120 | | | | | 125 | | |
| | Leu | His | Arg | Pro | Ala | Leu | Glu | Asp | Leu | Leu | Leu | Gly | Ser | Glu | Ala | Asn |
| | | | | 130 | | | | | 135 | | | | | 140 | | |
| | Leu | Thr | Cys | Thr | Leu | Thr | Gly | Leu | Arg | Asp | Ala | Ser | Gly | Val | Thr | Phe |
| | 145 | | | | | 150 | | | | | 155 | | | | | 160 |
| | Thr | Trp | Thr | Pro | Ser | Ser | Gly | Lys | Ser | Ala | Val | Gln | Gly | Pro | Pro | Glu |
| | | | | | 165 | | | | | 170 | | | | | 175 | |
| | Arg | Asp | Leu | Cys | Gly | Cys | Tyr | Ser | Val | Ser | Ser | Val | Leu | Pro | Gly | Cys |
| | | | | 180 | | | | | 185 | | | | | 190 | | |
| | Ala | Glu | Pro | Trp | Asn | His | Gly | Lys | Thr | Phe | Thr | Cys | Thr | Ala | Ala | Tyr |
| | | | | 195 | | | | | 200 | | | | | 205 | | |
| | Pro | Glu | Ser | Lys | Thr | Pro | Leu | Thr | Ala | Thr | Leu | Ser | Lys | Ser | Gly | Asn |
| | | | | 210 | | | | | 215 | | | | | 220 | | |
| | Thr | Phe | Arg | Pro | Glu | Val | His | Leu | Leu | Pro | Pro | Pro | Ser | Glu | Glu | Leu |
| | 225 | | | | | 230 | | | | | 235 | | | | | 240 |
| | Ala | Leu | Asn | Glu | Leu | Val | Thr | Leu | Thr | Cys | Leu | Ala | Arg | Gly | Phe | Ser |
| | | | | | 245 | | | | | 250 | | | | | 255 | |
| | Pro | Lys | Asp | Val | Leu | Val | Arg | Trp | Leu | Gln | Gly | Ser | Gln | Glu | Leu | Pro |
| | | | | 260 | | | | | 265 | | | | | 270 | | |
| | Arg | Glu | Lys | Tyr | Leu | Thr | Trp | Ala | Ser | Arg | Gln | Glu | Pro | Ser | Gln | Gly |
| | | | | 275 | | | | | 280 | | | | | 285 | | |
| | Thr | Thr | Thr | Phe | Ala | Val | Thr | Ser | Ile | Leu | Arg | Val | Ala | Ala | Glu | Asp |
| | | | | 290 | | | | | 295 | | | | | 300 | | |
| | Trp | Lys | Lys | Gly | Asp | Thr | Phe | Ser | Cys | Met | Val | Gly | His | Glu | Ala | Leu |
| | 305 | | | | | 310 | | | | | 315 | | | | | 320 |
| | Pro | Leu | Ala | Phe | Thr | Gln | Lys | Thr | Ile | Asp | Arg | Leu | Ala | Gly | Lys | Pro |
| | | | | | 325 | | | | | 330 | | | | | 335 | |
| | Thr | His | Val | Asn | Val | Ser | Val | Val | Met | Ala | Glu | Val | Asp | Gly | Thr | Cys |
| | | | | 340 | | | | | 345 | | | | | 350 | | |
| | Tyr | | | | | | | | | | | | | | | |

<210> SEQ ID NO 66
<211> LENGTH: 340
<212> TYPE: PRT
<213> ORGANISM: Homo sapiens

<400> SEQUENCE: 66

| | 1 | | | | 5 | | | | | 10 | | | | | 15 | |
|---|---|---|---|---|---|---|---|---|---|---|---|---|---|---|---|---|
| | Ala | Ser | Pro | Thr | Ser | Pro | Lys | Val | Phe | Pro | Leu | Ser | Leu | Asp | Ser | Thr |
| | Pro | Gln | Asp | Gly | Asn | Val | Val | Val | Ala | Cys | Leu | Val | Gln | Gly | Phe | Phe |

```
                    20                  25                  30
Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Pro Asp Gly
 65                  70                  75                  80

Lys Ser Val Thr Cys His Val Lys His Tyr Thr Asn Pro Ser Gln Asp
                    85                  90                  95

Val Thr Val Pro Cys Pro Val Pro Pro Pro Pro Cys Cys His Pro
                100                 105                 110

Arg Leu Ser Leu His Arg Pro Ala Leu Glu Asp Leu Leu Leu Gly Ser
                115                 120                 125

Glu Ala Asn Leu Thr Cys Thr Leu Thr Gly Leu Arg Asp Ala Ser Gly
                130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
                180                 185                 190

Ala Ala His Pro Glu Leu Lys Thr Pro Leu Thr Ala Asn Ile Thr Lys
                195                 200                 205

Ser Gly Asn Thr Phe Arg Pro Glu Val His Leu Leu Pro Pro Pro Ser
            210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
            305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 67
<211> LENGTH: 106
<212> TYPE: PRT
<213> ORGANISM: Homo sapiens

<400> SEQUENCE: 67

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45
```

```
Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

```
<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Tyr Trp Met His
1               5
```

```
<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Ile Asn Pro Ser Asn Gly Arg Thr Asn Tyr Asn Glu Arg Phe Lys
1               5                   10                  15

Ser
```

```
<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Tyr Tyr Gly Thr Ser Tyr Asn Phe Asp Tyr
1               5                   10
```

```
<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Ala Asn Glu Asp Ile Asn Asn Arg Leu Ala
1               5                   10
```

```
<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 72

Gly Ala Thr Asn Leu Val Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Tyr Trp Ser Thr Pro Phe Thr
1               5

<210> SEQ ID NO 74
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Pro Lys Glu Thr Val Lys Pro Val Glu Val Glu Gly Glu Ser Val
1               5                   10                  15

Val Leu Pro Cys Asn Pro Pro Ser Ala Glu Pro Leu Arg Ile Tyr
                20                  25                  30

Trp Met Asn Ser Lys Ile Leu His Ile Lys Gln Asp Glu Arg Val Thr
            35                  40                  45

Met Gly Gln Asn Gly Asn Leu Tyr Phe Ala Asn Val Leu Thr Ser Asp
        50                  55                  60

Asn His Ser Asp Tyr Ile Cys His Ala His Phe Pro Gly Thr Arg Thr
65                  70                  75                  80

Ile Ile Gln Lys Glu Pro Ile Asp
                85

<210> SEQ ID NO 75
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Thr Gln Ile Thr Gln Gly Pro Arg Ser Thr Ile Glu Lys Lys Gly Ser
1               5                   10                  15

Arg Val Thr Phe Thr Cys Gln Ala Ser Phe Asp Pro Ser Leu Gln Pro
                20                  25                  30

Ser Ile Thr Trp Arg Gly Asp Gly Arg Asp Leu Gln Glu Leu Gly Asp
            35                  40                  45

Ser Asp Lys Tyr Phe Ile Glu Asp Gly Arg Leu Val Ile His Ser Leu
        50                  55                  60

Asp Tyr Ser Asp Gln Gly Asn Tyr Ser Cys Val Ala Ser Thr Glu Leu
65                  70                  75                  80

Asp Val Val Glu Ser Arg Ala Gln Leu Leu
                85                  90

<210> SEQ ID NO 76
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Gly Gly Ser
1               5

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(75)
<223> OTHER INFORMATION: This sequence may encompass 1-15 'Gly Gly Gly
      Gly Ser' repeating units
<220> FEATURE:
<223> OTHER INFORMATION: See specification as filed for detailed
      description of substitutions and preferred embodiments

<400> SEQUENCE: 78

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser
65                  70                  75

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 79

His His His His His His
1               5
```